United States Patent [19]
Crowley et al.

[11] Patent Number: 6,004,269
[45] Date of Patent: *Dec. 21, 1999

[54] CATHETERS FOR IMAGING, SENSING ELECTRICAL POTENTIALS, AND ABLATING TISSUE

[75] Inventors: Robert J. Crowley, Wayland; John E. Abele, Concord, both of Mass.; Charles D. Lennox, Hudson, N.H.; Susan M. Ropiak, Hanscom Air Force Base, Mass.

[73] Assignee: Boston Scientific Corporation, Watertown, Mass.

[*] Notice: This patent is subject to a terminal disclaimer.

[21] Appl. No.: 08/473,137

[22] Filed: Jun. 7, 1995

Related U.S. Application Data

[63] Continuation-in-part of application No. 08/086,523, Jul. 1, 1993, abandoned, application No. 08/086,543, Jul. 1, 1993, abandoned, and application No. 08/086,740, Jul. 1, 1993, abandoned.

[51] Int. Cl.$^6$ .............................. A61B 8/00; A61B 5/04; A61N 1/06
[52] U.S. Cl. ........................... 600/439; 600/374; 606/27; 607/122
[58] Field of Search ............................... 128/642, 660.03, 128/662.06; 606/45, 49–50, 27; 604/22, 96–103; 607/122; 600/374, 439, 443, 462–463

[56] References Cited

U.S. PATENT DOCUMENTS

| | | | |
|---|---|---|---|
| 4,249,539 | 2/1981 | Vilkomerson et al. | 128/660 |
| 4,407,294 | 10/1983 | Vilkomerson | 128/660 |

(List continued on next page.)

FOREIGN PATENT DOCUMENTS

| | | | |
|---|---|---|---|
| 1220673 | 3/1986 | U.S.S.R. | 607/126 |

OTHER PUBLICATIONS

ASM International, "Surface Engineering," Advanced Materials & Processes®, Dec. 1990, vol. 138, issue 6.

Avitall et al., "The Physics and Engineering of Transcatheter Cardiac Tissue Ablation," University of Wisconsin–Milwaukee Clinical Campus, Sinai Samaritan Medical Center, Milwaukee, Wisconsin.

The BBI Newsletter, "Interventional Electrophysiology Poised for Growth," Sep. 12, 1991, vol. 14, No. 9, pp. 162–165.

Becker et al., "Radiofrequency Ballon Angioplasty: Rationale and Proof of Principle," Nov. 1988, Investigative Radiology, vol. 23, No. 11, pp. 810–817.

Berns et al., "Feasibility of Radiofrequency–Powered, Thermal Balloon Ablation of Atrioventricular Bypass Tracts Via the Coronary Sinus," Nov. 11–14, 1991, Anaheim Convention Center, Anaheim, California.

(List continued on next page.)

*Primary Examiner*—Francis J. Jaworski
*Attorney, Agent, or Firm*—Lyon & Lyon LLP

[57] ABSTRACT

An acoustic imaging system for use within a heart has a catheter (6), an ultrasound device (10) incorporated into the catheter (6), and an electrode (300, 304, 334, 394) mounted on the catheter (6). The ultrasound device (10) directs ultrasonic signals toward an internal structure in the heart to create an ultrasonic image, and the electrode (300, 304, 334, 394) is arranged for electrical contact with the internal structure. A chemical ablation device (55, 86, 314, 396) mounted on the catheter (6) ablates at least a portion of the internal structure by delivery of fluid to the internal structure. The ablation device (55) may include a material that vibrates in response to electrical excitation, the ablation being at least assisted by vibration of the material. The ablation device may alternatively be a transducer (414) incorporated into the catheter (6), arranged to convert electrical signals into radiation and to direct the radiation toward the internal structure. The electrode may be a sonolucent structure (304, 334) incorporated into the catheter (6).

13 Claims, 32 Drawing Sheets

U.S. PATENT DOCUMENTS

| | | | |
|---|---|---|---|
| 4,641,649 | 2/1987 | Walinsky et al. | 128/303.1 |
| 4,676,258 | 6/1987 | Inokuchi et al. | 128/804 |
| 4,709,698 | 12/1987 | Johnston et al. | 128/303.12 |
| 4,776,349 | 10/1988 | Nashef et al. | 607/122 |
| 4,821,731 | 4/1989 | Martinelli et al. | 128/662.06 |
| 4,841,977 | 6/1989 | Griffith et al. | 128/660.03 |
| 4,936,281 | 6/1990 | Stasz . | |
| 4,940,064 | 7/1990 | Desai | 607/122 |
| 4,951,677 | 8/1990 | Crowley et al. . | |
| 4,955,377 | 9/1990 | Lennox et al. | 128/401 |
| 4,998,933 | 3/1991 | Eggers et al. | 606/41 |
| 5,000,185 | 3/1991 | Yock | 128/662.03 |
| 5,054,492 | 10/1991 | Scribner et al. | 128/662.06 |
| 5,103,804 | 4/1992 | Abele et al. | 128/4 |
| 5,106,360 | 4/1992 | Ishiwara et al. | 600/2 |
| 5,125,410 | 6/1992 | Misono et al. | 128/662.06 |
| 5,131,397 | 7/1992 | Crowley | 128/662.06 |
| 5,140,987 | 8/1992 | Schuger et al. | 128/642 |
| 5,156,151 | 10/1992 | Imran | 128/642 |
| 5,190,046 | 3/1993 | Shturman | 128/662.06 |
| 5,211,176 | 5/1993 | Ishiguro et al. | 128/662.06 |
| 5,222,501 | 6/1993 | Ideker et al. | 128/660.03 |
| 5,255,678 | 10/1993 | Deslauriers et al. | 607/122 |
| 5,263,493 | 11/1993 | Avitall | 128/642 |
| 5,277,201 | 1/1994 | Stern | 607/99 |
| 5,281,215 | 1/1994 | Milder | 606/20 |
| 5,295,484 | 3/1994 | Marcus et al. | 128/660.03 |
| 5,295,962 | 3/1994 | Crocher et al. | 604/96 |
| 5,313,943 | 5/1994 | Houser et al. | 606/41 |
| 5,323,781 | 6/1994 | Ideker et al. | 128/660.03 |
| 5,324,255 | 6/1994 | Passafaro et al. | 604/49 |
| 5,325,860 | 7/1994 | Seward et al. | 128/660.03 |
| 5,336,222 | 8/1994 | Durgin, Jr. et al. | 606/50 |
| 5,368,035 | 11/1994 | Hamm et al. | 128/662.06 |
| 5,372,138 | 12/1994 | Crowley et al. | 128/662.06 |
| 5,375,601 | 12/1994 | Nicholas et al. | 128/662.06 |
| 5,383,460 | 1/1995 | Jang et al. | 128/660.03 |
| 5,403,311 | 4/1995 | Abele et al. | 606/49 |
| 5,464,016 | 11/1995 | Nicholas et al. | 128/662.06 |
| 5,540,679 | 7/1996 | Fram et al. | 606/27 |
| 5,588,432 | 12/1996 | Crowley | 128/662.06 |
| 5,609,606 | 3/1997 | O'Boyle | 606/194 |

OTHER PUBLICATIONS

Bom, N. et al., "Early and Present Examples of Intraluminal Ultrasonic Echography," 1989, Catheter–Based Sensing and Imaging Technology, SPIE, vol. 1068, pp. 146–150.

Borggrefe et al., "Catheter Ablation Using Radiofrequency Energy," Feb., 1990, Clinical Cardiology, vol. 13, pp. 127–131.

Buxton, "Catheter Ablation of Atrioventricular Bypass Tracts: Still an Investigational Procedure," Jun., 1989, Circulation, vol. 79, No. 6, pp. 1388–1390.

Calkins et al., "Diagnosis and Cure of the Wolff–Parkinson–White Syndrome or Paroxysmal Supraventricular Tachycardias During a Single Electrophysiologic Test," Jun. 6, 1991, N.E. Journal of Medicine, v. 324, No. 23.

Critelli, "Transcatheter Ablation of Tachyarrhythmias: An Evolving Therapeutic Procedure," 1989, Journal of Interventional Cardiology, vol. 2, No. 4, pp. 233–236.

Crowley et al., "Optimized Ultrasound Imaging Catheters for use in the Vascular System," 1989, International Journal of Cardiac Imaging, vol. 4, pp. 145–151.

Crowley et al., "Ultrasound Guided Therapeutic Catheters: Recent Developments and Clinical Results," 1991, International Journal of Cardiac Imaging, vol. 6, pp. 145–156.

Ellis et al., "Ultrasonic Imaging Catheter," 1988, Microvasive, Inc.

Fram et al., United States Patent Application Serial No. 07/957,533, filed Oct. 5, 1992, "Device and Method for Heating Tissue in a Patients's Body".

Frank et al., "Implantable Cardioverter–Defibrillators: Alternative Treatment for Ventricular Tachyarrhythmias," Mar., 1992, Coronary Artery Disease, vol. 3, No. 3, pp. 210–217, Current Science ISSN 0954–6928 Haywood, "Dual IBAD Makes Good Coatings".

Jackman et al., "Catheter Ablation of Accessory Atrioventricular Pathways (Wolff–Parkinson–White Syndrome) by Radiofrequency Current," Jun. 6, 1991, New England Journal of Medicine, vol. 324, No. 23.

Lesh, "Application of Ultrasoound Imaging to Catheter Ablation of Cardiac Arrhythmias," Nov., 1992, Biomedical Business International.

Mahomed et al., "Surgery for Wolff–Parkinson–White Syndrome," Mar., 1992, Coronary Artery Disease, vol. 3, No. 3, pp. 175–185, Current Science ISSN 0954–6928.

Mansfield™ "Anatomy and Physiology," from "Electrophysiology" brochure.

Mansfield™ (Boston Scientific Corporation), "Explorer™ Series Electrophysiology Mapping Catheters" brochure.

Mansfield™ (Boston Scientific Corporation), "Explorer 360°™ Series Advanced Electrophysiology Mapping Catheters" brochure.

Mansfield™ (Boston Scientific Corporation), "Polaris™ Series Steerable/Deflectable Tip Mapping Catheters" brochure.

McGuire et al., "Surgical Techniques for the Cure of Atrioventricular Junctional Reentrant Tachycardia," Mar., 1992, Coronary Artery Disease, vol. 3, No. 3, pp. 186–191, Current Science ISSN 0954–6928.

McMath, "Percutaneous Laser Ballon Coagulation of Accessory Pathways," 1991, SPIE, vol. 1425, pp. 165–169.

Meditech®, "The Soft Steerable Catheter System for Rapid G I Intubation for Decompression and Sampling" brochure, Oct., 1978.

Microvasive (Boston Scientific Corporation), "Gold Probe™—The Next Generation in Biopolar Hemostasis" brochure.

Saksena et al., "Low–Energy Transvenous Ablation of the Canine Atrioventricular Conduction System with a Suction Electrode Catheter," Aug., 1987, Circulation, vol. 76, No. 2, pp. 394–403.

Schuger et al., "Long–Term Effects of Percutaneous Laser Ballon Ablation from the Canine Coronary Sinus," May 18, 1992, pp. 947–954.

Schuger et al., "Percutaneous Transcatheter Laser Ballon Ablation from the Canine Coronary Sinus: Implications for the Wolff–Parkinson–White Syndrome," 1990, Lasers in Surgery and Medicine, vol. 10, No. 2

Selle, "Definitive Surgery for Postinfarction Ventricular Tachycardia," Mar., 1992, Coronary Artery Disease, vol. 3, No. 3, pp. 204–209, Current Science ISSN 0954–6928.

Sung, "Arrhythmias and the Autonomic Nervous System," Sep., 1987, Cardio, pp. 77–80.

Tarjan et al., "An Experimental Device for Low–Energy, Precise Ablation of AV Conduction," Nov.–Dec., 1986, PACE, vol. 9, pp. 1396–1402.

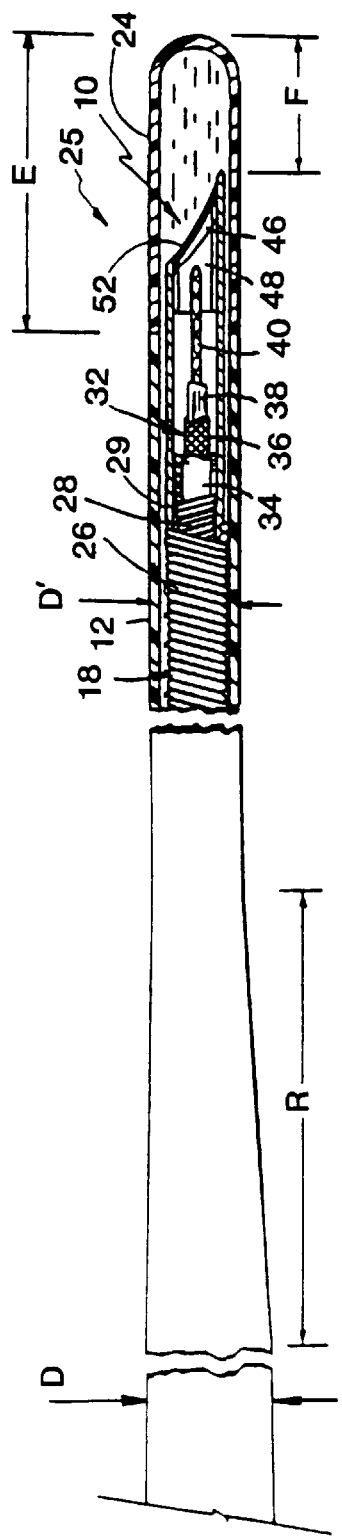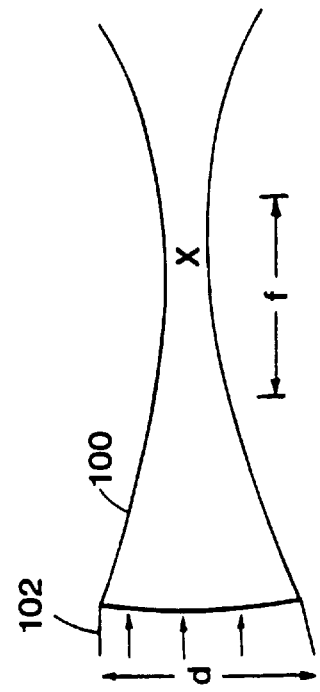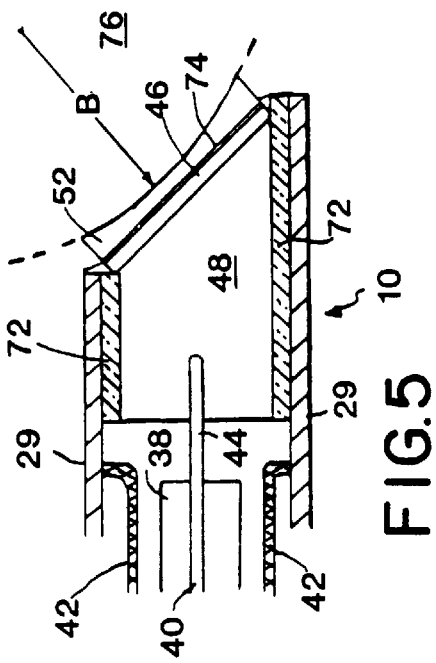
FIG. 4
FIG. 6
FIG. 5

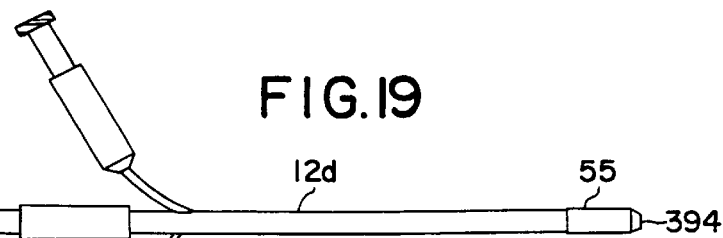
FIG.19
FIG.19a
FIG.19b
FIG.19c
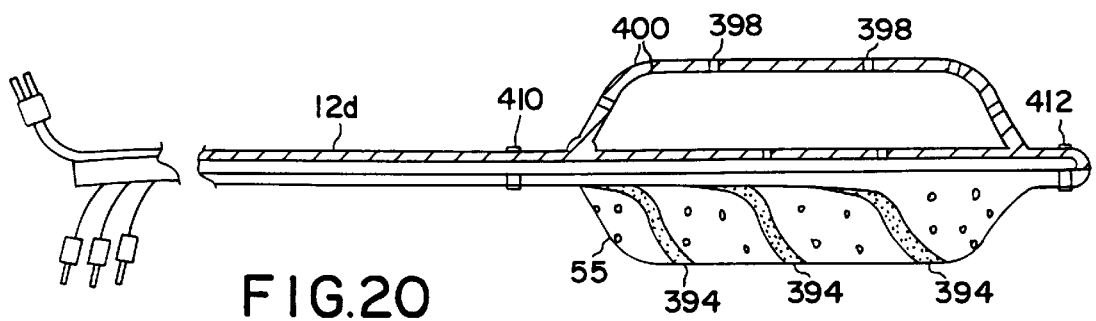
FIG.20
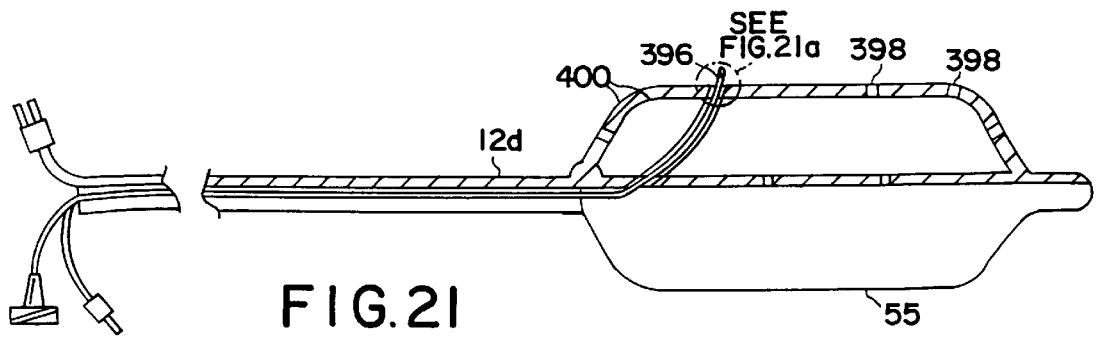
FIG.21
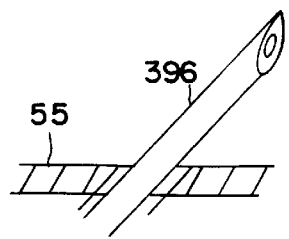
FIG.21a

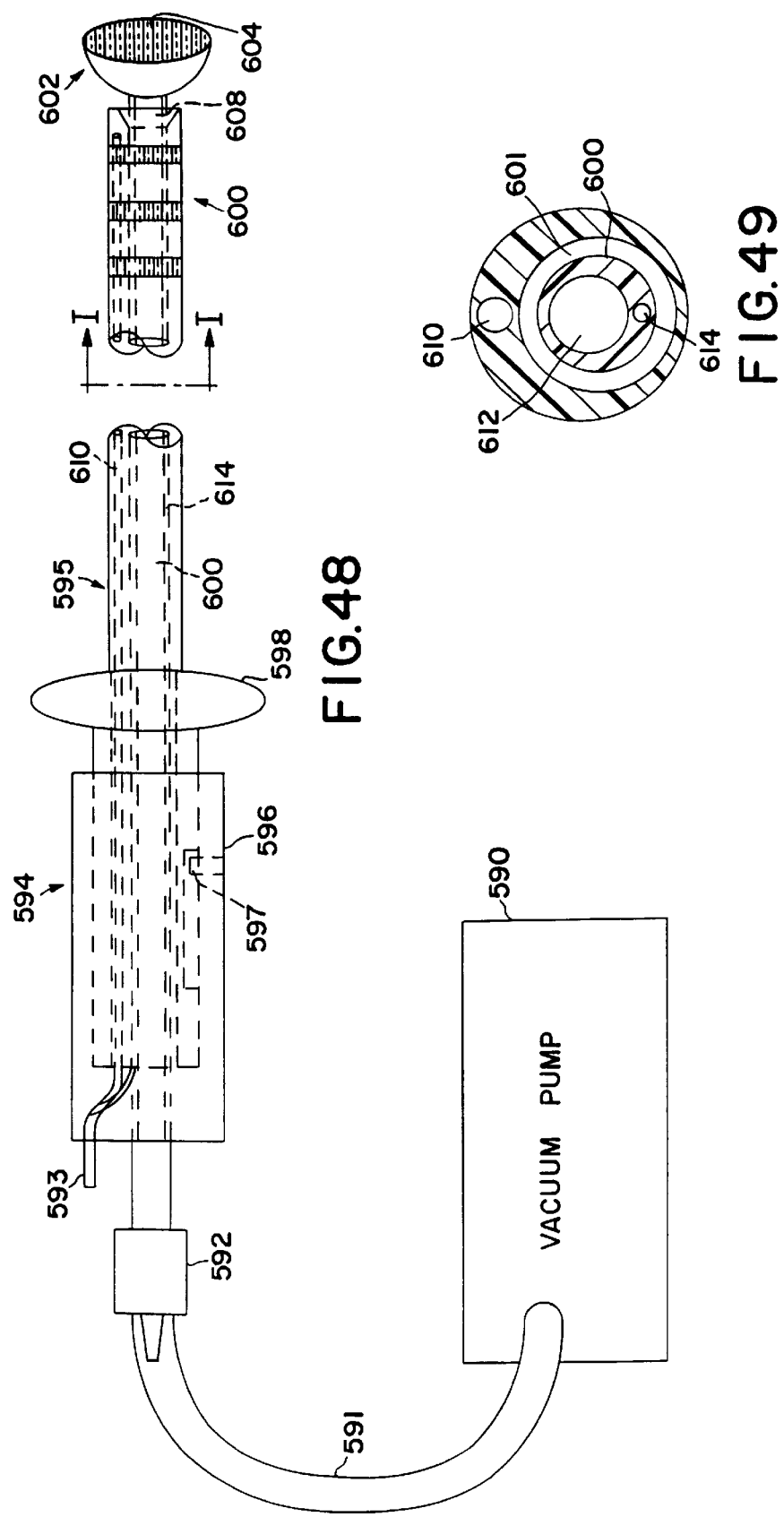

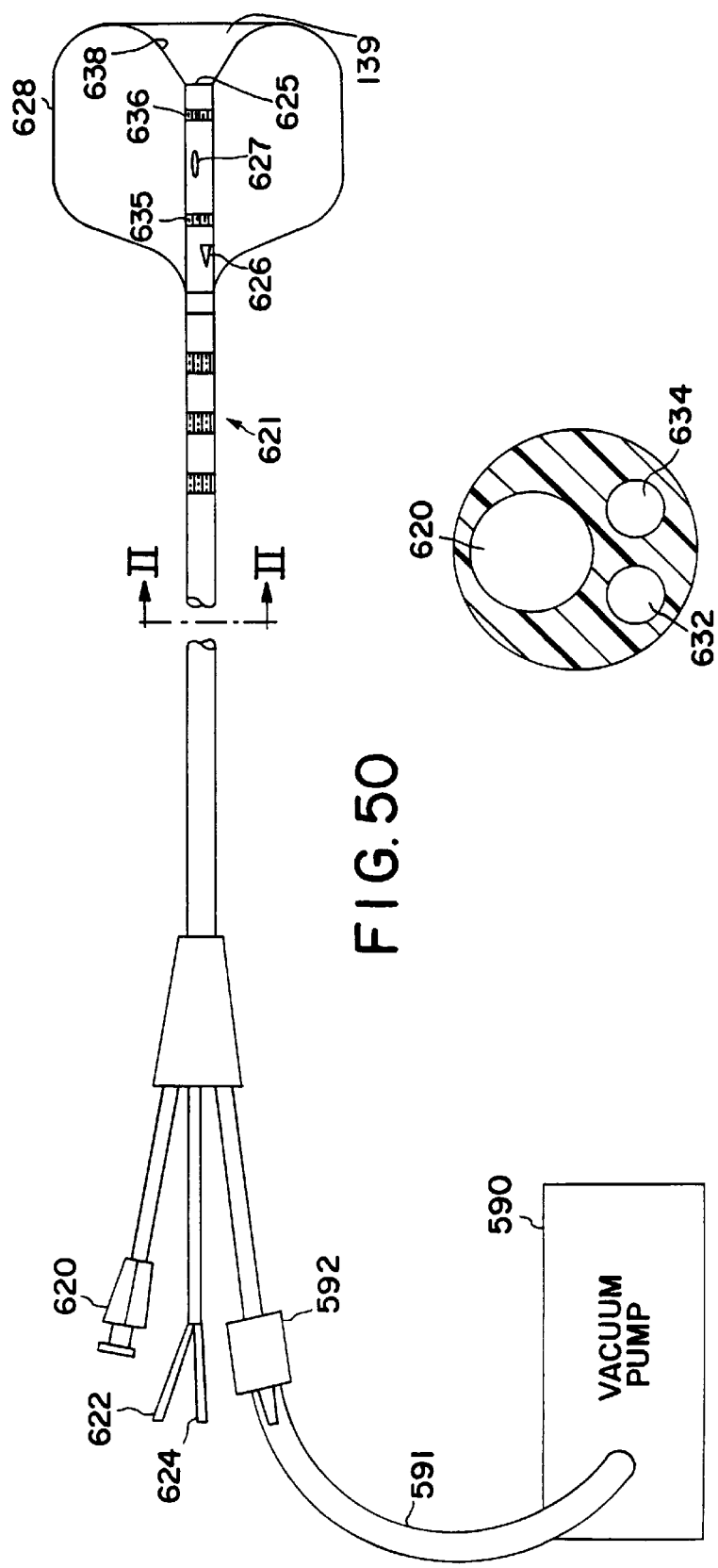

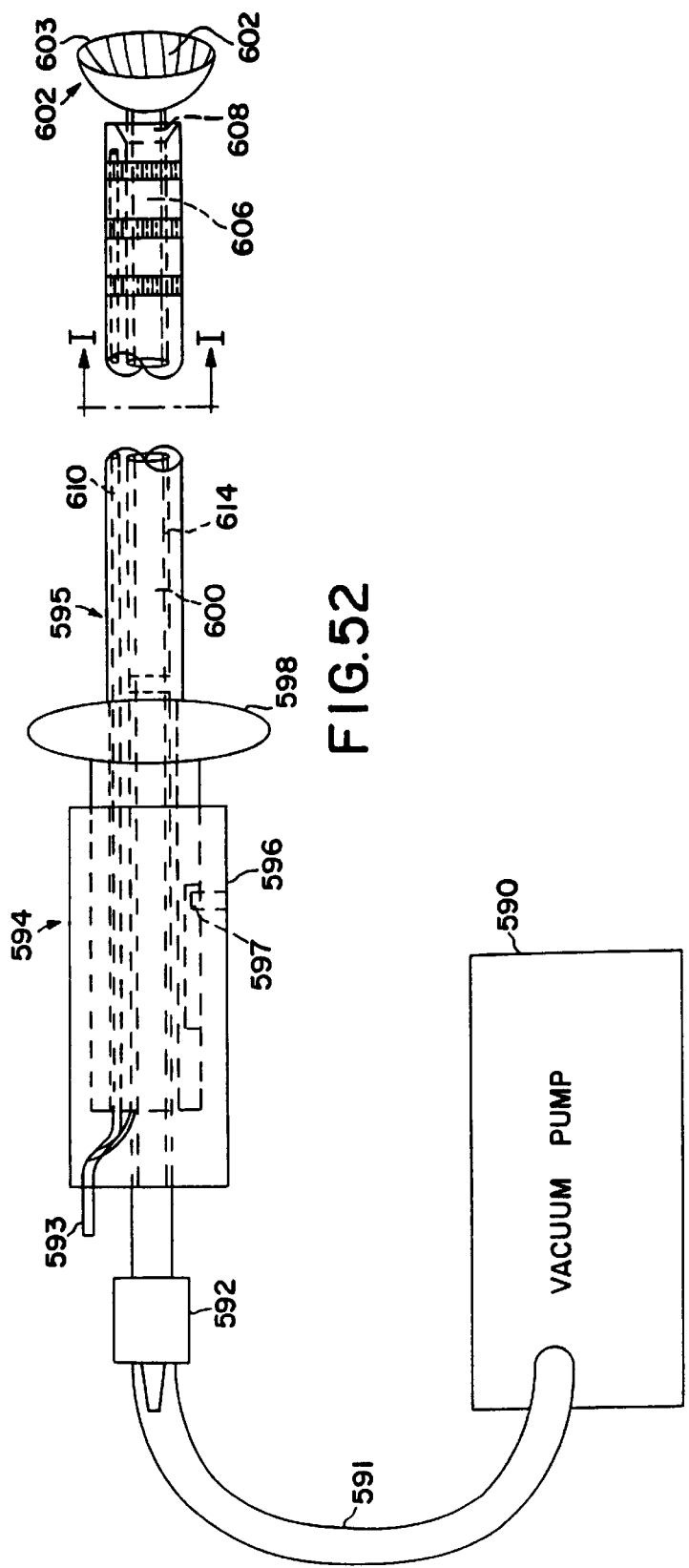

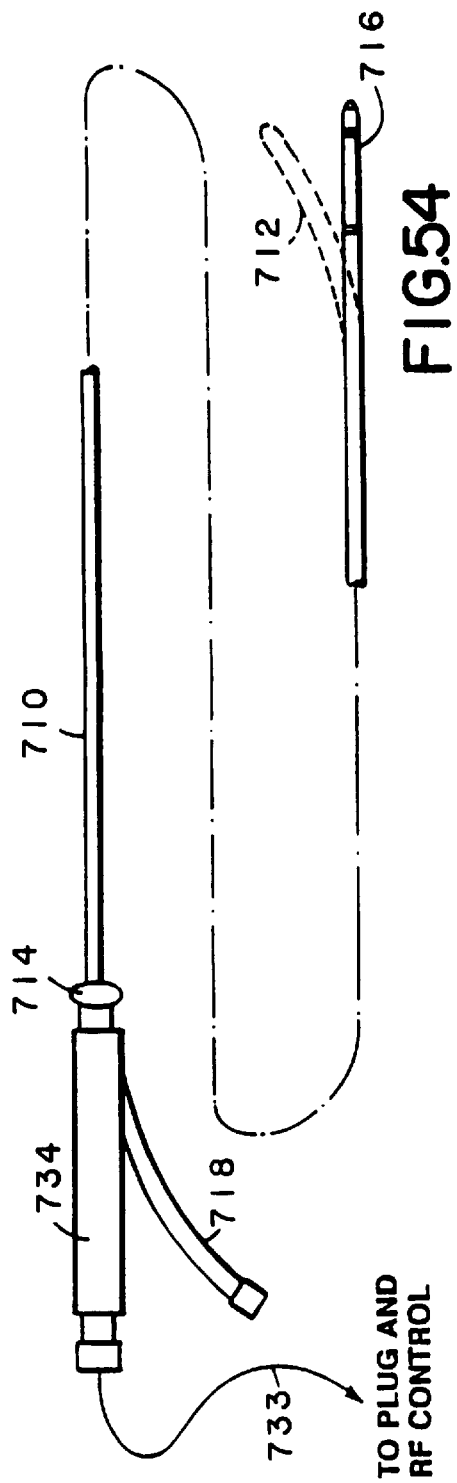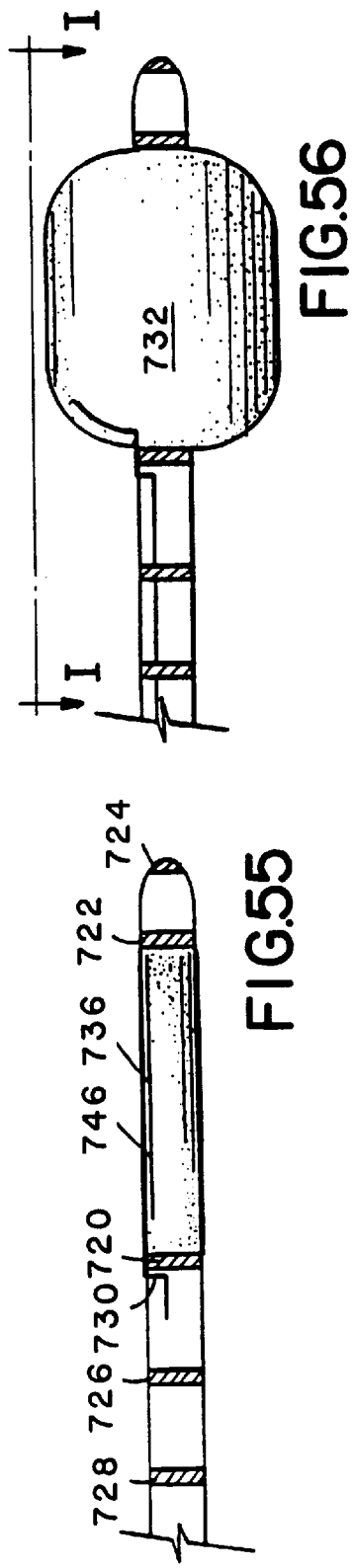

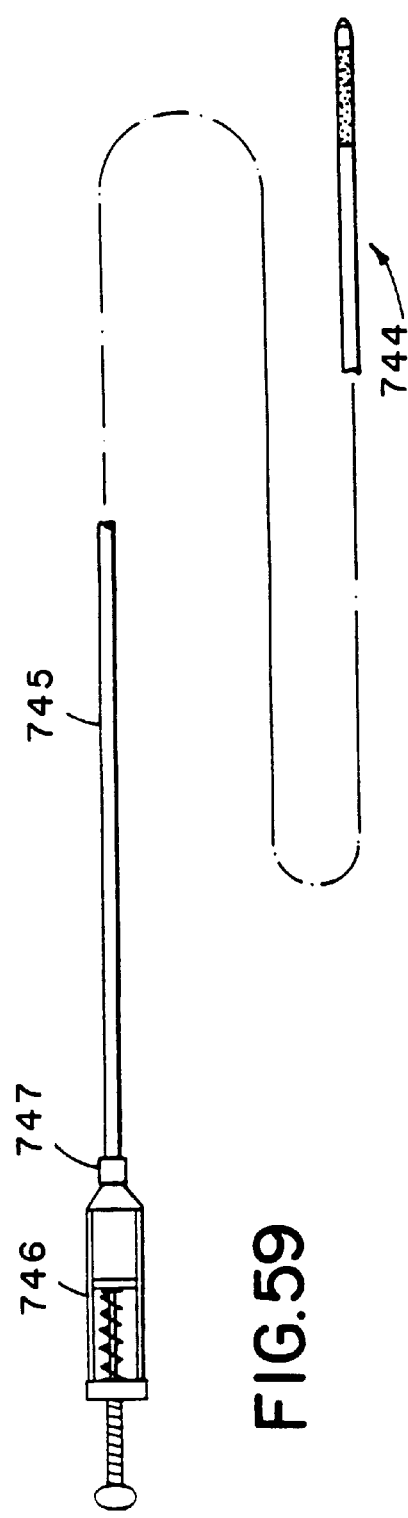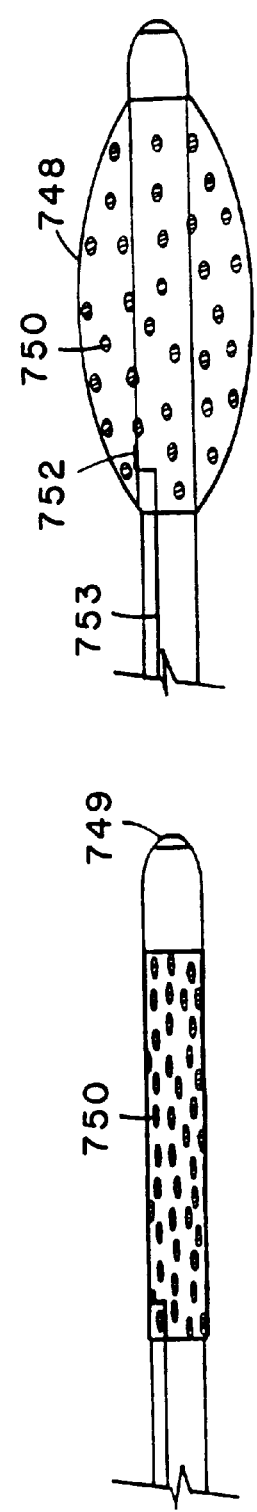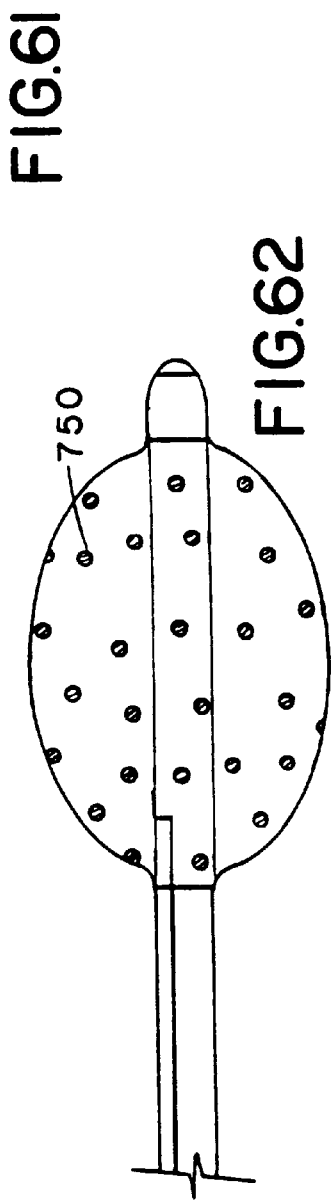

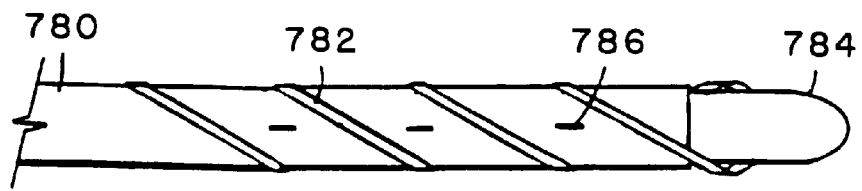
FIG.67
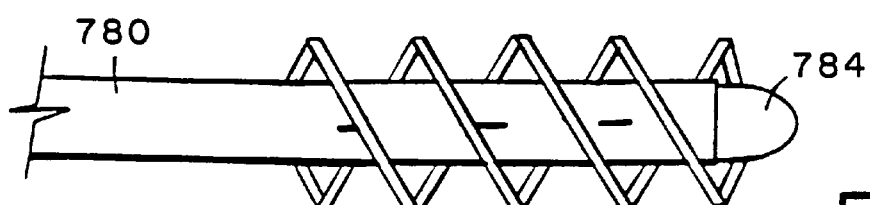
FIG.68
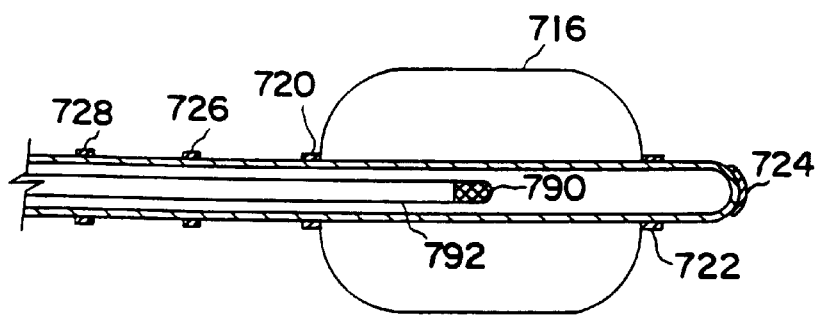
FIG.69
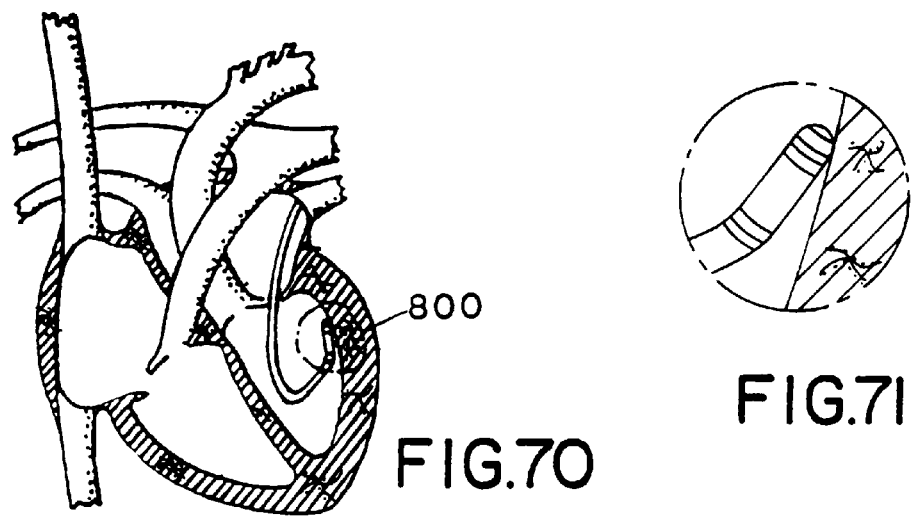
FIG.70
FIG.71

CATHETERS FOR IMAGING, SENSING ELECTRICAL POTENTIALS, AND ABLATING TISSUE

This application is a continuation-in-part of U.S. application Ser. No. 08/086,523, filed Jul. 1, 1993 and now abandoned, U.S. application Ser. No. 08/086,543 filed Jul. 1, 1993 and now abandoned, and U.S. application Ser. No. 08/086,740 now abandoned, all of which were filed on Jul. 1, 1993, and the entire disclosures of which are hereby incorporated herein by reference. The entire disclosures of U.S. Pat. No. 4,951,677 and U.S. Pat. No. 5,421,338 are also hereby incorporated herein by reference.

BACKGROUND OF THE INVENTION

The action of the human heart is controlled by propagation of electrical activity in various regions of the heart. The presence of abnormal accessory pathways in the heart can lead to conditions such as ventricular tachycardia and atrial flutter. These conditions are very common. Approximately 20% of the population will have some type of electrical disturbance activity in the heart during their lifetimes.

Physicians have found that they can detect malfunctions of the heart by probing the heart with a catheter fitted with one or more electrodes and having steering capability, measuring voltages within the heart, and observing the waveforms. Once a physician understands how the electrical activity of the heart is operating he can, if he wishes to do so, choose to "disconnect" certain portions of the heart electrically by the process of ablation. If multiple electrode are used, the catheter can make multiple readings simultaneously when it is curved inside the heart. Thus, the use of multiple electrodes shortens the time required to map the heart.

The electrical activity of the heart is detected and read in accordance with a mapping procedure to determine the presence of abnormal accessory pathways in the heart. A typical mapping procedure involves using electrophysiology sensing electrodes mounted on a catheter as remote-controlled voltage-testing probes to test various locations in the heart.

The process of ablation is a destructive process in which the catheter is used to burn a certain section of the heart which stops the propagation of an electrical signal from one portion of the heart to another. Alternate means to perform ablation have been to inject a chemical such as ethanol in specific regions of the heart, to apply very cold temperatures in a process called cryo-ablation, and to use sonic energy, which is sometimes referred to as ultrasonic ablation. The ablation process may alternatively consist of applying low-frequency RF energy to the heart tissue in order to create a burn. This burn will cause the tissue to heat up and desiccate and finally necrose.

Electrophysiology catheters are typically positioned at various positions in the heart under x-ray guidance. The x-rays show the catheter, and can also show the heart itself and thus the position of the catheter relative to the heart if dye injections are made. The clinician tries to visualize the position of the catheter in the heart in the various chambers. Electrical means are used to determine whether or not the electrode is in contact with the heart, and this information is shown on an EKG display. During the course of a typical procedure the operator will frequently return to one or more positions, and will look for particular waveforms that he sees from the sensing electrodes to determine whether the catheter has returned to the desired position. Typically, more than one catheter is used in a given procedure, and the catheters are constructed with steering or torquing devices that assist in positioning of the catheters within the heart.

The sensing or ablation electrodes of intracardiac catheters are typically made of tantalum, gold, or platinum. There can be as few as one or as many as five or more electrodes in a sensing and ablation catheter. Typical sensing and ablation catheters will have at least one tip electrode and two, three, or four ring electrodes proximal to the tip electrode. The proximal ring electrodes are typically spaced from the distal tip in two, three, or four-millimeter increments. The ring electrodes are generally bonded or crimped onto the catheter body or blended into the catheter body. The rings are sufficiently thick to have enough mechanical strength when crimped to adhere to the catheter shaft.

It is known that the injections of chemicals such as ethanol into the heart can produce a response which is similar to that produced when a burn is made in the heart. Basically, the injection of chemicals disrupts or cuts off electrical pathways in the heart by causing localized cell death.

The disorders that can be treated by ablating cardiac tissue include general arrhythmias, ventricular tachycardia, atrial fibrillation, atrial flutter, and Wolff-Parkinson-White Syndrome (WPW). Typically, ventricular tachycardia and WPW are treated by RF coagulation or DC discharge applied to cardiac tissue by electrode-tipped, deformable, and preset curved catheters. These catheters are of similar construction to those used in the art for electrically mapping the heart.

In order to navigate through the patient's vascular system, cardiac catheters are limited to small diameters. A typical mapping or ablation catheter has small electrodes mounted on the distal end of the catheter shaft. The electrodes can be arranged in bipolar pairs at the distal end of a catheter to ablate tissue by passing RF or DC electrical current between them through the surrounding myocardium. Alternatively, a single electrode could be disposed at the distal tip of a catheter, the single electrode being used to cause RF or DC electrical energy to pass directly through the heart tissue to a grounding plate on the surface of the patient's body.

Typically, the area of cardiac tissue that must be ablated is several times the size of the ablation region of the small electrode ablation catheters. Thus, a carpet bombing approach (i.e., ablating at many discrete sites) can be used to successfully treat cardiac disorders. This technique can lead to nonuniform ablation, as well as incomplete ablation if the ablation electrodes are not always directly in contact with myocardial tissue at each discrete site.

It is known to use a suction hole at a distal end of a catheter to engage tissue and thereby to hold the catheter in a fixed location in a patient's body while a distal ring electrode is placed in contact with tissue.

An alternative method for treating disorders in the heart is described in PCT application US93/09422, filed Oct. 4, 1993 by Daniel Bruce Fram et al. As described in that application, a catheter having a balloon mounted on its distal end is inserted into the coronary sinus or great cardiac vein. The balloon is inflated with fluid within the coronary sinus and is heated by a heating device located within the balloon. Tissue surrounding the coronary sinus is ablated by thermal conduction from the fluid to the tissue through the wall of the balloon.

Electrophysiological catheters can apply radio frequency energy to produce burn lesions at selected points in the heart to correct arrhythmias. By destroying the cells that constitute defective conductive pathways, the arrhythmias are stopped. Typically, rigid electrodes, of ring form either partially or totally surrounding the catheter shaft, are used, though it is desirable at times to produce larger lesions than can be produced with such electrodes. By using a larger electrode, one could apply higher power, and by spreading the current at conventional current intensity over a larger area, the larger lesion can be produced. The diameter of such conventional electrodes, however, has been limited by the size of access hole that can be tolerated in the artery. Also, the length of these electrodes has been limited by the need to maintain maneuverability for the catheter to pass through tight curves in proceeding through the arterial system and into the heart.

SUMMARY OF THE INVENTION

In one aspect, the invention features an acoustic imaging system for use within a body of a living being, having an elongated, flexible catheter constructed to be inserted into the body, an ultrasound device incorporated into the elongated, flexible catheter, and an electrode mounted on a distal portion of the elongated, flexible catheter. There are a plurality of electrical conductors extending from a proximal portion of the elongated, flexible catheter to the distal portion. At least two of the plurality of electrical conductors are connected to the ultrasound device and at least one of the plurality of electrical conductors is connected to the electrode. The ultrasound device is arranged to direct ultrasonic signals toward an internal structure within the body for the purpose of creating an ultrasonic image of the internal structure, and the electrode is arranged for electrical contact with the internal structure imaged by the ultrasound device.

The invention enables precise control and directability of catheters used in electrophysiology procedures, with the aid of high resolution images that reveal the cardiac anatomy and the location of the catheter and electrodes relative to the various chambers of the heart, the valves, the annuluses of the valves, and the other areas of the heart. Electrophysiology catheters according to the invention can be used without x-ray guidance, thereby eliminating dye injections and prolonged exposure of the patient and clinician to x-rays during the procedure. The clinician need not rely on his own imagination when trying to visualize the position of the catheter in the various chambers of the heart, and need not struggle to read an EKG display to determine whether an electrode is in contact with heart tissue. Thus, the invention reduces the time that it takes to obtain a reliable reading from a particular region of the heart that can be identified with ultrasound. Moreover, the physician need not look for particular waveforms from a sensing electrode to determine whether the electrode has returned to a desired position in the heart, and can reposition the electrode quickly and precisely. Also, by reducing the time required for electrophysiology sensing procedures and enhancing the precision with which an electrode can be positioned within the heart, the invention reduces the need for the catheter to include a large number of electrodes in order to reduce the time required to map the heart.

If the electrode is used for ablation, the on-catheter imaging also ensures that the electrode makes adequate contact with the endocardium, which is important because even if the catheter is in a position that is good enough to record the cardiac electrical activity it may not be good enough to deliver sufficient current to the portion of the heart requiring the ablation. There is no need to look at the impedance between the electrode and the heart itself to determine whether the electrode is in actual contact with the heart and there is no uncertainty as to whether the electrode is only in contact with blood, which of course is an electrical conductor and which would boil without creation of a lesion at all.

The invention also enables monitoring of the ablation process once it begins. The desiccation of tissue can be monitored by ultrasound, and it is useful to be able to see with ultrasound the depth and the extent of the lesion that is formed in the ablation procedure.

In another aspect, the invention features an acoustic imaging system for use within a body of a living being, having an elongated, flexible catheter, an ultrasound device incorporated into the elongated, flexible catheter, and a chemical ablation device mounted on a distal portion of the elongated, flexible catheter. The ultrasound device is arranged to direct ultrasonic signals toward an internal structure within the body of the living being for the purpose of creating an ultrasonic image of the internal structure, and the chemical ablation device is arranged to ablate at least a portion of the internal structure imaged by the ultrasound device by delivery of fluid to the internal structure.

By providing a mode of ablation that does not require electrophysiology sensing electrodes to be used also as ablation electrodes, the invention lowers the current delivery requirement for electrophysiology electrodes in electrophysiology catheters. I.e., an electrophysiology electrode used solely for sensing need not be as good an electrical conductor as an electrophysiology electrode that is also used for ablation.

Another aspect of the invention features an acoustic imaging system for use within a body of a living being, having an elongated, flexible catheter, an ultrasound device incorporated into the elongated, flexible catheter, and an ablation device comprising a transducer mounted on the distal portion of the elongated, flexible catheter. The ultrasound device is arranged to direct ultrasonic signals toward an internal structure within the body for the purpose of creating an ultrasonic image of the internal structure. The transducer is constructed arranged to convert electrical signals into radiation and to direct the radiation toward the internal structure within the body for the purpose of ablating tissue. The ablation device is arranged to ablate at least a portion of the internal structure imaged by the ultrasound device.

Another aspect of the invention features a catheter system that includes an elongated, flexible catheter, an imaging system, a data collection system, a central processing unit, and a graphic display system. The imaging system is constructed and arranged to provide information from which a graphical representation of an internal structure within the body may be created. The data collection system is at least partially located on a distal portion of the elongated, flexible catheter, and is constructed and arranged to produce a plurality of items of data corresponding to a respective plurality of locations within the internal structure. The central processing unit is electrically connected to the imaging system and the data collection system, and is configured and arranged to create the graphical representation of the internal structure from the information provided by the imaging system, and to super-impose onto the graphical representation the plurality of items of data provided by the data collection system. The plurality of items of data are super-imposed at locations on the graphical representation that represent the respective plurality of locations within the internal structure corresponding to the plurality of items of data. The graphic display system is electrically connected to the central processing unit, and is constructed to display the graphical representation onto which the plurality of items of data are super-imposed.

By super-imposing items of data on a graphical representation of an internal structure such as the heart, the invention provides an improved way to display in a meaningful and readily understandable manner the substantial information that is stored and saved in connection with a mapping procedure.

Another aspect of the invention features an acoustic imaging system for use within a body of a living being, having an elongated, flexible catheter, an ultrasound device incorporated into the elongated, flexible catheter, and at least one sonolucent, electrically conductive structure incorporated into the elongated, flexible catheter. In one embodiment the sonolucent structure is an electrode imprinted onto the catheter shaft as a thin film. The ultrasound device is arranged to direct ultrasonic signals through the sonolucent, electrically conductive structure toward an internal structure within the body for the purpose of creating an ultrasonic image of the internal structure.

By eliminating the thickness of ordinary metal ring electrodes bonded or crimped onto the body of a catheter, the invention enables an acoustic imaging electrophysiology catheter (capable of sensing, ablation, steering, and imaging) to have a profile that is small enough to permit easy access of several such catheters into the heart and to permit great maneuverability and flexibility of the catheters with minimal trauma to the patient. In particular, the ultrasound imaging device occupies considerable space in the assembly, and in order to make space for the ultrasound imaging device the electrical wires can be placed on the periphery of the catheter in accordance with the invention without adding substantially to the size of the catheter or interfering with imaging. The invention also allows an acoustic imaging electrophysiology catheter to be sufficiently flexible, because very thin traces do not add to the stiffness of the catheter in the way that individual wires sometimes do.

Another aspect of the invention features an ablation system for use within a body of a living being, having an elongated, flexible catheter, and an ablation device mounted on a distal portion of the elongated, flexible catheter, and a plurality of electrical conductors extending from a proximal portion of the elongated, flexible catheter to the distal portion. The ablation device includes a material that vibrates in response to electrical excitation, and the ablation device is constructed and arranged to cause ablation of at least a portion of an internal structure within the body. The ablation is at least assisted by vibration of the material.

Another aspect of the invention features a catheter system, having an elongated, flexible catheter, an acoustic imaging system constructed and arranged to direct ultrasonic signals toward an internal structure within the body for the purpose of creating an ultrasonic image of the internal structure, and constructed and arranged to provide the ultrasonic image, and an acoustic marker mounted on at least a distal portion of the elongated, flexible catheter. The acoustic marker is constructed to emit a sonic wave when the acoustic marker is electrically excited. The acoustic imaging system is constructed in a manner such that interference of the sonic wave emitted by the acoustic marker with the ultrasonic signals directed toward the internal structure by the acoustic imaging system causes an identifiable artifact to appear on the ultrasonic image of the internal body structure.

Another aspect of the invention features a method of ablating heart tissue. An elongated, flexible catheter is provided that has an ultrasound device and an ablation device incorporated into a distal portion thereof. The elongated, flexible catheter is inserted into a body of a living being, and the distal portion of the elongated, flexible catheter is introduced into the heart. The ultrasound device is positioned in the vicinity of an internal structure within the heart, and ultrasonic signals are directed from the ultrasound device toward the internal structure to create an ultrasonic image of the internal structure. The internal structure is ablated through use of the ablation device mounted on the distal portion of the elongated, flexible catheter.

In another aspect, the invention features a method of ablating heart tissue within a body of a living being. A balloon catheter is provided that includes a catheter shaft constructed for insertion into a blood vessel, an inflatable balloon mounted on a distal portion of the catheter shaft, and a heating device mounted on the distal portion of the catheter and arranged for heating tissue in contact with the balloon while the balloon is inflated. The catheter shaft and the balloon are sized and constructed to permit the distal portion of the catheter shaft to be inserted into an atrium or ventricle of a heart while the balloon is deflated. The distal portion of the catheter is positioned within the atrium or ventricle and adjacent to a wall of the atrium or ventricle. The balloon is inflated with fluid while the balloon is within the atrium or ventricle, and while the balloon is inflated it is engaged in direct contact with a wall of the atrium or ventricle. Tissue surrounding the balloon is heated through use of the heating device while the balloon is inflated.

The invention provides a large area of ablation in an atrium or ventricle of the heart, through direct contact of a relatively large ablation device with a wall of an atrium or ventricle. The balloon is preferably sufficiently deformable under stress to conform to the irregular shape of the various chambers of the heart. The deformability of the balloon also allows for a uniform ablation of cardiac tissue. In addition, the area of ablation can be controlled relatively easily by adjusting the pressure inside the balloon thereby, thereby adjusting the length of the balloon.

Another aspect of the invention features a cardiac ablation catheter constructed for insertion into a body of a living being. The cardiac ablation catheter includes a catheter shaft, an inflatable balloon mounted on a distal portion of the catheter shaft, a heating device mounted on the distal portion of the catheter shaft for heating tissue in contact with the balloon while the balloon is inflated, an electrode located on the distal portion of the catheter shaft, and a control circuit connected to the electrode and arranged to apply radio-frequency electrical current to the electrode for ablating tissue in contact with the electrode.

By combining together, in a single catheter, an ablation electrode at the distal tip of the catheter and a heated balloon, the invention provides for both discrete localized ablation of small areas of myocardium with the ablation electrode, as well as large area ablation with the heated balloon.

Another aspect of the invention features a cardiac ablation catheter that includes a catheter shaft constructed for insertion into a body of a living being, an inflatable balloon disposed annularly around a distal tip of the catheter shaft, a heating device mounted on a distal portion of the catheter shaft for heating tissue in contact with the balloon while the balloon is inflated, and an electrode located on the distal tip of the catheter for directly contacting tissue while the balloon is pressed against the tissue in an axial direction. The catheter shaft and balloon are sized and constructed to permit the distal portion of the catheter shaft to be inserted into the body while the balloon is deflated and to permit the balloon to be filled with a fluid inside the body.

The invention achieves the advantage of monitoring the ablation procedure with a single catheter by coupling the distal electrode to mapping circuitry. The distal electrode provides for sensing during ablation with the heated balloon, allowing for a highly controlled ablation procedure.

Another aspect of the invention features an ablation catheter that includes a catheter shaft constructed for insertion into a body of a living being and having a lumen extending longitudinally through it for coupling a proximal source of suction to a distal port located at the distal tip of the catheter, an electrode mounted on the distal portion of the catheter shaft, and a tissue-engagement device surrounding the distal port and constructed to engage tissue with suction when the port is placed adjacent to the tissue. The tissue-engagement device is constructed to cause the distal portion of the catheter shaft to be held in a fixed position relative to the tissue while the electrode is placed in contact with an internal body structure. In certain preferred embodiments, the electrode is mounted directly on the tissue-engagement device or is adjacent thereto.

By combining, on a single catheter, a tissue-engagement device with an ablation electrode, the invention reduces the likelihood of the electrode being moved from an identified ablation site, which could result in damage to normal tissue. In addition, the invention provides a means for assuring that the electrode remains in direct contact with the tissue to be ablated or mapped, especially if the electrode is mounted directly on the tissue-engagement device itself or adjacent thereto, thereby reducing the likelihood of insufficient ablation or poor mapping due to the electrode not being in contact with the tissue.

Another aspect of the present invention provides a catheter with an expandable ablation electrode constructed to access the heart. When it is introduced to the heart, the electrode is small and suitably flexible to maneuver through the torturous path. However, when the catheter is in place in the heart, the electrode is expansible in diameter to a substantially larger dimension, and is relatively rigid, enabling a large conductive surface to press against the heart tissue with the desired contact pressure. When RF energy is then applied to the electrode it produces a burn lesion of desired large size and depth. This overcomes the limitations to size that have been encountered using conventional rigid electrodes.

According to one preferred embodiment, there is provided on the electrophysiology catheter, a balloon the exterior of which is coated uniformly with a conductive material, preferably gold, or other material that is both electrically and thermally conductive. Such conductive coating materials can be deposited on the surface of the material forming the balloon, by conventional vacuum deposition techniques, or a thicker coating of gold for larger current capacity can be produced with electroplating techniques.

Substantial thermal conductivity of the electrode material is important to prevent heat build-up in the electrode which might cause sticking of the electrode to tissue, or if the temperature gets high enough, even cause the thin electrode layer to deteriorate.

In preferred embodiments, a balloon of the type commonly used for balloon angioplasty dilatation, is employed. Such a balloon is made of a very strong, low elongation resinous material such as PET (polyethylene terepthalate). As is known, PET can be formed into a balloon of thin wall thickness using modified bottle blowing techniques. Such a balloon, in uninflated state, is folded about the catheter using folding techniques commonly applied to dilatation balloons to achieve the size corresponding substantially to that of the catheter on which it is mounted.

The dimension of the balloon is enlarged during use by infusing into the balloon fluid containing a significant concentration of radiopaque contrast agent such as the conventional viscous inflation fluid used for balloon dilatation. Inflation causes the balloon to unfold and to expand to its set, relatively large diameter. By inflating to high pressure, e.g. 5 or more atmospheres, the enlarged balloon becomes significantly rigid.

Typically, the balloon is of a set length, which may be substantially longer than conventional rigid electrodes. When in deflated condition, at its smaller dimension, it and the portion of the catheter on which it is carried is sufficiently flexible to enable maneuvering through the tight bends of the arterial system and into the heart. Upon inflation, the rigidity of the expanded, pressurized balloon is realized to be appropriate for effective RF ablation.

A degree of rigidity is an important requirement because the electrode must push against the heart tissue with pressure to cause the heart tissue to conform to the electrode shape and establish good, uniform electrical contact. The degree of conformity and the uniformity of pressure along the length of the balloon is facilitated in the present invention by operation of Pascal's law, which enables pressure against the tissue to be equilibrated.

In the case of balloons comprised of PET, a power supply conductor is attached to the conductive coating at the proximal or rearward end of the balloon, on the exterior surface. The conductor such as a wire, is lead through the wall of the catheter and through the shaft to appropriate terminal at the proximal end.

In another embodiment, the balloon is made of more compliant material than PET. In one case, advantageous for certain purposes, the balloon is comprised of an elastomer. Due to its elasticity, one cannot only change the diameter from small to large, but one can chose the particular inflated dimension over a range by careful metering of the inflation fluid into the balloon. Thus there is achievable an electrode having an inflated dimension that may be selected from between e.g. 5 mm and 10 mm, depending on the size of the lesion the physician desires to create. This provides to the user the option, after introduction of the catheter of, establishing a first electrode shape, and size of the lesion to be produced, by introducing a preselected volume of fluid. Typically the operating physician may choose to produce the smallest region possible that in his judgment may cure the arrhythmia. Therefore he may initially start with the balloon inflated to 5 mm, and only increase its size if deeper and larger lesions are found to be necessary. The balloon size can be increased by metered addition of additional inflation fluid.

For the purpose of controlling the size of the inflation of the expansible balloon, a high accuracy screw syringe is employed to precisely control the amount of fluid introduced to the balloon. The type of screw syringe used for balloon angioplasty is suitable for this purpose.

The balloon can be seen on the fluoroscope due to the contrast agent in the inflation fluid, and its size can be fluoroscopically judged. Thus one can control the diameter with the amount of fluid introduced and one can monitor its size fluoroscopically.

In the case of the elastomeric, variable sized balloon, in order to allow the balloon to expand and contract, the electrode coating on the outside of the balloon, is of a pattern chosen to enable the balloon to stretch. In one case it may be a serpentine pattern of narrow conductive elastomeric stripes on the balloon surface that effectively hinge while maintaining continuity as the balloon expands, to accommodate the change in geometry. In another embodiment a series of metal conductive dots is applied to the exterior of the balloon, while flexible, narrow conductive paths may be defined to introduce power to the dot-shaped electrodes.

Another technique for introducing energy to the dots may be by capacitive coupling. In this case, electrically conductive fluid is employed as the inflation medium for the balloon. Monopolar RF energy is applied to the fluid via an electrode fixed to the exterior of the portion of the catheter shaft that extends through the balloon, and capacitive coupling occurs across the thickness of the balloon to the conductive coated dots on the outside of the balloon.

Instruments described so far are intended for monopolar operation. There is typically only one electrode on the catheter and the current is conducted through the tissue to another electrode in the form of a ground plate that has a surface area many times that of the catheter electrode. This ground plate is maintained in contact with the skin of the patient. Because of the large size of the ground plate, when the current reaches it, the density is so low that no burning or heating occurs, as is well known.

In certain instances, however, the balloon is advantageously constructed for bipolar introduction of RF current to the tissue. This can be advantageous for cases where one wishes to create a large area lesion but not cause deep penetration. This may be useful in the case of diseased arrhythmia producing tissue that lies only near the surface.

In one preferred embodiment, a balloon has two annular bands of conductive material on its exterior for bipolar operation, with the RF current flowing through the tissue between the two bands.

Other ways to construct the balloon will occur to those skilled in the art. For instance, a balloon may be of electrically conductive material such as conductive elastomer filled with silver particles.

Other examples of operable, expansible electrodes include mechanical structures.

The first preferred mechanical device is comprised of a series of expansible members that are constrained either by spring force or mechanical force so that when they are uncovered, in the manner of a conventional stone retrieval basket sold by Boston Scientific Corporation, the wire ribbons expand outward and provide a larger electrode surface for engagement of the tissue with suitable pressure.

In one instance a straight cage formed of spring wires that are generally axially disposed is employed. It is so constructed that when the wires are released by removal of the sheath, they are allowed to expand to a rest dimension of generally spherical shape. Self-expanding wires may be constructed of conductive spring metal or a relatively poor conductor with good spring properties can be employed such as nitinol on which is deposited a highly conductive material such as gold. For such a self-expanding embodiment, as mentioned, a constraining sheath is employed. It confines the springy wires in distorted condition at a much smaller diameter. Upon removal of the sheath, such as sliding it proximally of the catheter, the spring wires are released to form the rounded shape.

In another embodiment, a tension wire can be employed which acts to pull the wires of the basket structure radially inwardly to keep the wires close to the shaft during introduction. Release of tension on the tensioning wire enables the structure to expand radially to its enlarged rest condition.

In another embodiment, a central member independent of the outer catheter wall is employed to move the distal tip of the spring basket distally independently of the proximal end, to reduce the diameter of the basket by pulling it axially. Release allows the distal tip to draw back and the electrode basket to expand.

Other variations of this aspect are a spiral cage and a braided weave each made of heat conductive, electrically conductive wires. These again are embodiments in which the wire members lie close to the shaft in the reduced sized state and expand to the larger diameter in the released or expanded state. Such more complex structures are preferable in cases where it is desired to maximize the wire contact coverage when the basket is expanded.

In many instances use of the balloon is preferred to obtain the most uniform distribution of energy, but there are instances in which the mechanical structures have advantage, such as for conforming to special profiles of particular locations of the heart cavity.

In certain embodiments, a further electrode is disposed on the portion of the shaft that protrudes beyond the balloon. Such an electrode can be used for producing small area ablation, when desired, to increase the capability of the single catheter. The distal electrode may also be employed, along with additional electrodes, for instance, ring electrodes on the catheter shaft both proximal and distal of the balloon, for electrophysiological mapping. In some cases, it is preferred to activate the mapping electrodes simultaneously while performing ablation. In this way, the change in the electrical activity of the adjacent tissue can be monitored as ablation proceeds, thus to produce an indication monitoring of the result being produced. Control of the duration of the application of the RF current may be determined by the detected values.

It is also advantageous in certain instances to employ ultrasound imaging in connection with the ablation technique to observe the lesion forming and to measure its dimension.

In certain instances, it is advantageous to provide a fluid dispensing lumen as part of the catheter for the purpose of augmenting the ablation effect at the tissue. The fluid may be selected to be highly electrically conductive relative to the conductivity of blood and thus can render the zone where the fluid is introduced preferentially conductive, to establish a zone that tends to concentrate the heat, as a result of $I^2R$ losses being greatest where the largest current flows.

In another instance, fluid introduced through the lumen is selected to be destructive of tissue, such as alcohol which tends to be ablative due to its osmotic behavior. In this way fluid ablation and RF ablation effects can be advantageously combined.

In preferred embodiments, the catheter is of 7 French size. The balloon in deflated condition in this case is also about 7 French and is expansible to e.g. 5 or 10 mm in diameter.

A principal advantage of the invention is that it enables larger lesions to be created with a single catheter to achieve a definitive result for the patient in less time, hence with less risk to the patient and better utilization of the physician's time, than with prior electrodes.

Thus advantages of the present invention are that quite large electrodes can be achieved which act faster and can produce lesions deeper than prior devices, all in a device that is practical to maneuver through the arterial system and into the heart. The instrument is useful in any chamber of the heart where it is desired to produce a large lesion.

Numerous other features, objects and advantages of the invention will become apparent from the following detailed description when read in combination with the accompanying drawings.

BRIEF DESCRIPTION OF THE DRAWINGS

FIG. 4 is a longitudinal, cross-sectional view of the distal end of the assembled acoustic catheter.

FIG. 5 is a longitudinal sectional view of the transducer element of the catheter on a greatly magnified scale.

FIG. 6 is a diagrammatic representation of sound waves emanating from the acoustic lens of the catheter.

FIG. 8a is a cross-sectional view on an enlarged scale of a portion of FIG. 8.

FIG. 19 is a longitudinal view of a catheter sheath having a balloon in combination with an electrode for electrophysiology or cardiac ablation, and FIGS. 19a, 19b and 19c are longitudinal views of the distal portion of the catheter sheath shown in FIG. 19, illustrating stages of inflation of the balloon.

FIG. 20 is a partially cut-away longitudinal view of a catheter sheath having a balloon on which a set of electrodes is coated, the balloon being constructed of electrically excitable material and having a set of perfusion ports in its wall.

FIG. 21 is a partially cut-away longitudinal view of a catheter sheath having a balloon through which a fluid-injection needle passes, the balloon being constructed of electrically excitable material and having a set of perfusion ports in its wall.

FIG. 21a is an enlarged view, partially in cross-section of the fluid-injection needle shown in FIG. 21 exiting through a wall of the balloon.

FIG. 48 is a side view of a catheter having a suction cup at its distal end.

FIG. 49 is a sectional view of the catheter of FIG. 48 taken along line I—I in FIG. 48.

FIG. 50 is a side view of a catheter having an inflated balloon at its distal end that performs a suction anchoring function.

FIG. 51 is a sectional view of the catheter of FIG. 50 taken along line II—II in FIG. 50.

FIG. 52 is a side view of a catheter having a suction cup at its distal end.

FIG. 54 is a schematic view of an electrophysiological heart catheter.

FIG. 55 is a side view of a distal portion of the electrophysiological heart catheter of FIG. 54, having a deflated balloon.

FIG. 56 is a side view of a distal portion of the electrophysiological heart catheter of FIG. 54, having an inflated balloon.

FIG. 59 is a schematic view of an electrophysiological heart catheter coupled to an inflation metering device.

FIG. 60 is a side view of a distal portion of the electrophysiological heart catheter of FIG. 59, showing a deflated balloon having a plurality of conductive dots mounted on its surface.

FIG. 61 is a side view of the distal portion of the electrophysiological heart catheter of FIG. 59, showing the balloon partially inflated.

FIG. 62 is a side view of the distal portion of the electrophysiological heart catheter of FIG. 59, showing the balloon more fully inflated.

FIG. 67 is a side view of a distal portion of an electrophysiological heart catheter shaft having a set of flexible members wrapped tightly around the catheter shaft.

FIG. 68 is a side view of the electrophysiological heart catheter shaft of FIG. 67, showing the flexible members expanded away from the catheter shaft.

FIG. 69 is a partially sectional view of the distal portion of a catheter of the type shown in FIG. 56 that additionally includes an ultrasound transducer.

FIG. 70 is a partially cross-sectional view of a catheter in the left side of a heart, showing a balloon electrode in a deflated condition and in contact with heart tissue.

FIG. 71 is an enlarged view of a portion of FIG. 70.

DETAILED DESCRIPTION

General Structure

Figure 1:
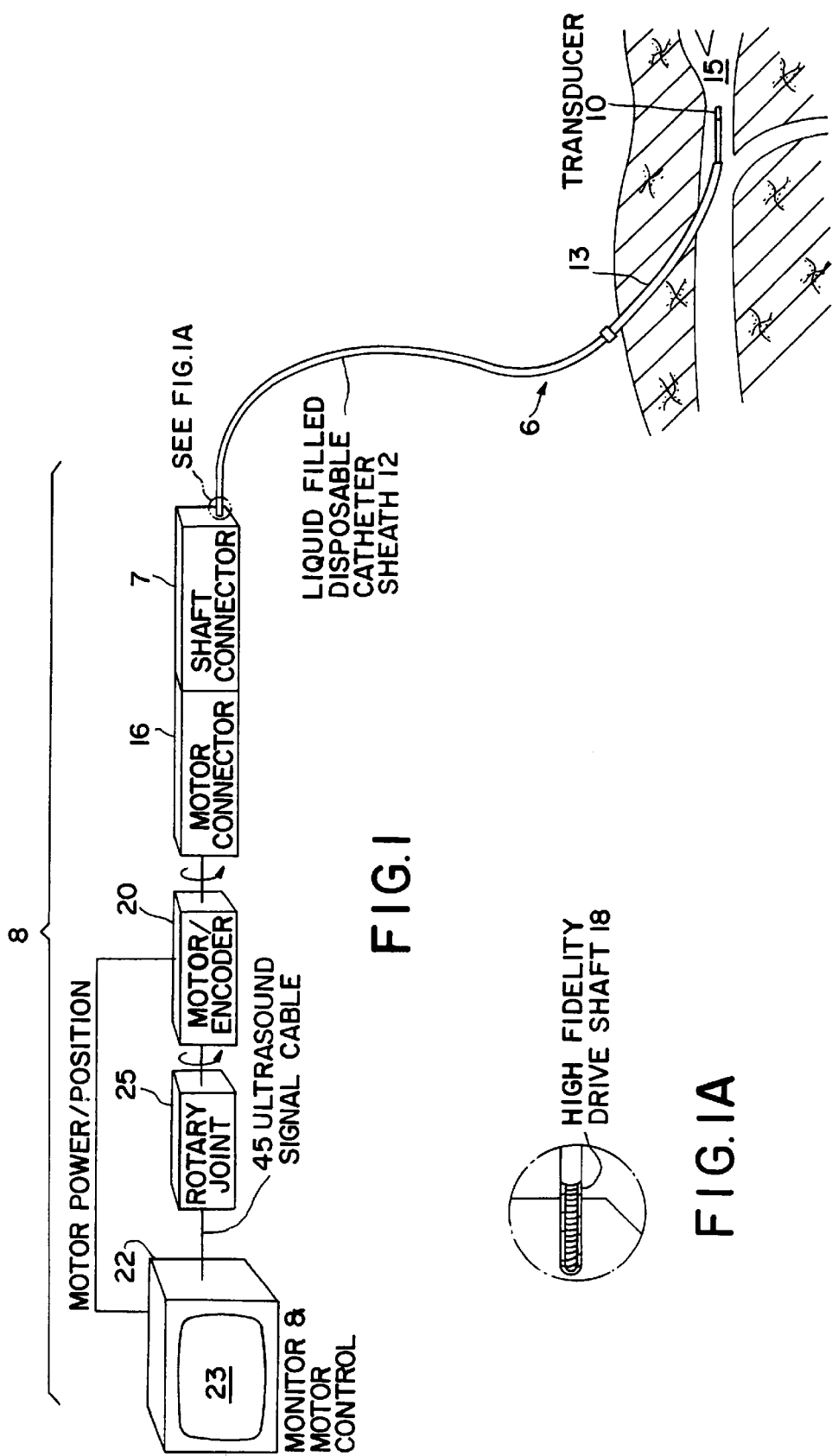
FIG. 1 is a schematic diagram of a system showing use of an acoustic catheter.

Referring to FIG. 1, a micro-acoustic imaging catheter 6 according to the invention is driven and monitored by a control system 8. The catheter is comprised of a disposable catheter sheath 12 (FIGS. 2 and 4) having a sound-transparent distal window 24 provided by dome element 25 (FIG. 4), in which is disposed a miniature, rotatable ultrasonic transducer 10 (FIGS. 3 and 4) driven by a special, high fidelity flexible drive shaft 18. A relatively rigid connector 11 is joined to the proximal end of the main body of the catheter sheath, adapted to be joined to a mating connector of drive and control system 8.

The catheter is adapted to be positioned within the heart by standard catheter procedures by guiding the flexible catheter through various blood vessels along a circuitous path, starting, for example, by percutaneous introduction through an introducer sheath 13 disposed in a perforation of the femoral artery 15.

Figure 2:
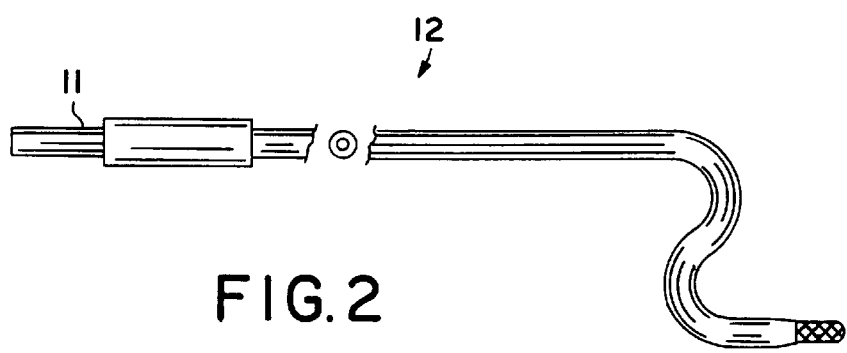
FIG. 2 is a side view of a disposable catheter sheath for the acoustic catheter.

Referring to FIG. 2, disposable catheter sheath 12 is a long tube, extruded from standard catheter materials, here nylon, e.g. with outer diameter, D, of 2 mm, wall thickness of 0.25 mm and length of 1 meter. Dome element 25, connected to the distal end of the tube, is a semi-spherically-ended cylindrical transducer cover constructed of material which is transparent to sound waves, here high impact polystyrene. This dome element has a thickness of approximately 0.125 mm and a length E of about 8 mm. For purposes described later herein, catheter sheath 12 in its distal region preferably tapers down over region R as shown in FIG. 4 to a narrowed diameter D' at its distal end, achieved by controlled heating and drawing of this portion of the original tube from which the sheath is formed. Catheter sheath 12 and acoustically transparent dome element 25 are adhesively bonded together.

Figure 3:
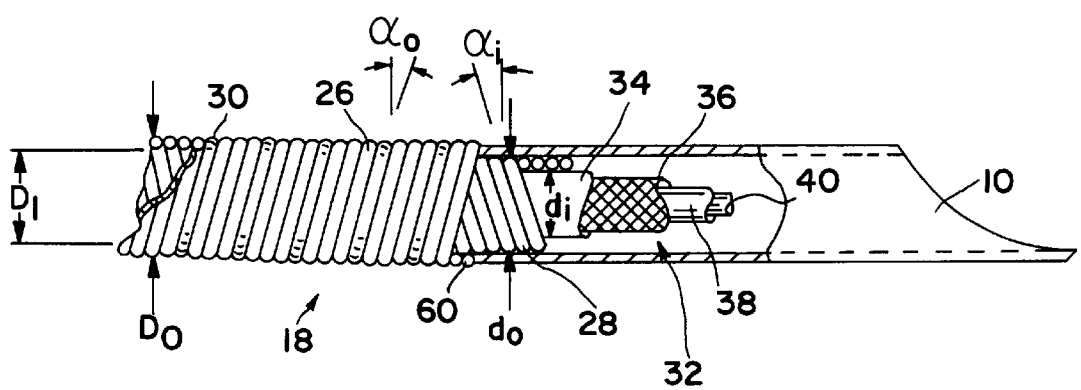
FIG. 3 is a longitudinal, partially cut away view of the distal end of the rotating assembly of the acoustic catheter.

Referring to FIGS. 3 and 4, the drive shaft assembly 18 is formed of a pair of closely wound multi-filar coils 26, 28 wound in opposite helical directions. These coils are each formed of four circular cross-sectional wires, one of which, 30, is shown by shading. Coils 26, 28 are soldered together at both the distal and proximal ends of the assembly in interference contact, here under rotational pre-stress. By also providing a pitch angle of greater than about 20°, a substantial part of the stress applied to the wire filaments of the coil is compression or tension in the direction of the axis of the filaments, with attendant reduction of bending tendencies that can affect fidelity of movement. There is also provision to apply a torsional load to the distal end of the assembly to cause the drive shaft to operate in the torsionally stiff region of its torsional spring constant curve, achieved by viscous drag applied to the rotating assembly by liquid filling the narrowed distal end of the catheter sheath (FIG. 4). Such loading, together with initial tight association of the closely wound filaments in the concentric coils, provides the assembly with a particularly high torsional spring constant when twisted in a predetermined direction. Thus, despite its lateral flexibility, needed for negotiating tortuous passages, the assembly provides such a torsionally stiff and accurate drive shaft that rotary position information for the distal end can, with considerable accuracy, be derived from measurement at the proximal end of the drive shaft, enabling high quality real-time images to be produced. Further description of the coils of the drive shaft and their condition of operation is provided below.

Coaxial cable 32 within coils 26, 28 has low power loss and comprises an outer insulator layer 34, a braided shield 36, a second insulator layer 38, and a center conductor 40. Shield 36 and center conductor 40 are electrically connected by wires 42, 44 (FIG. 5) to piezoelectric crystal 46 and electrically conductive, acoustical backing 48 respectively, of the transducer. Helical coils 26, 28, especially when covered with a highly conductive metal layer, act as an additional electric shield around cable 32.

Transducer crystal 46 is formed in known manner of one of a family of ceramic materials, such as barium titanates, lead zirconate titanates, lead metaniobates, and PVDFs, that is capable of transforming pressure distortions on its surface to electrical voltages and vice versa. Transducer assembly 10 is further provided with an acoustic lens 52. The radius of curvature B of lens surface 52 is greater than about 2.5 mm, chosen to provide focus over the range f (FIG. 6) between about 2 to 7 mm. The lens is positioned at an acute angle to the longitudinal axis of the catheter so that, during rotation, it scans a conical surface from the transducing tip, the angle preferably being between 10° and 80°, e.g., 30°. Transducer backing 48 is acoustically matched to the transducer element to improve axial resolution.

The transducer assembly 10 is supported at the distal end of the drive shaft by a tubular sleeve 29 which is telescopically received over a distal extension of the inner coil 28, as shown in FIG. 3.

Referring again to FIG. 4, the length, E, of dome element 25 is sufficient to provide headroom F for longitudinal movement of transducer 10 within the dome element as catheter sheath 12 and coils 26, 28 are twisted along the blood vessels of the body. In the untwisted state, transducer 10 is a distance F, about 2 to 3 mm, from the internal end surface of the dome element 25. The dome element, along with catheter sheath 12 is adapted to be filled with lubricating and sound-transmitting fluid.

Figure 7D:
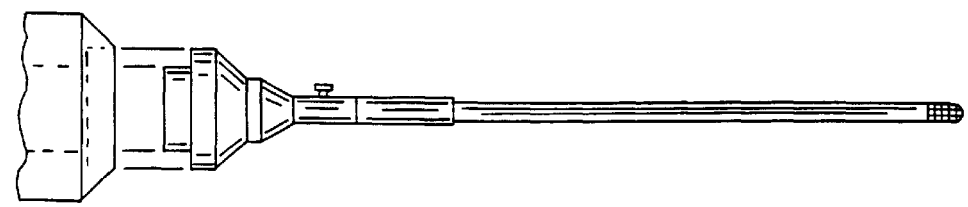
FIGS. 7–7d are longitudinal views of a catheter assembly illustrating steps in filling the sheath and assembling the acoustic catheter, the syringes shown in the figures being on a reduced scale.
Figure 7C:
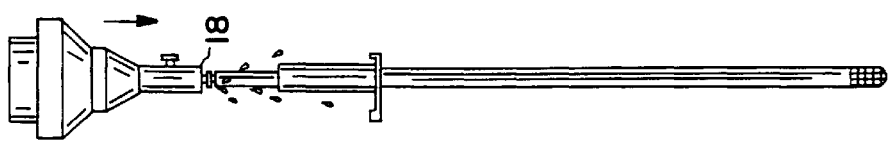
Figure 7B:
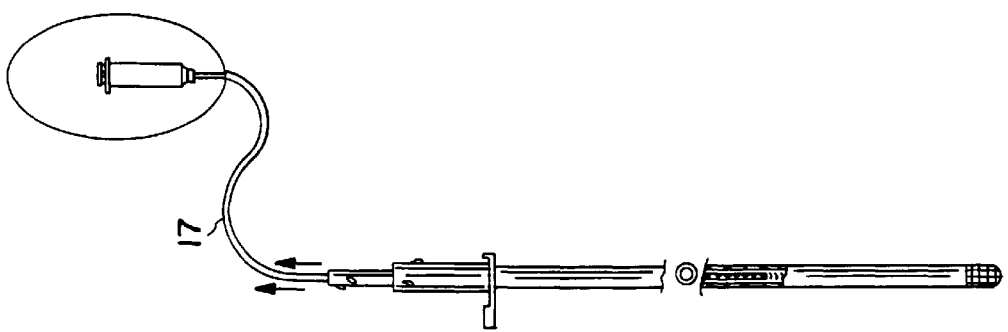
Figure 7A:
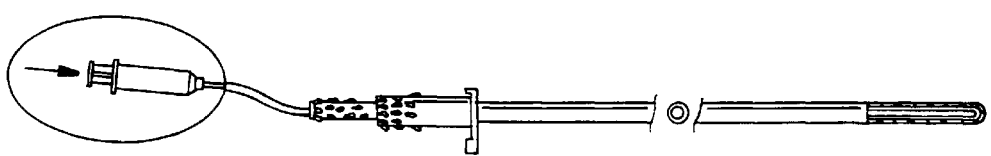
Figure 7:
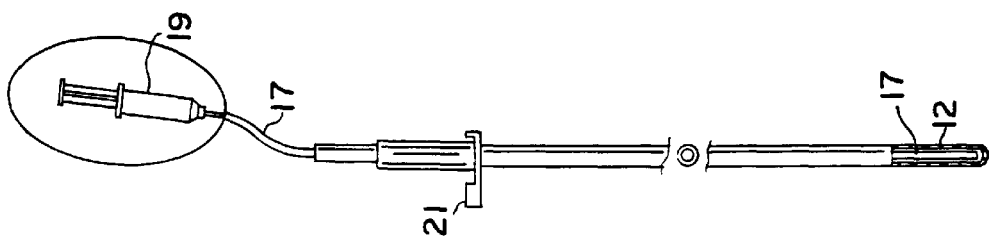

FIGS. 7–7b show the filling procedure used to prepare ultrasound catheter sheath 12 (or any of the other interchangeable sheaths described below) for attachment to the ultrasound imaging drive shaft and transducer assembly. A sterile, flexible filling tube 17 attached to a syringe 19 is filled with sterile water. This filling catheter is inserted into the ultrasound catheter sheath 12, all the way to the distal tip. The water is then injected until it completely fills and the excess spills out of the ultrasound catheter while held in a vertical position, see FIG. 7a. This expels air from the catheter which could impair good acoustic imaging. Continued pressure on the plunger of the syringe causes the flexible tube 17 to be pushed upward, out of catheter 12, FIG. 7b, leaving no air gaps behind. This eliminates the necessity to carefully withdraw the flexible filling tube at a controlled rate which could be subject to error. A holding bracket 21 is used to hold the catheter vertical during this procedure.

After the catheter sheath 12 is filled, the acoustic transducer 10 and shaft 18 are inserted, displacing water from the sheath 12, until the installed position, FIG. 7d, is achieved.

Figure 8:
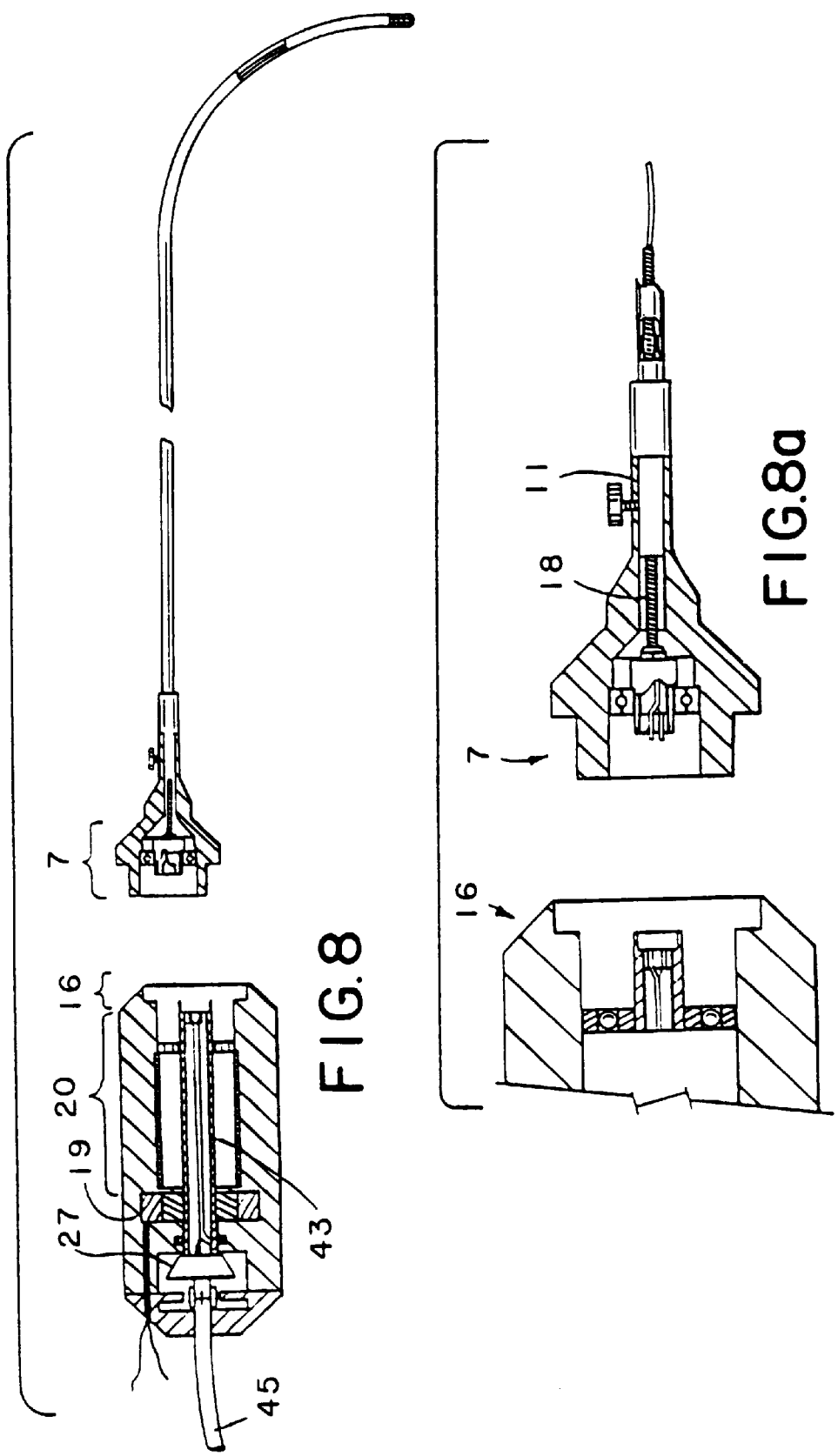
FIG. 8 is a cross-sectional view of the motor-connector assembly to which the catheter is connected.

FIGS. 8 and 8a (and FIG. 1, diagrammatically) show the interconnection arrangement for a connector 7 at proximal end of the acoustic catheter with connector 16 of the driving motor 20, and the path of the electric wires through the center shaft 43 of the driving motor. The center shaft and connector 16 rotate together, as do the wires that pass through the hollow motor shaft. The latter connect to a rotating electrical joint 27, which is held stationary at the back end and is connected to stationary coaxial cable 45 through a suitable connector such as a common BNC type. The enlarged view shows how the motor connector 16 and the driveshaft connector 7 mate when the two assemblies are pushed together, thereby making both electrical and mechanical contact. The catheter connector 7 is held in position by an ordinary ball bearing which provides a thrusting surface for the rotating connector 16 and driveshaft 18 while allowing free rotation. The disposable catheter sheath 12 includes an inexpensive, relatively rigid hollow bushing 11 of cylindrical construction that allows it to be slid into and held by means of a set screw in the housing that captures the non-disposable bearing, connector and driveshaft 18. The longitudinal and rotational position of hollow bushing 11 relative to the housing is adjustable. Drive shaft coil assembly 18, thus attached at its proximal end to connector 16 of drive motor 20, rotates transducer 10 at speeds of about 1800 rpm. The transducer 10 is electrically connected by coaxial cable 32 extending through coil assembly 18 and via the cable through the motor to the proximal electronic components 22 which send, receive and interpret signals from the transducer. Components 22 include a cathode ray tube 23, electronic controls for the rotary repetition rate, and standard ultrasonic imaging equipment; see FIG. 12. A rotation detector, in the form of a shaft encoder shown diagrammatically at 19, detects the instantaneous rotational position of this proximal rotating assembly and applies that positional information to components 22, e.g., for use in producing the scan image.

Because the rotation detector depends upon the position of proximal components to represent the instantaneous rotational position of the distal components, the rotational fidelity of the drive shaft is of great importance to this embodiment.

Manufacture and Assembly of the Drive Shaft

Referring to FIGS. 3 and 4, coils 26, 28 are each manufactured by winding four round cross-section stainless steel wires of size about 0.2 mm, so that $D_o$ is about 1.3 mm, $D_i$ is about 0.9 mm, $d_o$ is about 0.9 mm and $d_i$ is about 0.5 mm. The coils are closely wound with a pitch angle $\alpha_o$ and $\alpha_i$ where $\alpha_o$ is smaller than $\alpha_i$, e.g., 22 ½0° and 31°, respectively. Flat wires having a cross-sectional depth of about 0.1 mm may also be used. The pitch angles are chosen to eliminate clearances 60 between the wires and to apply a substantial part of the stress in either tension or compression along the axis of the wire filaments. The coils, connected at their ends, are adapted to be turned in the direction tending to make outer coil 26 smaller in diameter, and inner coil 28 larger. Thus the two assemblies interfere with each other and the torsional stiffness constant in this rotational direction is significantly increased (by a factor of about 6) due to the interference. Operation of the driveshaft in the torsionally stiff region with enhanced fidelity is found to be obtainable by adding a torsional load to the distal end of the rotating assembly of the catheter. The importance of rotational fidelity and details of how it is achieved warrant further discussion.

For ultrasound imaging systems, the relative position of the ultrasound transducer must be accurately known at all times so that the return signal can be plotted properly on the display. Any inaccuracy in position information will contribute to image distortion and reduced image quality. Because position information is not measured at the distal tip of the catheter, but rather from the drive shaft at the proximal end, only with a torsionally stiff and true drive shaft can accurate position information and display be obtained.

Furthermore, it is recognized that any drive shaft within a catheter sheath will have a particular angular position which is naturally preferred as a result of small asymmetries. Due to this favored position, the shaft tends, during a revolution, to store and then release rotational energy, causing non uniform rotational velocity. This phenomenon is referred to as "mechanical noise" and its effect is referred to as "resultant angular infidelity" for the balance of this explanation.

According to the present invention, use is made of the fact that suitably designed concentric coils interfere with each other, as has been mentioned previously. When twisted in one direction, the outer layer will tend to expand and the inner layer contract thus resulting in a torsional spring constant which is equal only to the sum of the spring constants of each of the two shafts. When, however, twisted in the opposite direction, the outer layer will tend to contract while the inner layer will expand. When interference occurs between the inner and outer layers the assembly will no longer allow the outer coil to contract or the inner to expand. At this point, the torsional spring constant is enhanced by the interference between the shafts and the torsional spring constant is found to become five or ten times greater than the spring constant in the "non-interference" mode.

Figure 9:
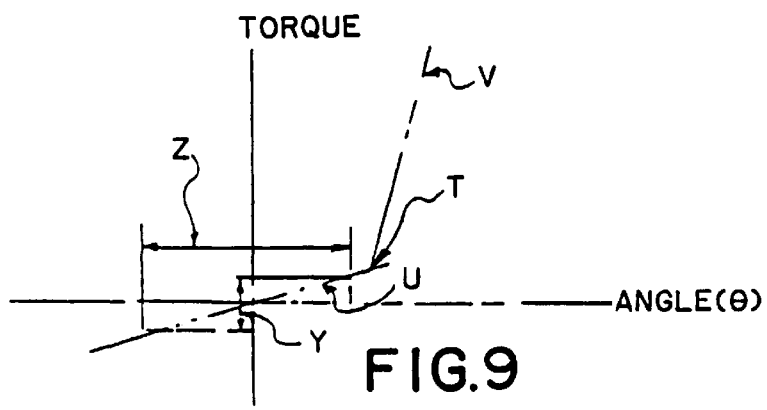
FIGS. 9, 10 and 11 are graphical representations of torque in relation to angular deflection.

Referring to FIG. 9, the relationship between torque and angular deflection for such a coil assembly is shown, assuming one end fixed and torque applied at the opposite end. 'Y' represents mechanical noise; 'Z' resultant angular infidelity; 'T' the interference point; the slope of the line 'U', the torsional spring constant (TSC) without interference (i.e., the sum of the torsional spring constant of each of the two coils); and the slope of the line 'V', the TSC with interference. Thus, TSC is shown to increase dramatically at the interference point.

Figures 10, 11:
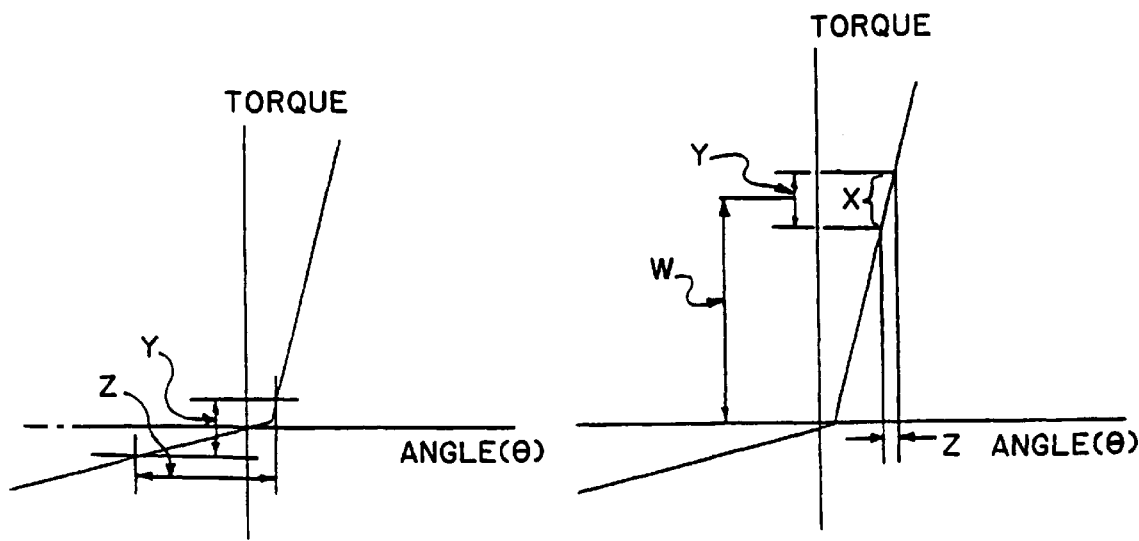

Referring to FIG. 10, by pre-twisting the shafts relative to one another and locking their ends together in a pre-loaded assembly, the interference point is moved to be close to the rest angle and resultant angular infidelity, Z, is reduced in the given direction of rotation.

To improve upon this effect even further, dynamic frictional drag is intentionally introduced at the distal end of the shaft to raise the level of torque being continually applied to the system. This ensures operation of the shaft in the region of the high torsional spring constant or "interference" mode throughout its length, producing a rotationally stiffer shaft. This is shown in FIG. 11, where 'W' is dynamic load and 'X' is the region of operation. The use of such dynamic drag is of particular importance in certain catheters of small diameter, e.g. with outer diameter less than about 2 mm.

To form inner coil 28, four individual wires are simultaneously wound around a mandrel of about 0.5 mm outer diameter. The free ends of this coil are fixed, and then four wires are wound in opposite hand directly over this coil to form the outer coil 26. The wires are wound under moderate tension, of about 22.5 gm/wire. After winding, the coils are released. The inner mandrel, which may be tapered or stepped, or have a constant cross-sectional diameter, is then removed. The wire ends are finished by grinding. One end is then soldered or epoxied to fix the coils together for a distance of less than 3 mm. This end is held in a rigid support and the coils are then twisted sufficiently, e.g. ¼ turn, to cause the outer coil to compress and the inner coil to expand, causing the coils to interfere. The free ends are then also fixed.

The coil assembly 18 is generally formed from wires which provide a low spring index, that is, the radius of the outer coil 26 must be not more than about 2.5 to 10 times the diameter of the wires used in its construction. With a higher index, the inner coil may collapse. The multi-filar nature of the coils enables a smaller diameter coil to be employed, which is of particular importance for vascular catheters and other catheters where small size is important.

After the coil assembly is completed, coaxial cable 32 is inserted within the inner coil. The cable may be silver-coated on braid 36 to enhance electrical transmission properties. It is also possible to use the inner and outer coils 26, 28 as one of the electrical conductors of this cable, e.g. by silver coating the coils.

Referring back to FIGS. 3 and 5, to form transducer 10, wire 42 is soldered to either side of electrically conducting sleeve 29 formed of stainless steel. Wire 44 is inserted into a sound absorbent backing 48 which is insulated from sleeve 29 by insulator 72. Piezoelectric element 46 of thickness about 0.1 mm is fixed to backing 48 by adhesive and electrical connection 74 is provided between its surface and the end of sleeve 29. Thus, wire 42 is electrically connected to the outer face of piezoelectric element 46, and wire 44 electrically connected to its inner face. Spherical lens 52, formed of acoustic lens materials is fixed to the outer surface of element 46.

Referring to FIGS. 4 and 7–7d, the completed drive shaft 18 and transducer 10 are inserted into disposable catheter sheath 12, positioning transducer 10 within acoustically transparent dome element 25, with liquid filling the internal open spaces. The catheter thus prepared is ready to be driven by the drive assembly; see FIG. 8.

During use, rotation of drive shaft 18, due to exposure of the helical surface of the outer coil to the liquid, tends to create helical movement of the liquid toward the distal end of the sheath. This tends to create positive pressure in dome element 25 which reduces the tendency to form bubbles caused by out-gassing from the various surfaces in this region.

As has been mentioned, it is beneficial to provide added drag friction at the distal end of the rotating drive shaft 18 to ensure operation in the torsionally stiff region of the torsional spring constant curve. It is found that this may be done by simply necking down the distal portion of the catheter sheath 12, as shown in FIG. 4 to provide a relatively tight clearance between the distal portion of the shaft 18 and the inner surface of the sheath, to impose the desired degree of viscous drag. As an alternative, the dynamic drag may be provided by an internal protrusion in catheter sheath 12 to create a slight internal friction against drive shaft 18.

The acoustic catheter may be constructed so that it may be preformed prior to use by standard methods. Thus, if the investigator wishes to pass the catheter through a known tortuous path, e.g., around the aortic arch, the catheter can be appropriately shaped prior to insertion. Such preformation can include bends of about 1 cm radius and still permit satisfactory operation of the drive shaft.

Electronics

Figure 12:
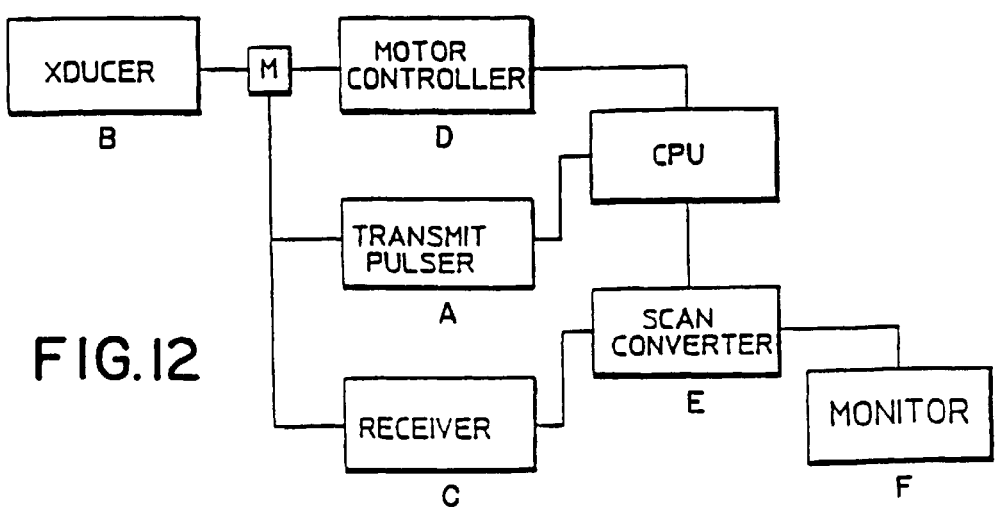
FIG. 12 is a block diagram of the electronic components useful with the acoustical catheter.

FIG. 12 is a block diagram of the electronics of a basic analog ultrasound imaging system used with the acoustical catheter. The motor controller (D) positions the transducer B for the next scan line. The transmit pulsed (A) drives the ultrasound transducer. The transducer (B) converts the electrical energy into acoustic energy and emits a sound wave. The sound wave reflects off various interfaces in the region of interest and a portion returns to the transducer. The transducer converts the acoustic energy back into electrical energy. The receiver (C) takes this wave-form and gates out the transmit pulse. The remaining information is processed so that signal amplitude is converted to intensity and time from the transmit pulse is translated to distance. This brightness and distance information is fed into a vector generator/scan converter (E) which along with the position information from the motor controller converts the polar coordinates to rectangular coordinates for a standard raster monitor (F). This process is repeated many thousands of times per second.

By rotating the transducer at 1800 rpm, repeated sonic sweeps of the area around the transducer are made at repetition rate suitable for TV display, with plotting based upon the rotary positional information derived from the proximal end of the device. In this way a real time ultrasound image of a vessel or other structure can be observed.

Due to its rotational fidelity, the device provides a relatively high quality, real time image of heart tissue. It is also possible to form 3-dimensional images using appropriate computer software and by moving the catheter within the heart.

Selectable Catheter Sheaths

A wide variety of novel disposable catheter sheaths can be substituted for catheter sheath 12 and used in the system.

Figure 13:
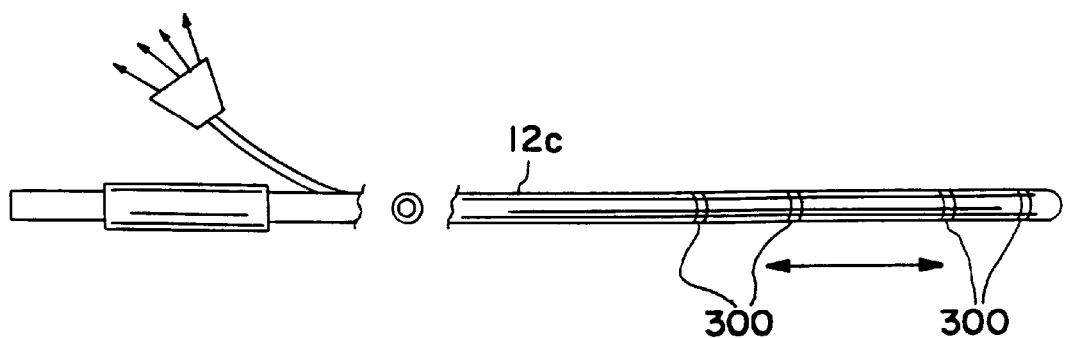
FIG. 13 is a longitudinal view of an acoustic imaging catheter sheath having electrodes for electrophysiology or cardiac ablation mounted on the catheter sheath.

FIG. 13 shows a flexible, disposable catheter sheath 12c on which are mounted a plurality of electrophysiology or ablation electrodes 300. Catheter sheath 12c may be combined with any of the technologies described below in connection with FIGS. 24, 25, and 26 to permit relative longitudinal movement between the transducer and electrodes 300.

Figure 14:
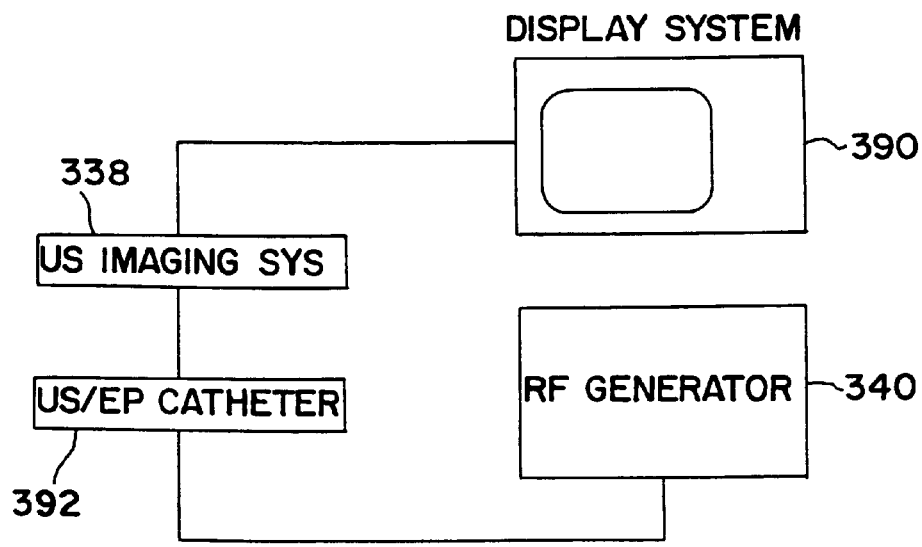
FIG. 14 is a block diagram of the principle components of an acoustic imaging and electrophysiology system that includes the catheter shown in FIG. 13.

With reference to FIG. 14, an ultrasound/electrophysiology catheter 392 such as the one shown in FIG. 13 is connected to an ultrasound imaging system 338 that receives signals from the ultrasound transducer and transmits image data to display system 390 for display as an ultrasound image. RF generator 340 generates RF electrical signals for excitation of the ultrasound transducer or the electrodes. By observing in real time, on display system 390, the region of the heart near ultrasound/electrophysiology catheter 392, a physician can determine the position of the catheter sheath and electrodes relative to cardiac tissue and can also reposition catheter 392 at the same location at a later time. In order to reposition the catheter at the same location the physician either remembers the image or "captures" and stores the image using videotape or computer storage capabilities, so that the physician can compare the real time image with the captured or remembered image to determine whether the catheter has returned to the desired location.

Figure 15:
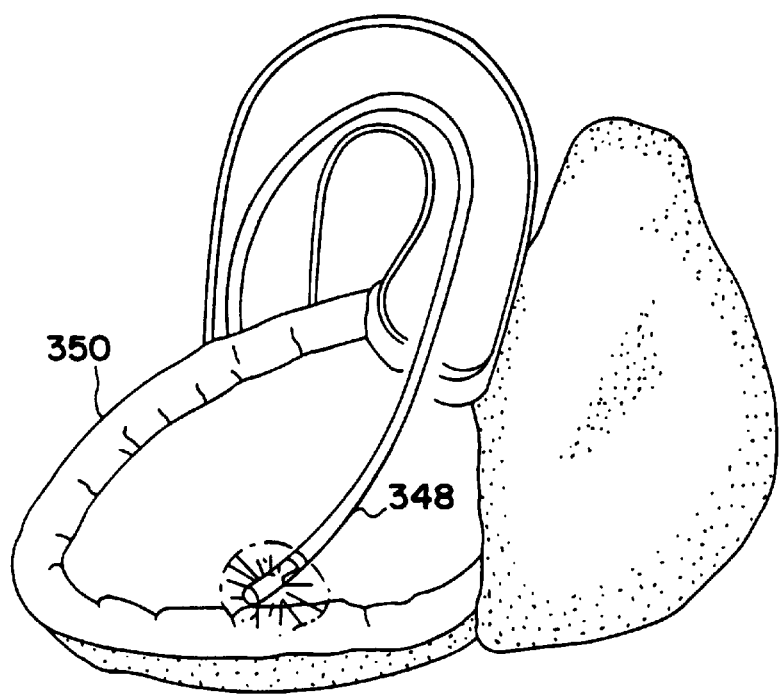
FIG. 15 is a partially cut-away view of a heart showing an acoustic imaging and electrophysiology catheter being used to image a chamber of the heart.
Figure 15A:
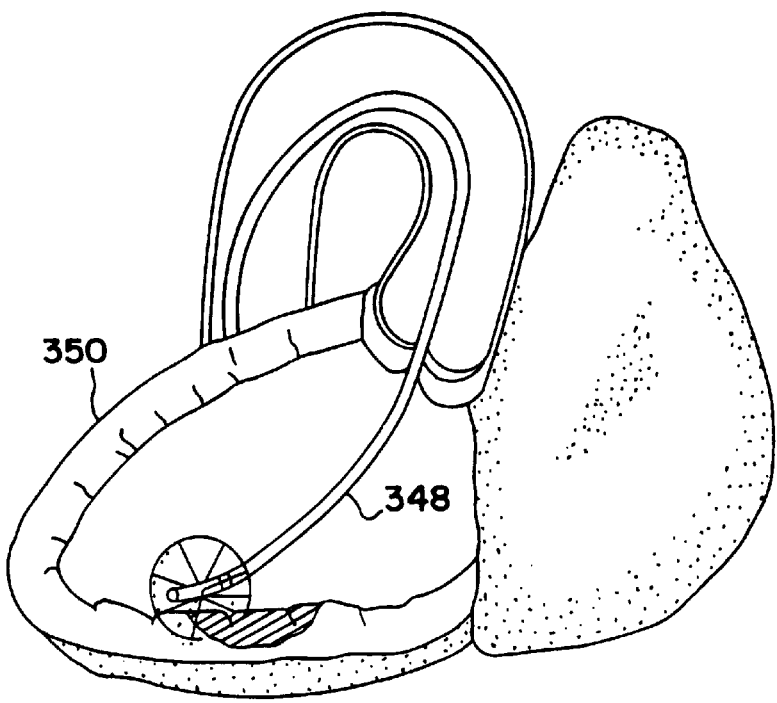
FIG. 15a is a partially cut-away view of a heart showing an acoustic imaging and electrophysiology catheter being used to image a portion of a chamber of the heart that has been ablated by means of the electrodes on the catheter sheath.

One of the questions that arises during the course of positioning the catheter is whether or not a particular electrode is really in good electrical contact with the cardiac tissue. By visualizing the position of the electrode relative to the endocardium, the physician can make a judgment whether that electrode is in the proper position for a reliable reading. If not, the catheter can be readily repositioned by twisting the catheter and manipulating a steering wire, such as the one described in connection with FIG. 16 below, until the electrode or electrodes are in position. Without the use of visual information, the physician could continue to reposition the catheter in many locations of the heart and could compare these readings until he gets a picture in his mind of what the overall electrical activity of the heart is like. Using visual information, however, the physician can develop a better strategy that will tell him what areas of the heart he may ablate (using any of a variety of ablation techniques) in order to correct any perceived deficiencies in the electrical activity of the heart. FIGS. 15 and 15a show an acoustic imaging and electrophysiology catheter 348 being used to image a chamber of heart 350 before and after ablation of heart tissue, respectively.

Because the ultrasound transducer is being used to image points of actual contact of the surface of the electrode with cardiac tissue, it is necessary for the transducer to have close-up imaging capability, i.e., the ability to image from essentially the surface of the catheter outward. This close-up imaging capability is accomplished by using a very high frequency, such as 20 megahertz or higher. In certain circumstances, in which a compromise between close-up imaging and depth of penetration is desired, lower frequencies such as 10 megahertz could be used (there tends to be a trade-off between close-up and depth of penetration).

It is also possible to have more than one transducer on the same rotary shaft, one transducer being used for close-up imaging and the other being used for depth of penetration. Alternatively, there may be a single, multifrequency transducer, which is a step transducer having a piezo-electric element that has a series of concentric plates or zones of varying thicknesses. In one embodiment there would be two zones: a central zone that occupies half of the surface area of the transducer and that has thickness appropriate for generating acoustic waves in the order of 30 megahertz, and an annular zone around the central zone that has a greater thickness appropriate for generating acoustic waves around 10 megahertz. It is advantageous to have a single, multifrequency transducer rather than two different transducers because if a single, multifrequency transducer is used the user can select at will the depth of penetration desired and the frequency of operation desired without having to shift the position of the catheter, whereas if two transducers are used it may be necessary to shift the position of the catheter unless the two transducers oppose each other on opposite sides of the drive shaft.

The electrophysiological information obtained from electrodes 300 can be used to determine the location of catheter sheath 12c within the heart, as an alternative to using the ultrasound transducer. In particular, there are certain voltage patterns that are obtained during the electrophysiology procedure that identify certain landmarks in the heart.

If electrodes 300 are used for ablation, the imaging capability of the catheter can be used to determine immediately whether a specific change to the tissue has resulted from the ablation. Desiccation of tissue manifests itself as a brightening of the region of the ultrasound image corresponding to the location of the lesion. This brightening corresponds to increased reflection of ultrasonic signals.

Figure 16:
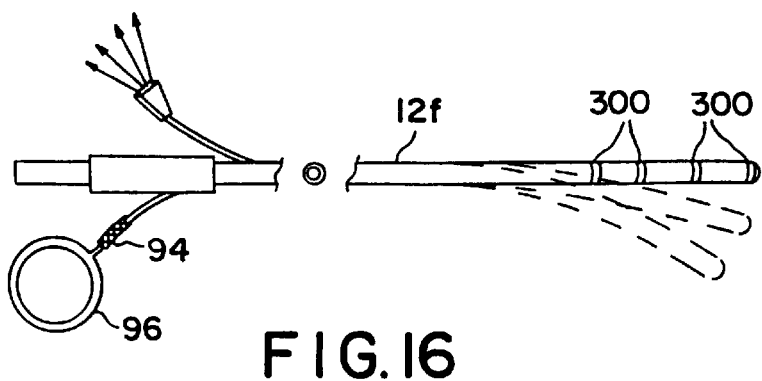
FIG. 16 is a longitudinal view of an acoustic imaging catheter sheath which is deflectable by actuation from the proximal end, and which includes electrodes for electrophysiology or ablation mounted on the catheter sheath.

FIG. 16 shows sheath 12f on which are mounted electrodes 300 for electrophysiology or ablation. Sheath 12f has a two lumen construction. The large lumen contains the transducer and drive shaft while the small lumen contains a wire 94. As shown, wire 94 is a deflecting or steering wire attached near the distal end, and is free to slide through its lumen under tension applied to ring 96 to cause the catheter to bend when pulled taut, thus providing a measure of control of the orientation of the distal end of the acoustic catheter while negotiating the passages of the body or the like. In another embodiment wire 94 may be a preformed stylet, which, when inserted through the second lumen, causes deflection of the tip.

Figure 17:
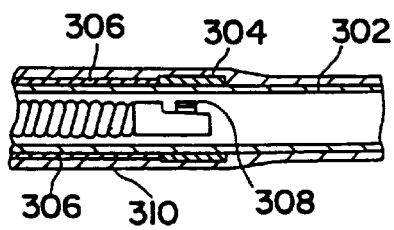
FIG. 17 is a longitudinal cross-sectional view of an acoustic imaging catheter sheath having a sonolucent metallic electrode and having a sonolucent metallic trace leading to the electrode.

FIG. 17 shows an acoustic imaging catheter sheath 302 having a sonolucent metallic electrode 304 for sensing electrical potentials or for ablation, and having a pair of sonolucent metallic traces 306 leading to electrode 304. Catheter sheath 302 has a diameter of nine french or less, and most preferably six french or less. Imaging transducer 308, because it is slidable (in accordance with any of the techniques described below in connection with FIGS. 24, 25, and 26), can be placed under or near electrode 304.

Because metal electrodes are very efficient reflectors of ultrasound energy, one would expect that there would be a high likelihood that reverberation artifacts would result when trying to image directly near, or as close as possible to, electrode 304 itself. Nevertheless, as described below, it is possible to make the electrode acoustically transparent, so that such reverberation artifacts do not tend to result, while the electrode is sufficiently conductive to perform the task of sensing and has a sufficiently low resistance to perform the function of ablation. The resistance from the proximal connector of the catheter to electrode 304 should be no more than 50 to 100 ohms for sensing and no more than 25 to 50 ohms for ablation. Otherwise, undue heating of the catheter could occur.

In one method of fabricating catheter sheath 302, a sonolucent tube of polyethylene is imprinted with conductive material to form electrode 304 and traces 306 leading to electrode 304. Electrode 304 and conductive traces 306 are made of aluminum that is deposited by vacuum deposition, which has been found to produce a low resistance, high reliability, conductive path that is sufficiently thin to allow ultrasound energy to pass through the aluminum almost unhindered. Then a covering 310, which is also sonolucent, is applied over the conductively treated catheter body to protect and seal electrode 304 and traces 306. Covering 310 includes micro-apertures filled with conductive material, as shown in FIG. 18a below. Because catheter sheath 302 and covering 310 are formed of a sonolucent material and because electrode 304 and traces 306 do not tend to reflect ultrasound energy, the presence of electrode 304 and traces 306 does not tend to create artifacts in the ultrasound image.

We now describe the vacuum deposition technique by which electrode 304 and traces 306 are deposited onto the sonolucent tube. First, the sonolucent tube, which is a single-lumen extrusion, is placed on a mandrel in a manner such that it can be held straight. Then a flat copper plate, such as is used for lithography, is photoetched over an area as long as the sonolucent tube and as wide as the circumference of the sonolucent tube in a manner such that a negative of the pattern of the traces and the electrode is imprinted upon the plate. The pattern is in the form of a waxy ink material rolled onto the copper plate. The sonolucent tube is than placed onto the copper plate at one side and rolled to the other side, which causes the sonolucent tube to be printed around its entire periphery in the manner of a printing roll.

The sonolucent tube is then placed into a chamber that is evacuated, with the mandrels being placed on a rotisserie so that they rotate. The sonolucent tube is coated with metal by a vacuum deposition process in which the metal is caused to melt in a graphite boat by induction heating and then the metal evaporates and deposits over the entire surface of the sonolucent tube. The metal covers both the areas where the ink is located and the areas where there is no ink. Then the sonolucent tube is removed from the chamber and is washed with a solvent such as trichlorethylene. This process washes away the ink with the aluminization that covers the ink, leaving the areas that are not printed with the ink intact with a thin aluminum coating.

The metal may alternatively be deposited onto the sonolucent tube by laser xerography, according to which a charge is put on the surface of the sonolucent tube, which tends to selectively accept aluminum ions or charged molecules as they are deposited. The metal is deposited by a vacuum deposition process in which the metal is caused to melt in a boat on which a charge has been placed, and the metal evaporates and charged metal particles deposit in the appropriate places on the sonolucent tube in accordance with xerographic techniques.

Alternative methods of depositing the metal onto the sonolucent tube include spraying a conductive paint onto a pattern on the sonolucent tube or spraying with a plasma gun (a small electron gun) that is capable of selectively depositing evaporated metal in specific areas on the sonolucent tube. The gun doesn't actually touch the surface of the sonolucent tube, but sprays the surface in a manner analogous to a very tiny airbrush.

If multiple electrode rings are formed on the sonolucent tube, some of the electrode rings may not completely encircle the sonolucent tube because certain traces would have to pass through these electrode rings. Alternatively, the traces and protective sonolucent coverings could be deposited as a multi-layer structure. For example, an electrode near the tip of the sonolucent tube could be deposited as a complete ring connected to a trace extending along the length of the sonolucent tube, and then a protective sonolucent covering could be placed over the deposited metal, and then a second deposition process could be performed to lay down a second ring, and so on as various layers of material are built up one on top of the other.

Another method of fabricating the catheter is to first print electrode 304 and traces 306 on a flat sheet of acoustically transparent material such as polyimide, and to roll that sheet up in a spiral like a jelly-roll and either place the sheet on the sonolucent tube or have the sheet be the sonolucent tube itself.

To prevent damage to the fragile electrodes and traces, a thin, acoustically transparent covering is placed over the aluminized or metallized catheter body. The covering may be nylon that is expanded and then shrunk onto the catheter body, or polyethylene that is shrunk onto the catheter body. Alternatively, the covering may be formed by spraying or dipping methods. Nylon and polyethylene are dialectic materials, and thus function as electrical insulators that would prevent the electrodes functioning when placed in proximity to the heart tissue were it not for the fact that microapertures are drilled through the protective coating.

Figure 18:
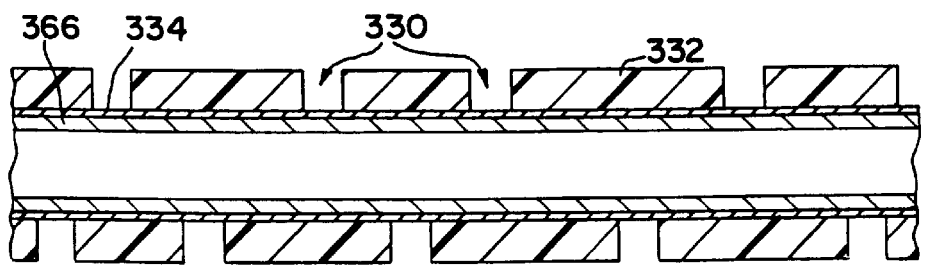
FIG. 18 is a longitudinal cross-sectional view of an acoustic imaging catheter sheath having a sonolucent metallic electrode and having a protective covering over the electrode with micro-apertures drilled through the covering.
Figure 18A:
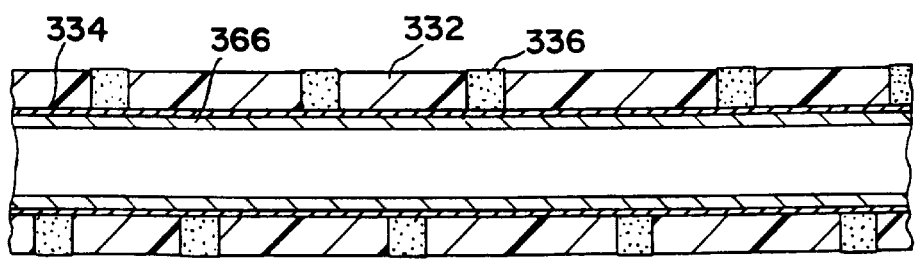
FIG. 18a is a longitudinal cross-sectional view of the acoustic imaging catheter sheath of FIG. 18 showing the micro-apertures filled with conductive material.

As shown in FIGS. 18 and 18a, the microapertures 330 in a protective coating 332 over a sonolucent electrode 334 and a sonolucent substrate 366 are very small holes, e.g., one micron in diameter or up to ten microns in diameter, drilled by UV eximer laser machining techniques, and are as thick as protective coating 332. The number of pulses of the eximer laser is selected in a manner such that the laser penetrates the thickness of the coating but does not to go below metal electrode 334; in any event, when the laser hits the metal it is just reflected anyway. The eximer laser technology could be provided by Resonetics, Nashua, N. H. 03063.

The density of microapertures 330 is as high as possible consistent with the strength of the materials. Generally, one needs to have 62,500 apertures in an area that is 3 square millimeters. The apertures can be formed very rapidly by indexing and also by optical steering while the catheter body is rotating. After these apertures are formed, the apertures are filled with a conductive jell material 336 such as that used for EKG electrodes at the place of manufacture of the catheter sheath. The conductive jell is then wiped clear of the catheter sheath. Alternatively, the apertures can be filled with an epoxy that includes tantalum, gold powder, or silver powder, or PVDF filled with a metal powder.

If the electrode is to be used for high-current ablation, the electrode-to-terminal resistance should be no more than 20 to 50 ohms, rather than the limit of 50 to 100 ohms that is acceptable for sensing purposes. The better conduction required for ablation can be achieved by applying additional gold plating over the areas that have been drilled with the micro-apertures, using masking and plating techniques or vacuum deposition, or using a gold plating solution.

An alternative to using the micro-apertures is to have the aluminized surfaces of the electrode simply exposed and to put protective covering over the traces but not the electrode. In order to minimize problems due to wear and handling of the electrodes, the exposed electrodes should be subjected to proper surface treatment and texturing.

FIGS. 19–19c show a catheter sheath 12d on which is mounted a balloon 55 very near the tip of catheter sheath 12d. The balloon is adapted to be pressurized with liquid, such as saline or water, or a gas, such as air, through the same lumen that holds the ultrasound imaging device, via an inflation opening in the wall of the catheter sheath. The balloon may be used to center or position the ultrasound device securely within a heart chamber and maintain its position away from an area of interest on a wall of the heart. The balloon in its collapsed or unpressurized state is easily inserted prior to positioning and may be accurately positioned by use of ultrasound imaging during initial placement. In other embodiments a separate lumen is provided for inflation of the balloon and/or the balloon is spaced from the distal end of the catheter.

If balloon 55 is filled with air at an appropriate point in time the balloon floats in a manner that assists the positioning of the catheter. For example, the balloon might float upwards from a lower ventricle to a higher atrium, for instance. The balloon physically moves the tip of the catheter from one location in the heart to another in a manner which is not possible with steering and pushing, although the balloon can be used in conjunction with such steering and pushing techniques. For example, the embodiment shown in FIG. 19 may be modified to include the steering wire shown in FIG. 16.

If balloon 55 is filled with air it can move either with the flow of blood or against the flow. If the balloon is inflated with liquid, such as saline, it becomes a flow-directed balloon that can travel only with the flow of blood. Such a flow-directed balloon is also useful to direct the catheter in the heart. Cardiologists know the path of flow in the heart very well, and if a cardiologist knows that the direction of flow in the heart is favorable for use of a flow-directed balloon, he can fill the balloon with fluid to cause it to move with the flow.

Thus, the air-filled or fluid-filled balloon simplifies the task of positioning the catheter, even if the catheter includes steering or torquing devices that assist in positioning of the catheter within the heart. Balloon 55 can also be used to perform other functions in the heart, such as valvularplasty.

In one embodiment balloon 55 is acoustically transparent, so that it doesn't obstruct the field of view of the acoustic imaging transducer. Materials such as cross-link polyethylene have high inflation strength, good biocompatability, processability, freedom of pinholes, and very low acoustic attenuation. These are commonly used balloon materials. It is also possible to use a latex or silicone balloon.

Frequently, when performing an electrophysiology sensing procedure or an electrode ablation procedure the clinician would like to apply pressure to the electrode and its adjacent heart tissue in order to assure a firm contact. Accordingly, in one embodiment, balloon 55 is an "opposing positioning balloon," i.e., a balloon that engages a wall of the heart or a structure such as the coronary sinus when the balloon is inflated in such a way as to cause one or more electrodes to press firmly against the cardiac tissue. FIG. 19 shows a single sensing or ablation electrode 394 mounted on the distal end of catheter sheath 12d, but in alternative embodiments there is more than one electrode. The electrode or electrodes may be mounted on catheter sheath 12d (as in FIG. 19), or on balloon 55 (as in FIG. 20), or on both catheter shaft 12d and balloon 55. With reference to FIG. 20, electrodes 394 can be printed on or placed on balloon 55 as rings or stripes by vacuum deposition, in a manner analogous to the method, described above, of creating acoustically transparent electrodes on a catheter sheath. Electrodes on catheter sheath 12d can also be created by this method, or can be simple metal rings of gold, silver, tantalum etc. FIG. 19 shows opposing positioning balloon 55 concentric to catheter sheath 12d, but in other embodiments the opposing positioning balloon is eccentric to the catheter sheath and the balloon is used to press the side of the catheter sheath itself the heart wall.

FIG. 21 shows balloon 55 combined with a chemical ablating needle 396, such as the one described below in connection with FIGS. 27 and 27a, that is constructed to inject a chemical into heart tissue to ablate the tissue. Needle 396 exits through a side wall of balloon 55, as shown in detail in FIG. 21a. Alternatively, needle 396 may exit catheter sheath 12d near balloon 55. Balloon 55 is made of an electrically excitable, acoustic generating material such as polyvinylidene fluoride (PVDF). During use, needle 396 is inserted into tissue under ultrasound guidance, the balloon is inflated, and the balloon material is electrically excited to aide the transfer of fluid from the needle into the adjacent tissue.

With reference to the embodiments shown in FIGS. 20 and 21, balloon 55, which is made of polyvinylidene fluoride (PVDF), has a number of small apertures 398 in the wall of the balloon. The inside of balloon 55 is connected to a source of a drug by means of a lumen extending through catheter sheath 12d. Apertures 498 are force fed with the drug while the balloon material is caused to vibrate. The vibrations feed the transfer of the fluid from balloon 55 into tissue with which the balloon is in contact. Radiopaque markers 410 and 412 are provided on catheter sheath 12d.

Referring still to FIGS. 20 and 21, PVDF is a material that is similar to mylar and can be fabricated in sheets and then formed into balloons that have wall thicknesses in the range from 1–2 thousands of an inch. In order to permit excitation of the balloon wall, the PVDF material has to be aluminized inside and out with aluminum layers 400. A very thin layer of aluminization is all that is needed because the electrically excitable balloon 55 is a high impedance device. During use, an alternating electric current is applied to balloon 55 at frequencies in the kilohertz to megahertz range (the frequency depending on the thickness of the balloon and the mode of excitation). The electric current causes the balloon to exhibit either transverse or planar vibration, which is therapeutically helpful in speeding the delivery of drugs and fluid into adjacent tissue. The vibration creates localized variations in pressure in the tissue, and given that fluid tends to migrate in the direction of areas of low pressure, the vibration helps migration of fluid through the tissue. The vibration also can create heat, which is known to improve the diffusion of some chemicals through tissue. Very high levels of vibration can be used as a massaging action to actually disrupt tissue and to directly create an ablative response.

Figure 22:
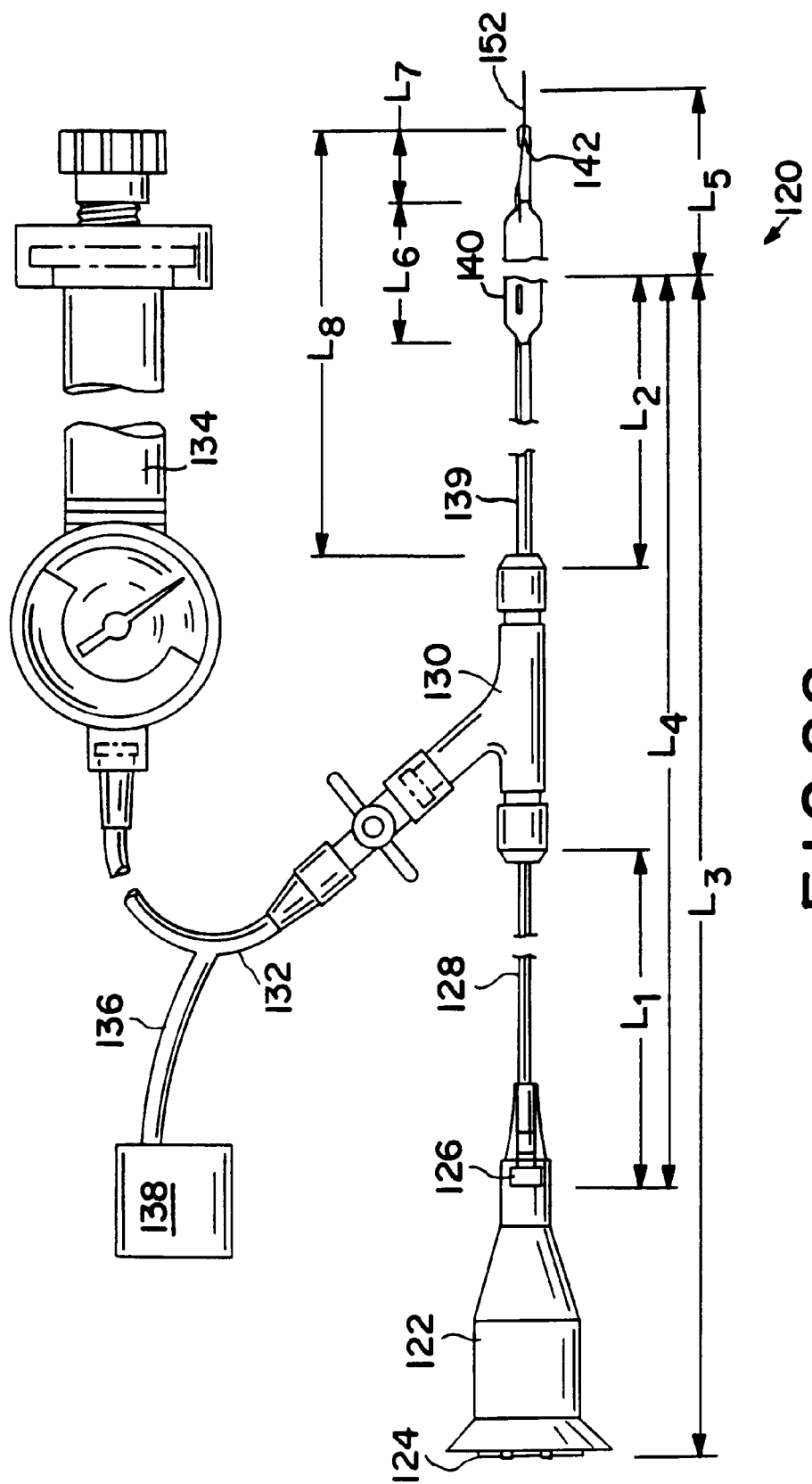
FIG. 22 is a longitudinal view of one embodiment of an acoustic imaging balloon catheter.

Referring to FIG. 22, a plan view of an acoustic imaging balloon catheter system is shown. This acoustic imaging balloon catheter system may include all of the features of the catheter system shown in FIGS. 19–19c, including one or more electrodes for electrophysiology or ablation mounted on the catheter sheath. The system 120 includes a boot member 122 including a ferrule member 124 at its proximal end, constructed to enable electrical and mechanical connection, as discussed for example with respect to FIGS. 8–8a, to the acoustic imaging control system as discussed for example with respect to FIG. 1, for transmitting rotary power and control signals to the acoustic imaging transducer held within the balloon catheter sheath 139 near balloon 140 and for receiving acoustical image signals from the transducer. The proximal end of the apparatus further includes a seal 126 (FIG. 23) which enables intimate but relatively frictionless contact with the portion of the rotating drive shaft.

Sheath 128 extends from the end of the seal 126 to a "Y" double flare compression fitting 130. Fitting 130 includes a side arm 132 for introduction of inflation fluid such as water or saline by means of a screw syringe 134 for inflation of balloon 140 near the distal end of the catheter 139.

Extending distally from the compression fitting 130 is catheter body sheath 139. The catheter may be adapted to track a guide wire which passes through a sonolucent saddle member beneath the balloon.

A rotating ultrasound transducer having a coil form drive shaft, as discussed herein above, is positioned on the central axis of the catheter sheath 139 at a position corresponding to the inflatable balloon 140. The catheter sheath 139 forms a sonolucent guide for the transducer and drive shaft. The catheter sheath is formed of a thin sonolucent material such as polyethylene to provide sufficient guidance for the drive shaft and transducer without causing excessive attenuation of the ultrasound signal emitted by the transducer. The catheter body material and the balloon material are in general selected to be sonolucent and have an acoustic impedance substantially matched to the body fluid, e.g., blood, to which the catheter is exposed, to minimize attenuation of the acoustic signals emitted and received from the transducer. Polyethylene is advantageous in that it has an acoustic impedance that substantially matches blood and saline, it is capable of withstanding high inflation pressures and is only slightly elastic, enabling a reliable balloon inflation diameter. It will be understood that the catheter may be formed having sonolucent regions corresponding to the location of the transducer while the rest of the catheter is not sonolucent, e.g., made of thicker material. Fluid communication between the balloon and the catheter may be provided through a port.

The balloon 140 which is preferably polyethylene, as discussed, may be mounted at its ends by, for example, melt-sealing. The balloon may also be secured by clips or the like as conventionally known.

Figure 23:
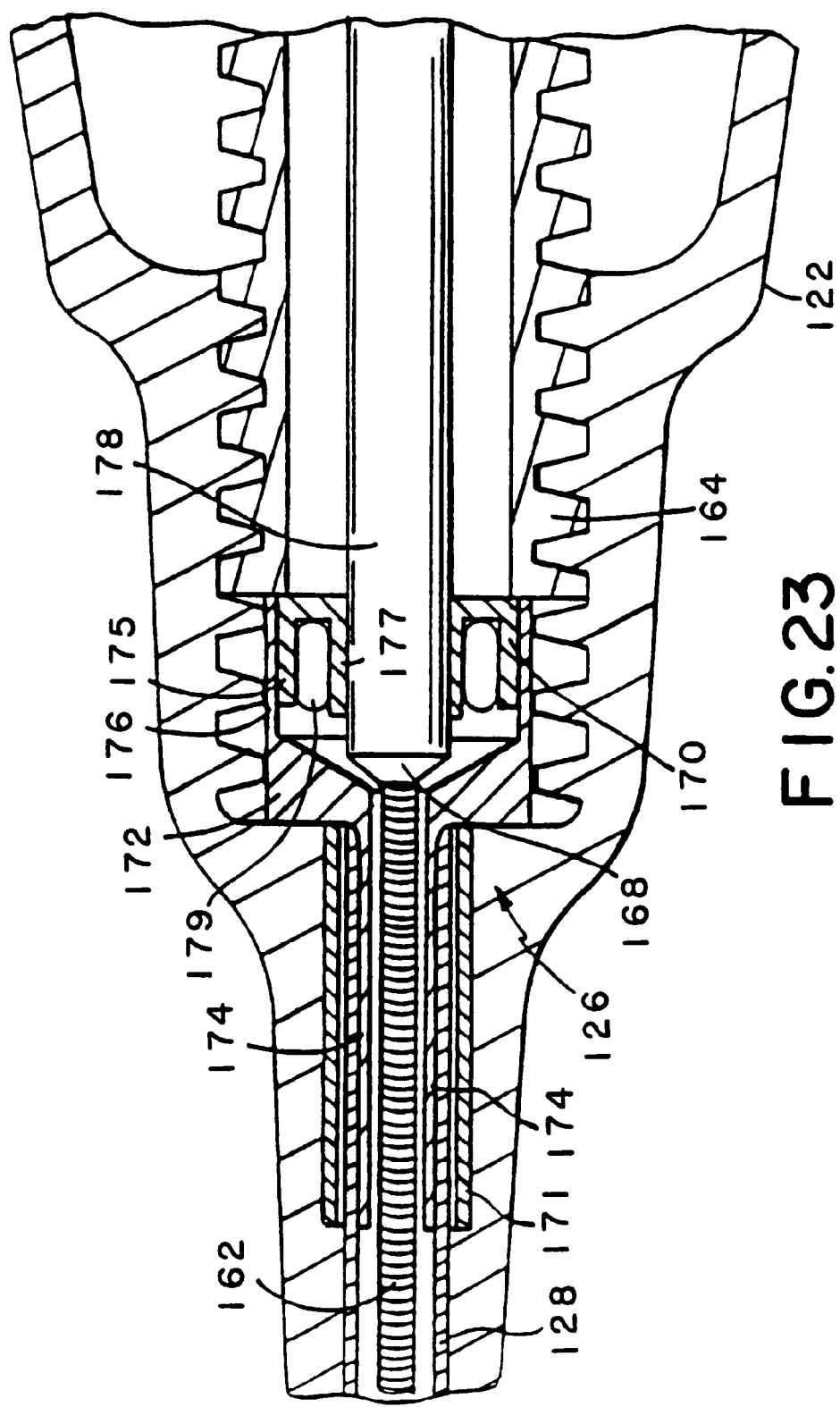
FIG. 23 is an expanded longitudinal cross-sectional view of the proximal end of the catheter coupling of the acoustic imaging balloon catheter of FIG. 22, in partial cross-section.

Referring to FIG. 23, proximally, the catheter of FIG. 22 is provided with a stationary pressure tight shaft seal 126 that fits in intimate, but relatively frictionless contact with a portion of the rotating drive shaft 162. The seal includes a ball seal 170 (available from Bal-seal Engineering Company, Inc., Santa Anna, Calif.), securely held in place by a seal holder 172 (stainless steel or elastomer), which abuts the distal end of the internal open area of the boot 122 and is held by compression of the ferrule assembly 164 (although other means of attachment such as injection molding are possible). The seal holder 172 includes a retainer sleeve 174 that extends coaxially with respect to the catheter 139. At the proximal end, within the ferrule, the drive shaft is held within a gland 178, preferably formed from hypotubing, which makes relatively frictionless contact with the ball seal 170, enabling rotation while preventing back flow of inflation fluid into the ferrule. The ball seal, as shown, is an annular U-shaped member, including within the U a canted coil spring 179 (such that the axis of each coil is tangent to the annulus) that presses the legs 175, 177 of the seal radially. The outer leg 175 of the seal engages an extension 176 of the seal holder, while the inner leg 177 of the seal engages the gland 178. The boot also includes a thin (few thousands of an inch) metal sleeve 171 for additional sealing around the catheter.

The drive shaft 162 is modified in the sealing area 168 by impregnating it with a thermoplastic material that fills the gaps in the individual wires to prevent flow of inflation fluid through the drive shaft inner lumen. Alternatively, the drive shaft may be sealed by impregnating it with a liquid that is hardenable, such as epoxy, and then covering that area with a section of cylindrical metal, such as hypotube, in order to form a smooth, fluid tight seal. It will also be understood that other sealing members may be used, e.g. an O-ring.

Preparation of the device is accomplished by the following steps: A Leveen inflator is connected to the side arm. The side arm valve is opened and air is evacuated by suction. Generally, the balloon contracts in a folded manner which leaves air passages through the interior of the balloon. A hypodermic syringe fitted with a small gauge needle and filled with a fluid such as water or saline is then inserted through a septum seal at the distal tip of the catheter sheath. Fluid is introduced until surplus exits the side arm, at which point the valve is closed, reducing the chances that air will re-enter the catheter. Alternately, the fluid may be introduced via the side arm when an air venting needle is inserted into the distal septum.

The catheter is then attached to the driving motor, (not shown), by mating the ferrule 124 with a mateable receptacle that connects it to the ultrasound imaging electronics. Because the balloon material and sonolucent guide effectively transmit ultrasound energy, continuous imaging and monitoring can be achieved.

The pressure and fluid tight connector that is mounted distally to the location of the side arm connector enables various catheters, such as those with balloons of different sizes, to be effectively attached at the location of the side arm connector.

In other embodiments, the transducer may be positioned proximal to the balloon.

Figure 24:
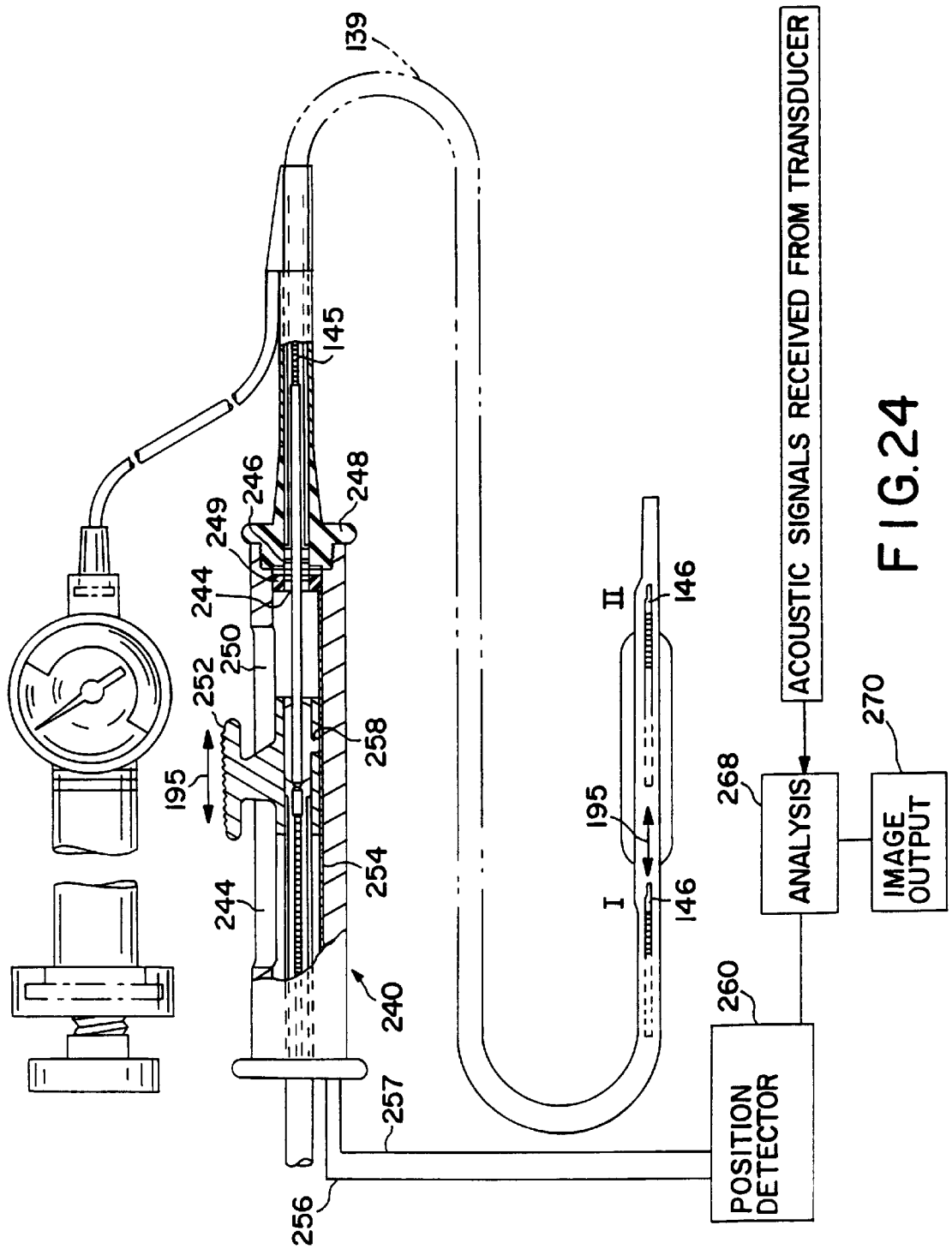
FIGS. 24, 25, and 26 are longitudinal views of alternative embodiments of acoustic imaging balloon catheters enabling relative axial positioning of the transducer and the balloon.
Figure 26:
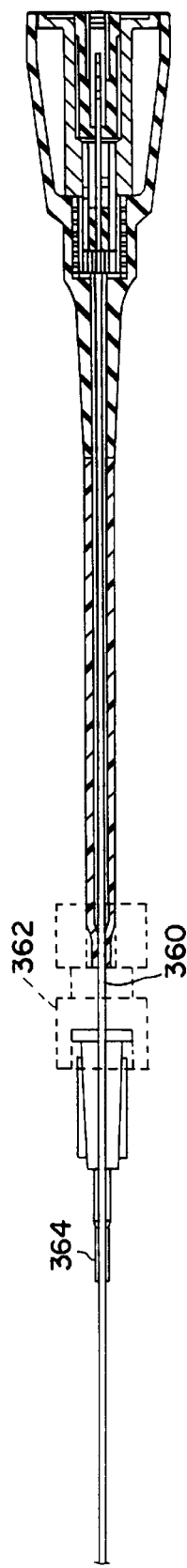
Figure 25:
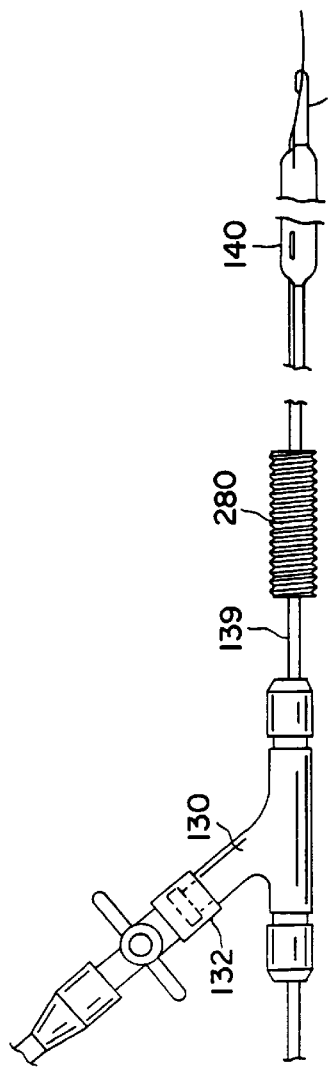

Referring now to FIGS. 24, 25, and 26, other embodiments of the acoustic imaging catheter device allow relative movement of the transducer and balloon so that the ultrasound transducer may be positioned in any longitudinal position in the balloon, or distal or proximal to the balloon. The embodiments shown in FIGS. 24, 25, and 26 may include all of the features of the catheter system shown in FIGS. 19–19c, including one or more electrodes for electrophysiology or ablation mounted on the catheter sheath, and may include all of the features of the catheter system shown in FIGS. 22 and 23. Moreover, the features shown in FIGS. 24, 25, and 26 may be used in conjunction with any of the catheter sheaths disclosed in this application, including catheter sheaths that do not include balloons and including all of the catheter sheaths on which electrophysiology or ablation electrodes are mounted. In FIG. 24, the drive shaft and transducer 146 may be slid axially as indicated by arrows 195 to move the transducer, for example, continuously to positions between position I, proximal to the balloon and position II, distal to the balloon. A slide assembly 240 is provided including a housing 244 having a distal end which receives the catheter sheath 139 and drive shaft 145. The drive shaft contacts a pair of oppositely arranged, relatively frictionless ball seals 245, 246 press fit within the housing against an inner body extension 249 and the distal end member 248 of the body which is threaded into the body 244. The ball seals engage a gland 250 as discussed with respect to FIG. 23. The gland is attached to a thumb control 252, provided within the body to enable axial motion of the drive shaft to position the transducer within the catheter corresponding to regions within the balloon and in the distal extension, both of which are sonolucent.

The axially translatable transducer device further includes a carbon resistor 254 within the slide assembly housing, and contact means 258 attached to the thumb control and in contact with the resistor. Probe wires 256, 257 are connected to the resistor 254 and contact means 258 to provide variable resistance between the probe wires as the thumb control is slid axially, which is detected at detector 260, to provide monitoring of the axial position of the transducer. The thumb control may be hand actuated or controlled by automatic translator means 264 which receives control signals from a controller 266. The output from the detector 260 may be provided to an analysis means 268 which also receives the acoustic images from the transducer corresponding to various axial positions of the transducer within the catheter body to provide registry of the images with the axial transducer position on a screen 270. In certain embodiments, the transducer is slid axially, along a continuous length or at selected positions of the catheter body, for example, from the balloon to the distal tip, and the analysis means includes storage means for storing images along the length to reconstruct a three-dimensional image of the lumen along the axial length of transducer travel.

FIG. 25 shows an embodiment in which the catheter includes a bellows member 280 to enable axial motion of the catheter body with respect to the transducer.

FIG. 26 shows an embodiment in which a proximal portion of the drive shaft is enclosed within tubing 360, which is engaged by a user-graspable housing 362 that is attached to the proximal end of catheter sheath 364. The user can push tubing 360 into housing 362 and can pull it out of housing 364 to adjust the relative longitudinal position of the transducer on the end of the drive shaft with respect to catheter sheath. User-graspable housing 362 engages tubing 360 by means of a fluid-tight seal.

In another embodiment of the acoustic imaging catheter device, the balloon is asymmetrical, either in shape or expansion capability, or both, and is mounted on a catheter shaft that is torquable, and can be positioned using acoustic imaging. The positioning of the balloon relative to surrounding tissue and the inflation and deflation of the balloon can be monitored with cross-sectional ultrasonic images.

Figure 27:
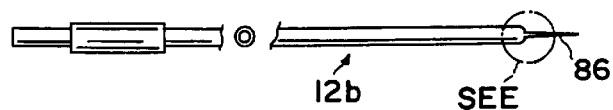
FIG. 27 is a longitudinal view of an acoustic imaging catheter sheath having a hollow needle, extending from the distal tip of the catheter sheath, for injection of fluid into cardiac tissue.
Figure 27A:
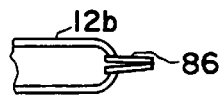
FIG. 27a is a detailed cross-sectional view of the distal tip of the catheter sheath shown in FIG. 27.

FIGS. 27 and 27a show sheath 12b having needle 86 securely anchored to the tip, useful for impaling a surface, such as that found in the interior of the heart, and injecting chemicals such as ethanol into the heart. Needle 86 can also be used to anchor temporarily and steady the ultrasound device in a fixed position. In another embodiment, it can have a safety wire extending to a proximal securing point. This acoustic catheter may be introduced through an introducing catheter. In another embodiment, the needle can be retracted during introduction.

Figure 28:
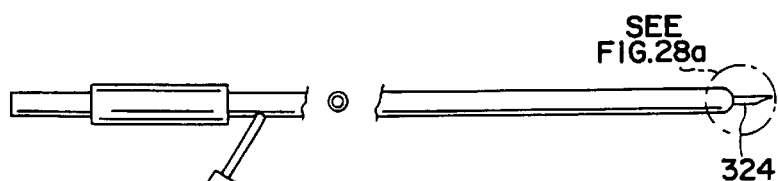
FIG. 28 is a longitudinal view of an acoustic imaging catheter sheath having a needle, extending from the distal tip of the catheter sheath, constructed of an electrically excitable material that generates acoustic energy when excited.
Figure 28A:
FIG. 28a is a detailed, partially cross-sectional view of the distal tip of the catheter sheath shown in FIG. 28.

FIGS. 28 and 28a show a solid needle 324 made of an electrically excitable material that emits acoustic energy when excited through conductor 326 by RF electrical signals applied to electrical terminal 328. Vibration of needle 324 creates a massaging action that disrupts tissue and creates an ablative response.

In an alternative embodiment, needle 324 is hollow, and the vibration of the needle assists the process of injecting the drug into the tissue. The hollow metal is covered with a shrink of polyvinylidene fluoride, and the polyvinylidene fluoride is aluminized over its outside. This construction produces an assembly that vibrates when electrically excited. The purpose of the aluminum is to conduct electric power. The aluminum can be seen in the image formed by means of the ultrasound transducer, and it can also serve as an acoustic marker that can be seen by an external ultrasound device or an ultrasound probe placed a distance away from the ablation catheter.

Figure 29:
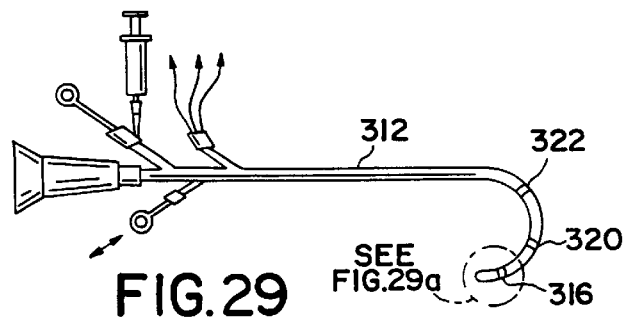
FIG. 29 is a perspective view of an acoustic imaging catheter sheath having a hollow needle, extending from a side wall of the catheter sheath, for injection of fluid into cardiac tissue, and having electrodes for electrophysiology or cardiac ablation mounted on the catheter sheath.
Figure 29A:
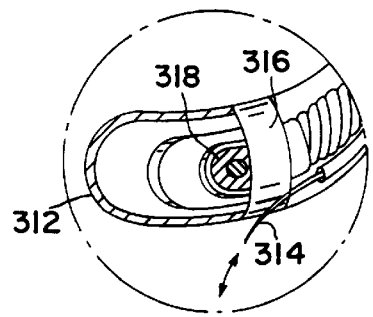
FIG. 29a is a detailed, partially cross-sectional view of the distal tip of the catheter sheath shown in FIG. 29.

FIGS. 29 and 29a show steerable catheter sheath 312, capable of electrophysiology sensing and acoustic imaging, in which the tip of retractable injecting needle 314 exits catheter sheath 312 near the tip of the catheter sheath and also near ring electrode 316 and the position of the scan plane of transducer 318. Visualization of the location of the electrode can be performed under ultrasound guidance, and then the needle can be extended into the endocardium to inject fluid into the endocardium. Electrode 316 is the most distal of several electrodes 316, 320, and 322. Ring electrode 316 may be of a conventional type that can be located with ultrasound. In another embodiment electrode 316 is a tip electrode rather than a ring electrode.

In one embodiment, the longitudinal position of the transducer is adjustable, in accordance with any of the techniques described above in connection with FIGS. 24, 25, and 26. In another, simpler embodiment, transducer 318 is located permanently in a fixed longitudinal location at which the plane of acoustic imaging intersects the needle when the needle at the beginning of its extended position.

In use, the catheter is put into position in the heart with needle 314 retracted, a site that is suspected of electrical malfunction is probed with the steerable catheter under ultrasound visualization, and electrical potentials are read and recorded. Once a specific location is found that appears to be problematic, ablation can then be performed by deploying the needle and the needle can inject the tissue with an ablative drug such as ethanol. The needle can penetrate 2–3millimeters if necessary. The catheter can be left in position during this time and a change in the electrical properties of the tissue can be monitored.

In another embodiment, a highly conductive wire, such as gold-plated metal or gold-plated stainless steel, can be used in place of the needle. The wire ablates tissue in a manner analogous to the ablation electrodes described above, but the wire can be used to anchor the catheter and could be curved to pull the electrode into position to enhance the electrical ablation. The wire can include an acoustic marker that can be seen by an external ultrasound device or an ultrasound probe placed a distance away from the ablation catheter.

Figure 30:
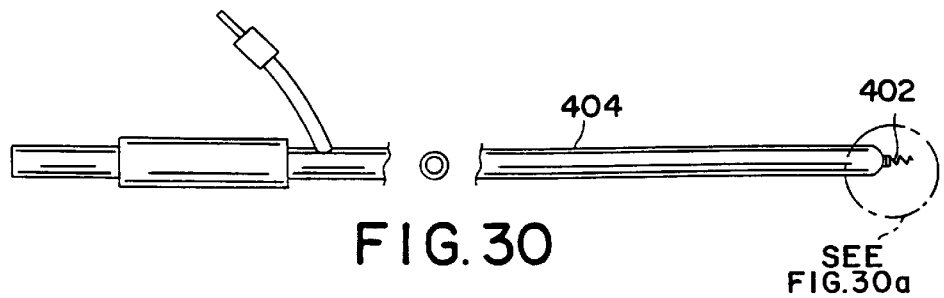
FIG. 30 is a longitudinal view of an acoustic imaging catheter sheath having a wire in the shape of a cork screw attached to its distal end.
Figure 30A:
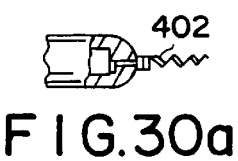
FIG. 30a is a detailed, partially cross-sectional view of the distal tip of the catheter sheath shown in FIG. 30.
Figure 31:
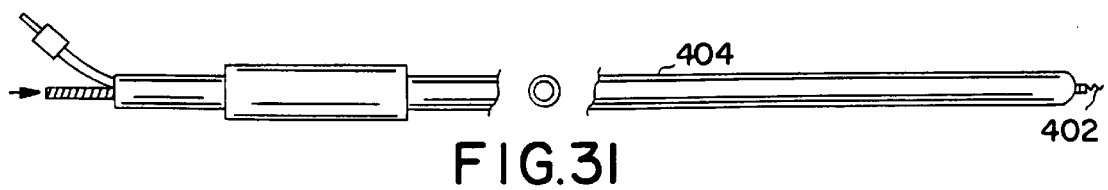
FIG. 31 is a longitudinal view of an acoustic imaging catheter sheath having a wire in the shape of a cork screw passing through its distal end, the wire being attached to the drive shaft within the sheath.
Figure 31A:
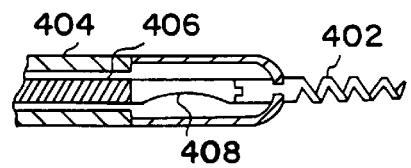
FIG. 31a is a detailed, partially cross-sectional view of the distal tip of the catheter sheath shown in FIG. 31.

In certain embodiments, shown in FIGS. 30, 30a, 31, and 31a, the wire is formed as a little cork screw 402 that can be twisted into the heart, in a manner similar to twisting a pacing lead into the heart, to anchor the tip of catheter sheath 404 very securely under ultrasound guidance. FIGS. 30 and 30a show cork screw 402 directly attached to catheter sheath 404. In this embodiment cork screw 402 is twisted into heart tissue by rotating the entire catheter. FIGS. 31 and 31a show cork screw 402 directly attached to drive shaft 406, distally beyond transducer 408. In this embodiment cork screw 402 is twisted into heart tissue by rotating drive shaft 406. In other embodiments, the corkscrew is attached to an elongated, torsionally rigid but laterally flexible assembly, similar to the ultrasound imaging driveshaft but much smaller in diameter, so that the corkscrew can be automatically caused to turn and corkscrew into tissue. The corkscrew exits a small hole in the catheter sheath in the same manner as needle 314 described above, but the corkscrew follows a curved path.

Figure 32:
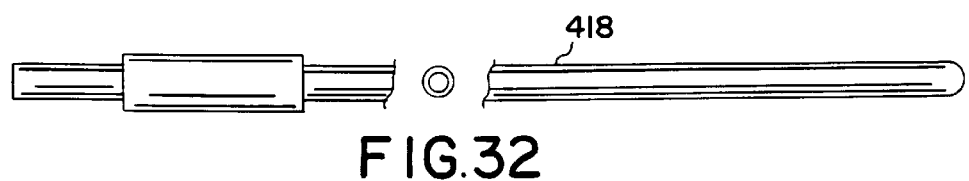
FIG. 32 is a longitudinal view of an acoustic imaging catheter sheath enclosing a drive shaft on which an imaging transducer and an ablation transducer are mounted.
Figure 32A:
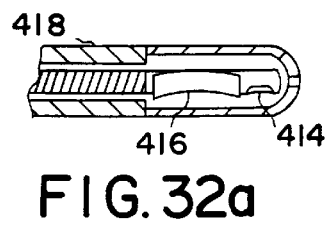
FIG. 32a is a detailed, partially cross-sectional view of the distal tip of the catheter sheath shown in FIG. 32.

Referring to FIGS. 32 and 32a, in catheter sheath 418, an ultrasound transducer 414 is used to ablate tissue sonically. Ultrasound transducer 414 is similar to, and located adjacent to, ultrasound imaging transducer 416 of the type described in detail above. Transducer 416 images by rotating a full 360 degrees while catheter sheath 418 is in a fixed position or a relatively stationary position, the image is stored, and then the rotation of the transducer is stopped and the position of transducer 414 is aligned, based on the stored image, so that transducer 414 is pointed toward the region of interest. During ablation, transducer 414 radiates at least 2–5watts of acoustic power at a frequency of around 25 to 50 kilohertz. This frequency that is so low that the radiation is not focused, but instead tends to radiate from the source in a more or less cardioid pattern without a fixed focus. The energy has its greatest density normal to the surface of transducer 414.

In another embodiment the ablation transducer is positioned in a manner such that it directs radiation in a direction 180 degrees away from the direction in which the imaging transducer directs ultrasound energy, and the ablation transducer and imaging transducer are at the same longitudinal location. The ablation transducer can be aligned in the desired direction for ablating tissue by positioning the imaging transducer in a manner such that the imaging transducer is facing 180° away from the region of interest to be ablated. In yet another embodiment a single transducer is capable of both imaging and very high-power, low-frequency radiation.

Figure 33:
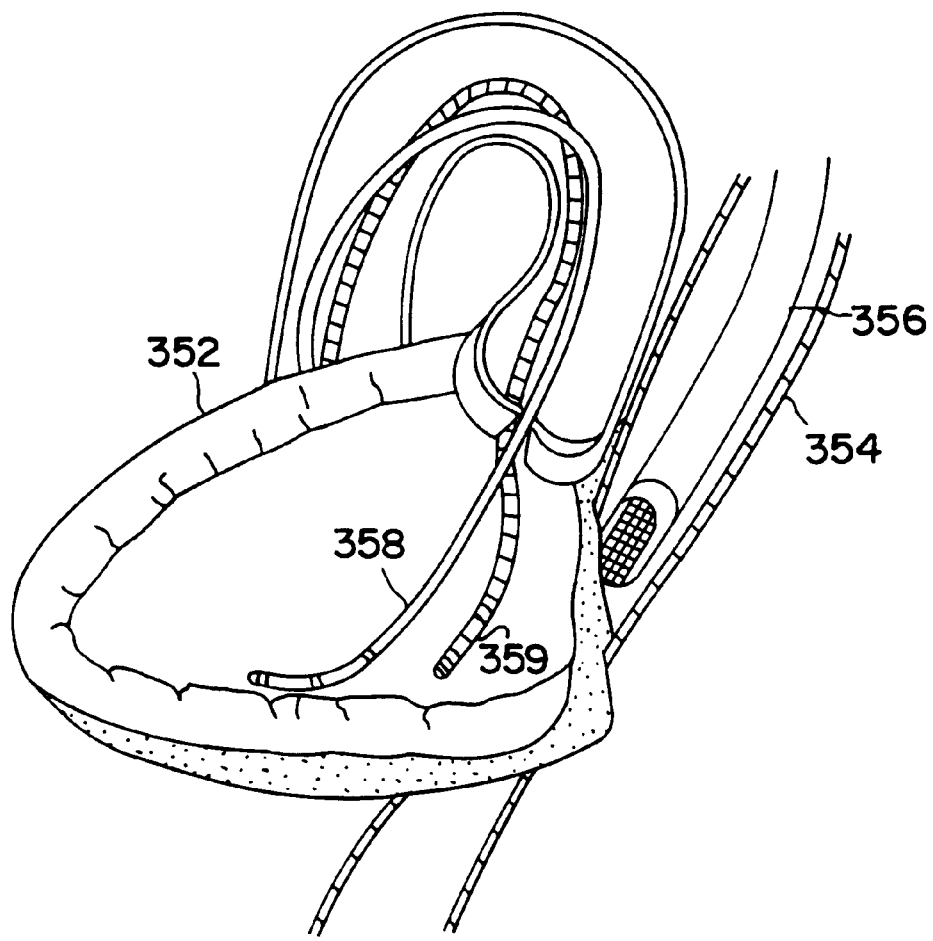
FIG. 33 is a partially cut-away view of a heart and a portion of an esophagus, showing the use of a transesophageal probe in combination with two catheters whose distal portions are located within a heart chamber.

FIG. 33 illustrates an alternative imaging mode that is useful in conjunction with the needle-equipped and balloon-equipped catheters for chemical ablation described above, and also even the electrode-equipped catheters described above, if the electrodes are fitted with polyvinylidene fluoride coverings. According to this imaging mode, the heart 352 is imaged through the esophagus 354, by means of one of many commonly available trans-esophageal probes 356 such as those made by Hewlett Packard, Vingmead and others. This trans-esophageal imaging provides a cross-sectional image of the heart, i.e., a scan plane that is a slice of the heart. Various improved trans-esophageal probes can vary the plane scanned through the heart through various angles and various rotational and azimuthal positions, and can therefore be used to image a very wide area of the heart through manipulation of controls on the proximal end of the transesophageal probe. During use, transesophageal probe 356 is first placed in a patient's esophagus prior to the beginning of an electrophysiology procedure, and electrophysiology or ablation catheters 358 and 359 are then placed in the heart through the venous or the arterial system. These catheters can be visualized by means of esophageal probe 356 if the catheters are fitted with acoustic markers.

The marker may be, for example, a PVDF covering placed over a sensing or ablation electrode, or a PVDF balloon. The acoustic markers are used to create distinct color artifacts on the image created by color flow imaging machines equipped with color capability. The color flow display is a black and white display that has a graphic overlay of flow information, which is denoted by a color shown on the CRT display. When the PVDF is electrically excited it emits a low-frequency sonic wave that is misinterpreted by the trans-esophageal imaging system as the difference between the outgoing ultrasound pulse and the Doppler-shifted return pulse that the trans-esophageal system uses to deduce the direction and quantity of blood flow (the imaging system determines blood flow by measuring the difference between the outgoing and the incoming ultrasound signal and assigning a false color to the frequency shift that occurs due to the Doppler effect). Thus, by radiating at a frequency near the expected Doppler shift frequency, the PVDF basically fools the trans-esophageal imaging system into thinking the low-frequency sonic wave is the difference signal and can induce the imaging system to show false colors that identify particular catheters. A catheter shows up on the display as either a bright mark or dot that represents the cross-section of the catheter. To energize the PVDF a sinusoidal, continuous-wave, voltage signal is applied to the PVDF through a simple, alternating-current, radio-frequency generator. This signal can be pulsed as well, if desired.

One or more of the intra-cardiac catheters may include an ultrasound transducer, which may be adjacent to or at the precise location of sensing and ablation electrodes, as described above. Vacuum-deposited traces may extend along the length of the catheter sheath to the electrodes, as described above. The traces provide good electrical coupling and can serve as an attachment point for PVDF or a crimped-on transducer. The incorporation of the traces into the wall of the catheter sheath leaves the bore of the catheter free to be used for a pacing lead, an anchoring screw, a drug injection channel, a biopsy channel, etc.

In one embodiment, an entire catheter sheath is made of PVDF. The catheter sheath will show up on the display no matter which portion of the catheter sheath intersects with the imaging plane of the transesophageal probe, because the whole catheter sheath emanates radiation. In another embodiment, a first catheter used during the procedure emits a frequency that shows up as a first color on the color flow imaging, a second catheter emits a frequency that shows up as a second color, and so on. In another embodiment the tip or the actual electrode portion of a catheter sheath has a frequency that is distinct from the rest of the catheter sheath, so that when the tip or the electrode is located by the imaging system it is distinguishable from the remainder of the catheter sheath. In another embodiment, there is a graduation in frequency along the length of a catheter, so that a distal tip shows up as a first color, a midsection shows up as a second color, and a proximal section shows up as a third color. The change in frequency along the length of the catheter may be gradual or may be in the form of distinct stripes of different frequencies.

Figure 34:
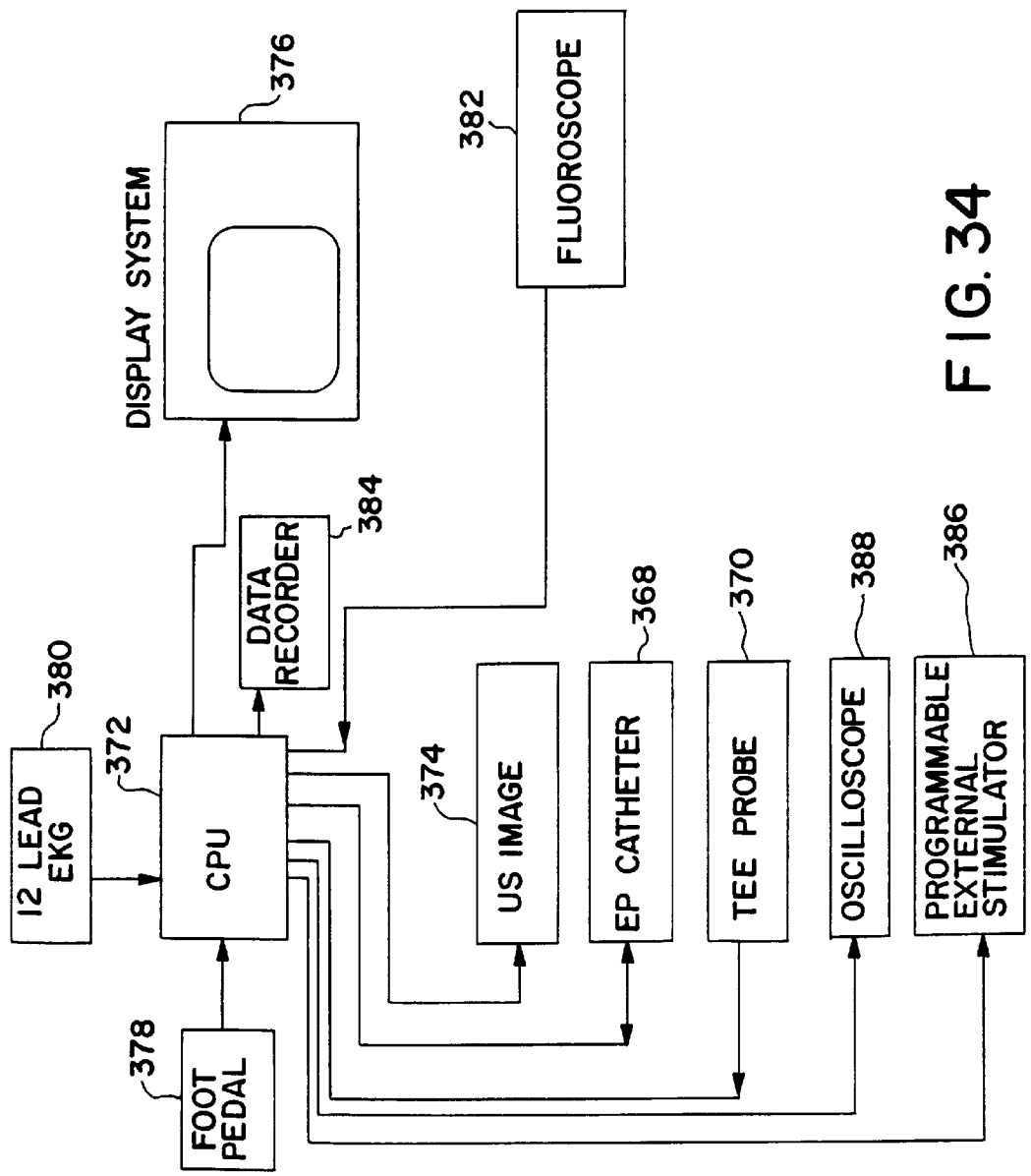
FIG. 34 is a block diagram of the principle components of an acoustic imaging and electrophysiology system that includes an electrophysiology catheter and a display that super-imposes electrophysiology data on an image of the heart.

FIG. 34 illustrates a system of electrophysiology equipment that includes an acoustic imaging electrophysiology catheter 368 of the type shown in FIG. 13, a transesophageal probe 370, a central processing unit 372 that receives data from catheter 368 or trans-esophageal probe 370 and transmits video ultrasonic image data to ultrasound display 374, and another display system 376 that displays, either graphically, schematically, or with a wire frame, specific regions of the heart, and that records and displays on a specific location of the graphical, schematic, or wire frame display either an instantaneous voltage or a voltage throughout an entire cardiac cycle.

In one embodiment, display system 376 displays a two-dimensional cross-sectional image of the heart, which shows important features of the heart such as the area of the HIS bundle. The cross-sectional image is based on ultrasound image received from catheter 368 or trans-esophageal probe 370 or is based on a fluoroscopic image from fluoroscope 382. Other possible sources of the cross-sectional image include MRI, CT, and scintigraphy. When catheter 368 is placed in specific regions of the heart, which can be done with great certainty because of the ultrasound imaging capability, the voltage potentials sensed by catheter 368 are recorded instantaneously by central processing unit 372 and then displayed in the specific locations in the graphic. Many voltage potentials are sensed at various locations in the heart until an electrophysiological map of the heart is built up, which can be done very quickly.

Because the user or the clinician will want to concentrate on maneuvering the catheters, and not on data acquisition, writing information down, or shouting out numbers, a foot pedal 378 is provided so that when catheter 368 is in a specific location the clinician can depress foot pedal 378 to instruct central processing unit 372 to record voltage potential information. Because central processing unit 372 receives ultrasound imaging data, central process unit 372 knows the specific location of each electrophysiology electrode and thus knows the location at which to super-impose voltage data on the image shown by display system 376. Alternatively, the clinician can observe the image displayed by display system 374 and can indicate to central processing unit 372 the specific location of an electrode.

Thus, central processing unit 372 records both an ultrasonic image at a particular instant and a voltage values at that instant and at a particular location. Thus, the clinician can return the sensing electrode to the particular location at a later point in time to compare the voltage sensed at the later point in time with the earlier-recorded voltage.

Moreover, the information recorded by central processing unit 372 permits analysis of various voltage potentials throughout a cardiac cycle as the heart moves during the cycle, because central processing unit 372 is able to keep track of the various locations in the heart even though the heart is moving.

A set of electrocardiogram or EKG leads 380 are connected to central processing unit 372. In one embodiment, when the clinician wants to record a voltage potential, central processing unit 372 records the voltage information throughout one complete cardiac cycle. The clinician can view a representation of the voltage at any instance in time during the cardiac cycle by replaying the image displayed by display system 376 with the super-imposed voltage information. Central processing unit 372 processes ultrasound imaging information and voltage information in the manner of a cine loop or repeating image, which is gated by EKG leads 380 attached to the patient while the patient is left in a still position. The central processing unit causes display system 376 to display a series of successive frames in a loop that repeats over and over again. In one embodiment there are 32 ultrasound imaging frames that go through one complete cardiac cycle from systole to diastole and back to systole, and there are 32 different voltages that are super-imposed on the ultrasound imaging frames at any given location. The super-imposed voltage information at a given location is a number that rises and falls throughout the cardiac cycle, or is alternatively a color coded mark. Thus, there is no need to image the heart continuously, which could take up a lot of software and hardware time, and yet display system 376 displays an image of the heart timed in exact synchronization with the actual heart beating (through use of EKG leads 380) and replayed over and over again. While this image is being replayed, the clinician can concentrate on simply locating the position of catheter 368 itself in the heart and can follow the catheter with trans-esophageal echo probe 370, or through x-rays because catheter 368 is marked with radiopaque markers.

Any additional information that the clinician obtains while the image is being replayed can be super-imposed over the repeating image without the need to re-image the heart. For example, a live fluoroscopic or ultrasound image can be super-imposed over the image being replayed on display system 376. If the super-imposed live image is a fluoroscopic image, it is not necessary to use dye injection while obtaining this live image because the location of the heart tissue relative to the catheter 368 can be seen on display system 376 without any need for the live image itself to show the heart. If the clinician wishes, however, he may update the image by obtaining a new image of the heart, if the patient has moved or if the clinician believes that the heart has changed position or has changed its cycle.

In another embodiment, the display system 376 displays a false three-dimensional image of the heart or a true three-dimensional image of the heart. A false three-dimensional image of the heart is a three-dimensional projection onto a two-dimensional surface that can be generated using commonly available computer imaging hardware and software that takes a number of successive two-dimensional images and assembles them into a false three-dimensional image that can be rotated and manipulated by the user by the user interfacing with central processing unit 372. False three-dimensional ultrasound images can be obtained through the use of accessory software and hardware such as that provided by ImageComm in Sunnyvale, Calif. A true three-dimensional is an image that is not displayed on a flat screen but rather on an oscillating mirror that has a scanning system associated with it that can display a three-dimensional image by stereoscopic means. It is not necessary to wear stereoscopic glasses to view oscillating mirror systems that are currently being marketed.

Alternatively, display system 376 may display a wire-frame image, which is a graphical depiction of the boundaries of the heart and is a simple version of a false 3-dimensional image. The beauty of a wire frame image is that it requires relatively less software and hardware to display and is inherently transparent or translucent so that potentials can be seen through it intuitively by the user. Also, a wire-frame images does not require a large amount of hardware or software to rotate and manipulate the image. The nodal points, i.e. the places where the wires cross, can be used as the data collection points.

One of the very important aspects of the electrophysiology procedure is that once the operation of the heart is diagnosed, the clinician will want, as precisely as possible, to position an ablation device at the source of trouble and ablate the tissue at this location precisely. This requires relocalization of the tip of catheter 368 to a previously located position. All positions at which the catheter tip has been positioned are accurately located on the display of display system 376, and the clinician can determine when the tip of catheter 368 has been relocated by examining the ultrasound image. Thus, the clinician can return to the spot to be ablated with a great degree of confidence.

In one embodiment, trans-esophageal probe 370 creates ultrasound images that are processed by central processing unit 372 and displayed by display system 376, and the ultrasound transducer on catheter 368 is used to create an image displayed on display system 374 to assure good contact of electrodes with tissue. Alternatively, a general sense of the catheter position is obtained through the use of an imaging modality such as fluoroscope 382, and a more precise image is obtained by trans-esophageal probe 370 or the ultrasound transducer on catheter 368 and is processed by central processing unit 372 to create the display for display system 376.

The electrophysiology catheters described in detail above are especially useful for creating an accurate two-dimensional, three-dimensional, or wire-frame image because these catheters are highly maneuverable by their ability to deflect or to be positioned with the assistance of a positioning balloon, because the transducer within these catheters is highly accurate in identifying the position of the catheter relative to tissue, and because these catheters are easily recognizable in trans-esophageal images.

A data recorder 384 is provided in the system of electrophysiology equipment shown in FIG. 34 to record data from EKG leads 380 and the electrophysiology electrodes on catheter 368 in tabular form for analysis. An oscilloscope 388 displays signals from each of the electrophysiology electrodes on catheter 368. A programmable external stimulator 386 is used to provide slight electrical pulses to electrodes on catheter 368 to cause fibrillation so that the action of the heart can be observed while the heart is in this condition.

Other embodiments are within the claims. For example, it is contemplated that each of the various selectable catheter sheaths may incorporate any of the features shown or described in connection with one or more of the other selectable catheter sheaths. Furthermore, the ultrasound transducer described above may be used in conjunction with catheter sheaths incorporating the features of any of the other catheters described in this patent application.

Figure 35:
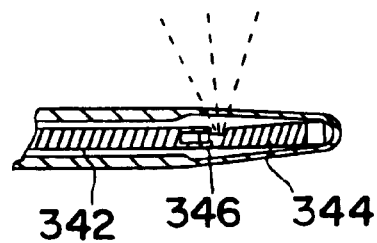
FIG. 35 is a cross-sectional view of a catheter having a rotatable drive shaft on which a mirror is mounted, the mirror being configured to reflect ultrasound signals produced by a transducer.

It is contemplated that each of the various selectable catheter sheaths may be used in conjunction with any of the technologies shown in FIGS. 24, 25, and 26 for enabling relative longitudinal movement between the transducer and the catheter sheath during use of the catheter. Also, each of the various selectable catheter sheaths may be used in conjunction with a drive shaft of the type shown in FIG. 35, in which drive shaft 342 has a rotating mirror 344 on its distal end that reflects an ultrasound signal emitted by an ultrasound transducer 346, which may also be attached to drive shaft 342 as shown or alternatively may be fixed in a stationary position while the drive shaft rotates.

Various Ablation Catheters

Figure 36:
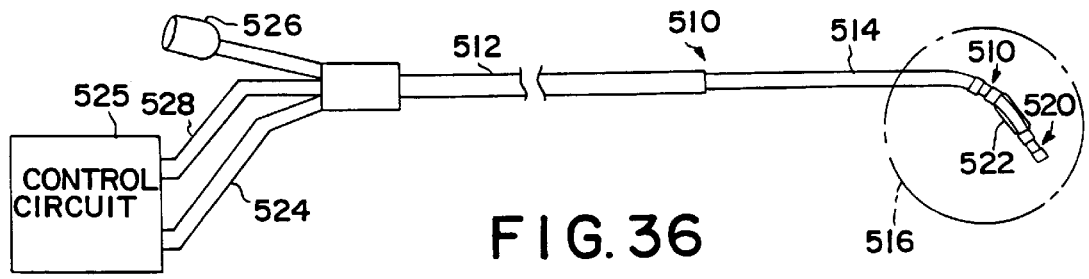
FIG. 36 is a side view of a catheter having a balloon mounted thereon.
Figure 37:
FIG. 37 is an enlarged side view of a portion of the catheter shaft of FIG. 36.

FIG. 36 shows a heated balloon ablation catheter for constructed for insertion into a heart and useful for ablating heart tissue containing abnormal electrical pathways, such as arrhythmogenic foci. The heated balloon ablation catheter comprises catheter shaft 510 having a proximal segment 512 and a distal segment 514. Proximal segment 512 includes an extruded wire 532 braided into catheter shaft 510 (see FIG. 37) for providing strength to the catheter while still maintaining the flexibility required to maneuver the catheter through a vascular system. Wire 532 is preferably made from stainless steel. Distal segment 514 comprises a flexible shaft material, preferably polyurethane, although other flexible biocompatible materials could be used. Catheter shaft 510 is constructed to have one-to-one torqueability.

In one embodiment, distal end 516 of catheter shaft 510 is capable of controlled deflection. A pull-wire (not shown) extends from a handle at the proximal end of the catheter through a lumen in catheter shaft 510 and is fastened to distal end 516 of catheter shaft 510. Distal segment 514 is constructed to be more flexible then proximal segment 512, so that when the handle is pulled back the pull wire causes distal end 516 to bend preferentially from an undeflected position to a deflected position.

Electrode pairs 518 and 520 are mounted on distal end 516 at either side of balloon 522, and are attached to conductors 549 (FIG. 38) that extend through the catheter shaft and that are connected to control circuit 525 by electrical connector 524. Control circuit 525 provides RF energy to the electrodes for ablating cardiac tissue, and also receives voltage potentials from the electrodes when the electrodes are used as electrophysiology mapping electrodes.

Balloon 522 is mounted circumferentially on distal end 516. Balloon 522 is elastic and preferably made from polyethylene cross-linked latex, although other biocompatible elastomer materials can be used. Balloon 522 is coupled to inflation port 526 through an inflation lumen extending along the length of catheter shaft 510. Balloon 522 is inflatable with fluid, preferably saline, which is injected by a syringe at balloon inflation port 526.

Figure 38:
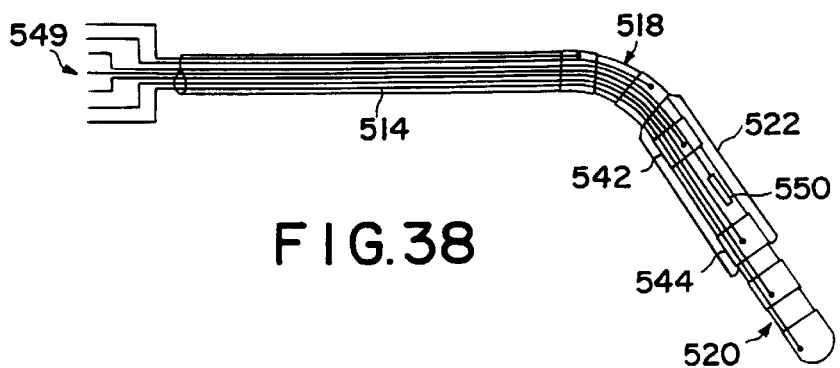
FIG. 38 is a side view of the distal end of the catheter of FIG. 36 with the balloon deflated.
Figure 39:
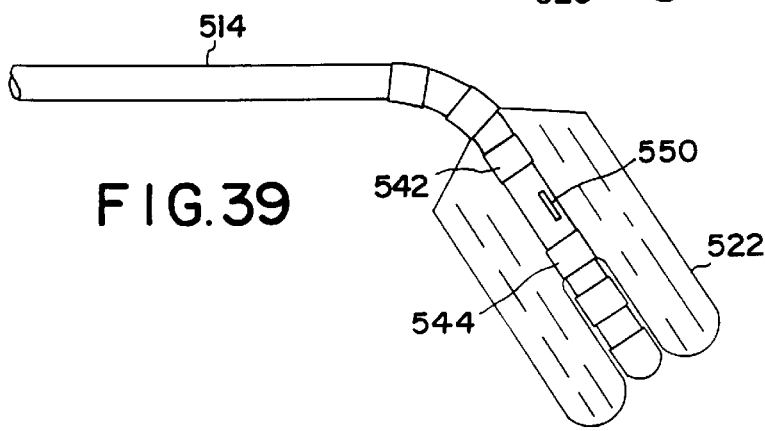
FIG. 39 is a side view of the distal end of the catheter of FIG. 36 with the balloon inflated.
Figure 40:
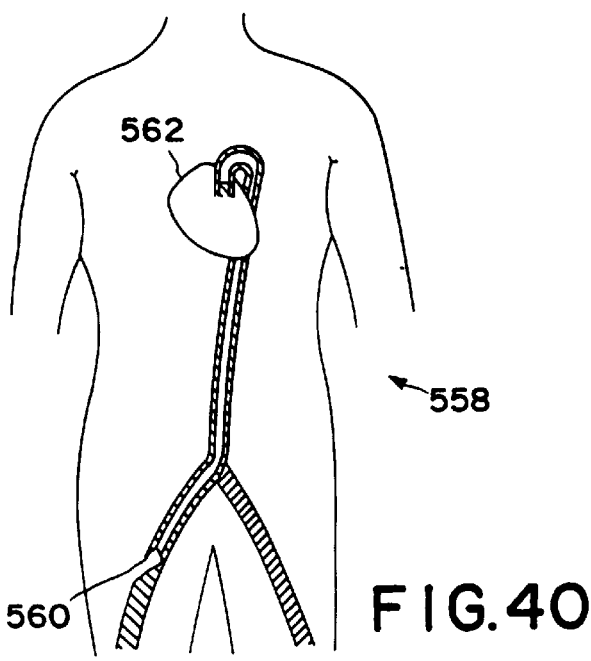
FIG. 40 is a pictorial representation of a human body illustrating a portion of the vascular system.

FIG. 38 shows a side view of distal end 516 with the balloon deflated, and FIG. 39 shows the balloon in its inflated condition. Electrodes 542 and 544 and thermistor 550 within the balloon are coupled to control circuit 525 by wires 549 through electrical connector 528. An RF current can be established between electrodes 542 and 544 for heating the fluid. Control circuit 525 receives signals from thermistor 550 representative of the temperature of the fluid and uses those signals to control the temperature of the fluid by controlling the amount of RF current passed between electrodes 542 and 544, in a manner described in detail in PCT application US93/09422, filed Oct. 4, 1993 by Daniel Bruce Fram et al.

Figure 53:
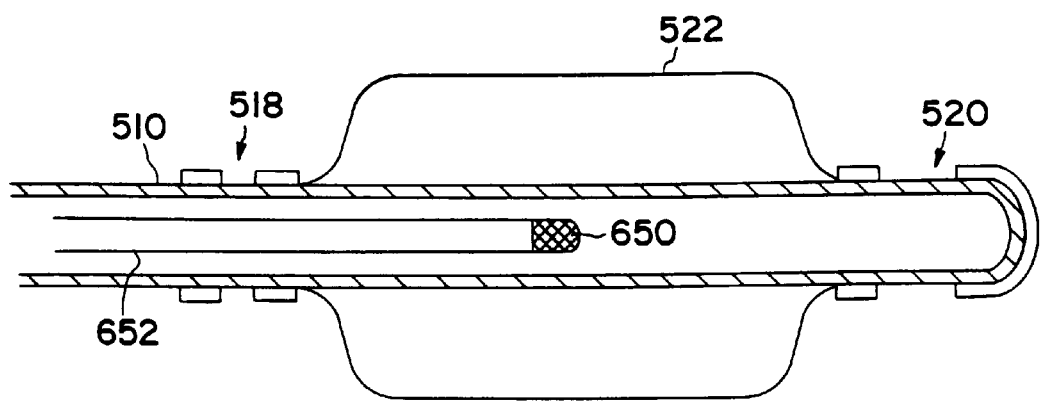
FIG. 53 is a sectional view of a catheter having an inflated balloon and electrodes mounted thereon and having an ultrasonic sensor for producing an ultrasonic image within a patient's body.

FIG. 53 shows a catheter having inflatable balloon 522 and electrodes 518 and 520, and further including an ultrasound transducer 650 mounted at the distal tip of a drive shaft 652 disposed inside catheter shaft 510. Ultrasound transducer 650 is used to produce ultrasound images from which the location of balloon 522 and electrodes 518 and 520 relative to heart tissue may be ascertained. The construction and operation of such an ultrasound transducer is described in detail above. It is contemplated that each of the catheters described in the present application may be combined with such an ultrasound transducer and drive shaft.

Referring to FIGS. 40–44, there are shown pictorial representations of human body 558 illustrating a part of the vascular system. Distal section 516 of catheter shaft 510 is introduced into the vascular system of human body 558 through an opening in femoral vein 560. The catheter is shown entering the left side of the heart, but if the tissue to be ablated is located in the right atrium or ventricle, the catheter is inserted into the right side of the heart. Conventional fluoroscopic techniques can be used to navigate the catheter through the vascular system, if the catheter is provided with radiopaque markers or if a radiopaque contrast medium is used to inflate the balloon.

Figure 41:
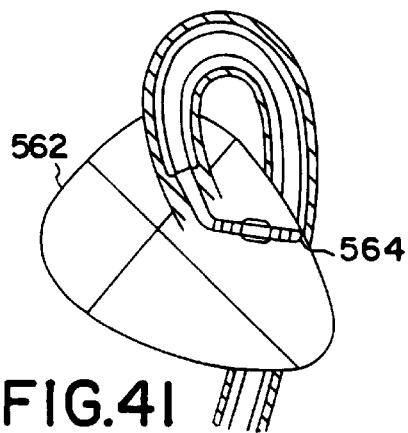
FIG. 41 is a pictorial representation of the catheter of FIG. 36 in the left ventricle with the balloon deflated and with the tip of the catheter in contact with heart tissue.

As shown in FIG. 41, distal tip 564 of the catheter shaft can be brought into contact with a wall of heart 562 by controllably deflecting the distal end of the catheter. The electrode senses electrical potentials within the heart for the purpose of locating cardiac tissue containing abnormal electrical pathways. Control circuit 525 (FIG. 36) can supply RF current to the electrode at distal tip 564 for ablation of localized cardiac tissue.

Figure 42:
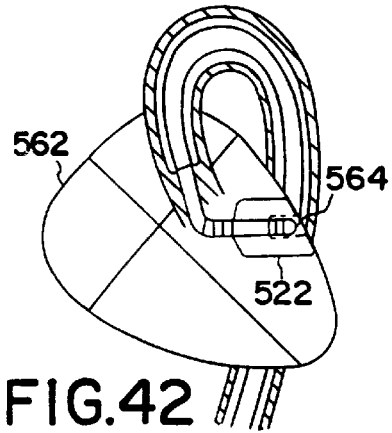
FIG. 42 is a pictorial representation of the catheter of FIG. 36 in the left ventricle with the balloon inflated and with the tip of the balloon in contact with heart tissue.

To ablate a larger area of cardiac tissue near distal tip 564, balloon 522 is inflated with fluid as shown in FIG. 42. The catheter maintains its position by virtue of its torsional rigidity. Alternatively, an ablation suction cup (described below in connection with FIG. 48) is included at the tip of the catheter shaft, the ablation suction cup being used to attach the catheter to the cardiac tissue. Balloon 522 conforms to the heart wall and thus allows a large area of cardiac tissue to be ablated.

When balloon 522 is used to ablate tissue, it is possible to monitor the progress of the ablation by sensing cardiac signals through the electrode located at distal tip 564. The sensed cardiac signals are used by control circuit 525 (FIG. 36) to regulate the RF energy supplied to the fluid inside balloon 522. For example, control circuit 525 can turn off the RF generation the instant the arrhythmogenic myocardium has been ablated to minimize damage to normal cardiac tissue.

Figure 43:
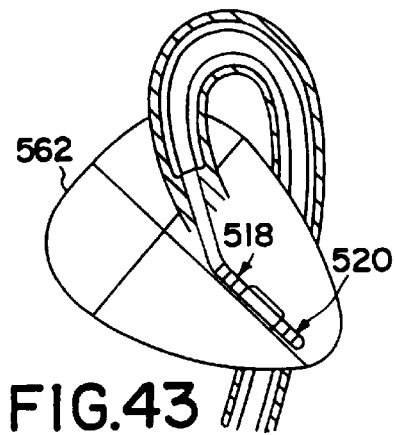
FIG. 43 is a pictorial representation of the catheter of FIG. 36 in the left ventricle with the balloon deflated and with the side of the balloon in contact with heart tissue.

As shown in FIG. 43, the distal end of the catheter can be positioned laterally against a heart wall. Cardiac tissue containing abnormal electrical pathways is located by mapping cardiac signals sensed through any of the electrodes. With balloon 522 deflated, localized myocardium can be ablated by passing RF current from control circuit 525 between bipolar electrode pairs 518 or 520.

Figure 44:
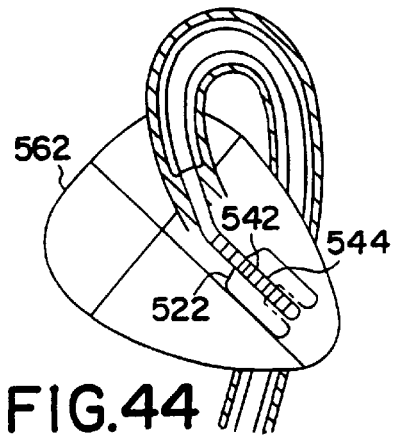
FIG. 44 is a pictorial representation of the catheter of FIG. 36 in the left ventricle with the balloon inflated and with the side of the balloon in contact with heart tissue.

Large areas of myocardium can be ablated by filling balloon 522 with fluid, as shown in FIG. 44. Balloon 522 conforms uniformly to the cardiac tissue over a large area of myocardium. The fluid is heated by passing an RF current between electrodes 542 and 544, and heat is transferred between the fluid and the myocardium, through balloon 522, thereby ablating the myocardium.

Following the ablation, balloon 522 is deflated, as shown in FIG. 43. Electrode pairs 518 and 520 are then used to sense local cardiac electrical activity to determine whether the tissue has been sufficiently ablated. If necessary, the ablation procedure can be repeated.

Figure 45:
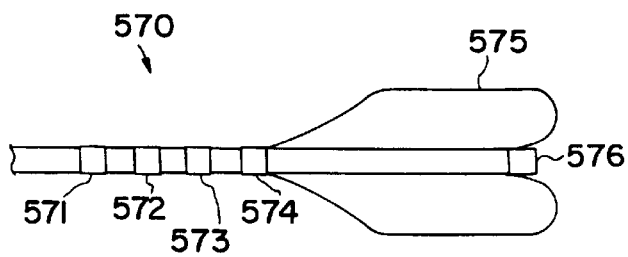
FIG. 45 is a side view of a catheter having an inflated balloon mounted at the distal end of the catheter shaft.
Figure 46:
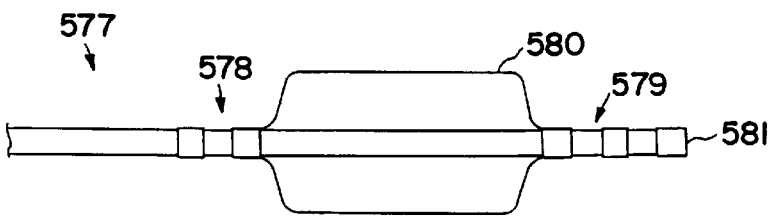
FIG. 46 is a side view of another catheter having an inflated balloon spaced from the distal end of the catheter shaft.
Figure 47:
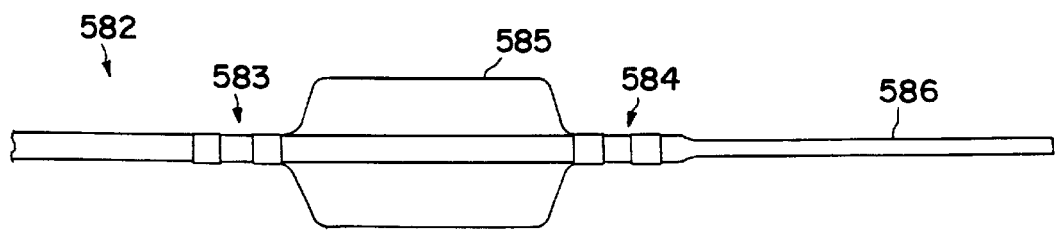
FIG. 47 is a side view of another catheter having an inflated balloon spaced from the distal end of the catheter shaft and having a distal extension for anchoring the distal end of the catheter in a fixed location.

FIG. 45, FIG. 46 and FIG. 47 illustrate different configurations of inflatable balloons and electrodes.

FIG. 45 shows distal end 570 of a catheter having electrodes 571, 572, 573 and 574 positioned on the proximal side of balloon 575. These electrodes are used primarily for mapping of cardiac tissue. However, it is also contemplated that bi-polar pairs of these electrodes may be used to ablate surrounding cardiac tissue. Electrode 576 is used for mapping tissue, as well as for electrophysiological sensing while balloon 575 is being used for ablation. Electrode 576 can also be used for monopolar ablation of tissue at select sites on the cardiac wall.

FIG. 46 shows distal end 577 of a catheter having two sets of bipolar electrodes pairs 578 and 579 mounted on either side of balloon 580. Electrode 581 is mounted on the tip of the catheter for providing additional mapping and/or ablation capability.

FIG. 47 shows a distal end 582 of another catheter, which is identical to the distal end of the catheter shown in FIG. 46 except for the elimination of electrode 581 and the addition of anchoring tip 572. Anchoring tip 572 is made of flexible material, preferably polyurethane, and is capable of controlled deflection in a manner similar to that described above.

Anchoring tip 572 can be positioned in various locations of the heart to stabilize balloon 522 at a desired position against a cardiac wall. For example, anchoring tip 572 can be extended into the coronary sinus while positioning balloon 522 against an atrial wall. Anchoring tip 572 can also be extended through a valve between chambers in the heart for providing additional stability.

FIG. 48 shows a suction catheter for ablating cardiac tissue. Rubber tube 591 couples vacuum pump 590 to vacuum port 592. Vacuum pump 590 can be any non-cycling pump (e.g., an electric pump). A peristaltic pump or other cycled pump should not be used because the vacuum provided would not be uniform.

Vacuum port 592 couples rubber tube 591 to vacuum lumen 612 (see FIG. 49), which extends the entire length of catheter shaft 595. The outside diameter of catheter shaft 595 is approximately eight to ten french, and its length is between one hundred to one hundred-twenty centimeters. Electrical connector 593 couples wires extending through mapping lumen 610 to an external monitoring apparatus and also couples wires extending through lumen 614 to an RF generator.

Retractable handle 594 includes base 596 coupled to catheter shaft 595 and grip 598 slidably mounted on catheter shaft 595 and coupled to retractable shaft 600. Retractable handle 594 has an open position, as shown in FIG. 48, and a closed position, which is obtained by moving grip 598 proximally and engaging it against base 596. Lock 597 restrains retractable handle 594 in either its open or closed position.

Suction cup 602 is coupled to the distal end of retractable shaft 600 and is drawn into cavity 608 at the distal end of catheter shaft 595 by moving retractable handle 594 into its closed position. Suction cup 602 comprises a flexible polymer cup and an ablation electrode 604 lining the inner portion of the polymer cup. Ablation electrode 604 is made of conductive foil as shown in FIG. 48. Alternatively, ablation electrode 604 is made of a series of longitudinally disposed wires extending from the base of suction cup 602 to the outer rim as shown in FIG. 52. Wires extending through lumen 614 couple electrical connector 593 and ablation electrode 604.

It is contemplated that the suction cup feature of the catheter shown in FIG. 48 may be combined with any of the heated balloon electrophysiology catheters described above (substituting the suction cup of FIG. 48 for the distal electrode or distal anchoring extension shown in certain of the drawings).

Referring to FIG. 49, there is shown a sectional view of the suction catheter of FIG. 48, taken along the line I—I in FIG. 49. Conductors extending through mapping lumen 610 couple ring electrodes 606 and electrical port 593. Lumen 614 extends through retractable shaft 600, which is slidably mounted in lumen 601. Conductors disposed in vacuum lumen 612 extend through retractable shaft 600 and couple the electrode on suction cup 602 with an electrical connector at vacuum port 592.

The suction catheter is typically used to ablate tissue in the heart. The distal end of catheter shaft 595 enters the desired chamber of the heart and, local cardiac signals are sensed using ring electrodes 606 which are coupled to electrical connector 593 by conductors extending through mapping lumen 610. Electrodes other than ring electrodes may be used, such as orthogonal electrodes.

Once ring electrodes 606 have located cardiac tissue containing an abnormal electrical pathway, retractable handle 594 is moved into the open position, thereby releasing suction cup 602 from cavity 608. Ablation electrode 604 is then positioned against the tissue, and vacuum pump 590 is turned on. The established vacuum between suction cup 602 and the abnormal tissue causes ablation electrode 604 to be brought into intimate contact with the heart wall. The area of contact between the electrode-lined inner portion of suction cup 602 and the heart wall can be several times larger than the area of contact between a typical tip electrode 570 (see FIG. 45) and a heart wall, thereby allowing a larger area of tissue to be ablated. Once the suction cup is attached to the abnormal tissue, an RF generator coupled to electrical connector 593 causes an RF ablation current to pass between ablation electrode 604 and the cardiac tissue in a monopolar configuration.

Referring to FIG. 50, there is shown a balloon suction ablation catheter. Rubber tube 591 couples vacuum pump 590 and vacuum port 592. Vacuum lumen 630 (FIG. 51) extends the length of the balloon suction ablation catheter and couples vacuum port 592 and distal lumen 625.

Electrical port 624 couples an RF generator to electrodes 635 and 636 inside balloon 628 via conductors that extend the entire length of the catheter through wire lumen 634. Additional conductors disposed in wire lumen 634 couple ring electrodes 621 to electrical connector 622, which is further coupled to a monitor. Inflation port 620, which is constructed to engage a syringe, is coupled to vacuum port 626 inside balloon 628 by inflation lumen 632.

In use of the device, ring electrodes 621 identify abnormal cardiac tissue to be ablated. Fluid, preferably saline, is injected by means of a syringe into inflation lumen 632 to inflate balloon 628 to a desired pressure, which is measured by a pressure gauge.

As shown in FIG. 50, balloon 628 is constructed such that when inflated the distal portion of balloon 628 forms horn cavity 638. Balloon 628, being compliant, allows horn cavity 638 to function as a suction cup. The distal portion of balloon 628 is placed against the cardiac tissue to be ablated and vacuum pump 590 is turned on. The vacuum established between balloon 628 and the tissue causes the balloon suction ablation catheter to become attached to the tissue. An RF current is then established between electrodes 635 and 636, which heats the fluid in balloon 628.

Alternatively, an annular electrode 639, which is coupled to RF port 624 via conductors extending through wire lumen 634, can be used to ablate cardiac tissue. Annular electrode 639 comprises conductive material (e.g., silver or gold) deposited on the surface of horn cavity 638. Alternatively, an annular electrode may be mounted on the distal tip of the catheter shaft immediately surrounding the suction port and immediately adjacent to the balloon.

The temperature inside balloon 628 is monitored by thermistor 627 coupled to electrical port 622 by conductors extending through wire lumen 634. The signal from thermistor 627 can then be used in a feedback circuit for controlling the current delivered by the RF generator for optimizing the ablation of the tissue and to minimize damage to normal tissue.

FIG. 51 is a sectional view of the catheter in FIG. 50 along line II—II showing three lumens disposed therein: vacuum lumen 630, inflation lumen 632 and wire lumen 634.

Other embodiments are within the following claims. For example, any of the inflatable balloons described above may be coated with a conductive material so that the balloon functions as a large, expandable electrode. Examples of such large, expandable electrodes are described below.

Various Heart Ablation Catheters with Expandable Electrodes

FIG. 54 shows, in schematic view, an electrophysiological heart catheter comprising catheter shaft 710 including deflectable tip 712 and deflection actuator 714. On the deflectable portion 712 an expansible balloon 716 is included. At the proximal end an introductory lumen 718 communicates with a source of inflation fluid under pressure. An inflation lumen extending through the catheter shaft connects the interior of the balloon with the introductory lumen 718 for inflation of the catheter.

Referring to FIG. 55, the catheter has ring electrodes 720 and 722 at the respectively proximal and distal ends of the balloon 716. A tip electrode 724 and further ring electrodes proximal of the balloon 726 and 728 are also included. An electrical power source wire 730 makes electrical contact with a conductive coating 732 that is generally applied over the balloon surface. As suggested, the wire proximal of the balloon passes inwardly through the wall thickness of the catheter and then proceeds to the proximal end where it connects to a cable 733 that couples to a suitable RF control unit. The handle 734 is grasped while moving the actuator 714 axially to cause deflection as suggested in the dotted lines in FIG. 54.

As seen in FIG. 55, the balloon in uninflated condition has a diameter substantially corresponding to that of the catheter. Fold lines 736 are shown suggesting that the balloon is folded in the way employed with dilatation catheters.

In FIG. 56 the balloon is shown to be inflated, e.g. at 8 to 10 atmospheres. So inflated the balloon becomes quite rigid and capable of pressing against heart tissue sufficiently to make good electrical contact. The area of tissue contacted is in proportion to the diameter of the balloon which as can be seen in FIG. 56, when inflated can be as much as three times as large as the diameter of the shaft per se.

Figure 57:
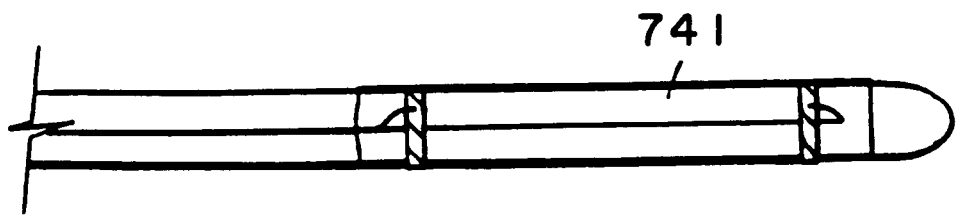
FIG. 57 is a side view of a distal portion of an electrophysiological heart catheter having a deflated balloon with two conductive stripes applied to the surface of the balloon.
Figure 58:
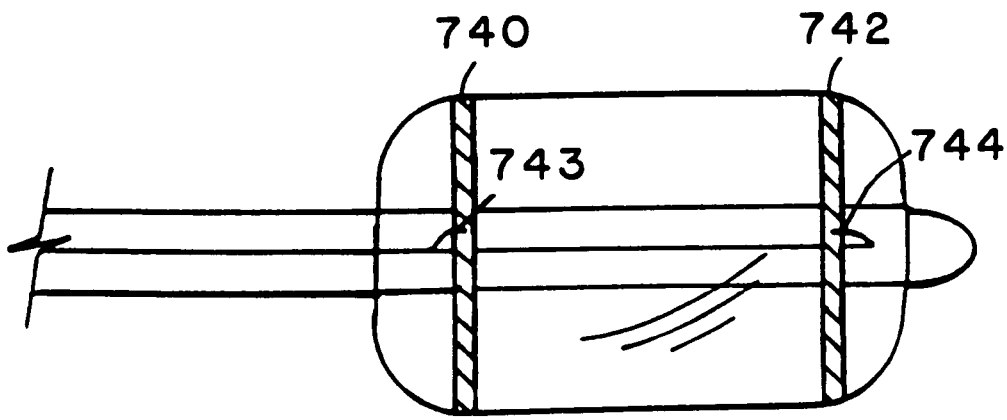
FIG. 58 is a side view of the electrophysiological heart catheter of FIG. 57, with the balloon in its inflated state.

The embodiment of FIGS. 57 and 58 employs a similar catheter shaft and a similar balloon material. In this case, two axially spaced-apart conductive stripes 740 and 742 are applied to the balloon surface, preferably made from gold. In this embodiment, RF current is introduced in a bipolar manner for ablating surface tissue.

FIG. 57 indicates that the balloon 741 can fold in a similar manner as the balloon of FIG. 55 to conform substantially to the size of the catheter.

FIG. 58 shows the balloon inflated, e.g., at 8 to 10 atmospheres. Electrical leads 743 and 744 deliver the RF current to the conductive stripes.

FIG. 59 shows, in schematic view, an electrophysiological heart catheter that includes catheter shaft 745, distal portion 744 and inflation port 747. Metering device 746 couples to inflation port 747 for injecting a controlled amount of fluid into balloon 748 through an inflation lumen extending the length of catheter shaft 745. Metering device 746 is preferably a screw syringe as used in balloon angioplasty.

As seen in FIG. 60, the balloon in uninflated condition has a diameter substantially corresponding to that of the catheter. Balloon 748 is made from elastomeric material which has a plurality of tightly spaced conductive dots 750 disposed on its surface. Tip electrode 749 is provided for sensing cardiac signals. Any number of ring electrodes may also be disposed along distal portion 744 to provide additional sensing capability.

FIG. 61 shows the balloon 748 inflated to a mid-size while FIG. 62 illustrates the balloon inflated more fully. The spacing between the dots allows the balloon to expand to a desired size. The size of the balloon can be precisely controlled by employing metering device 746. Electrode 752 is coupled to a suitable RF control unit via wire 753. Monopolar RF energy delivered to electrode 752 capacitively couples to conductive dots 750 which are used to ablate cardiac tissue. In this case, electrically conductive fluid is employed as the inflation medium for the balloon. Capacitive coupling occurs across the thickness of the balloon to the conductive dots on the surface of the balloon.

Figure 63:
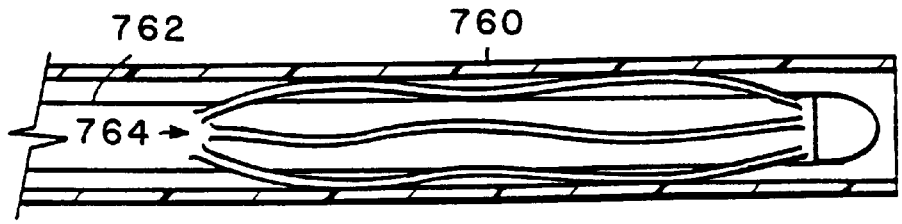
FIG. 63 is a side view of a distal portion of an electrophysiological heart catheter having a sheath that compresses a set of flexible members.
Figure 64:
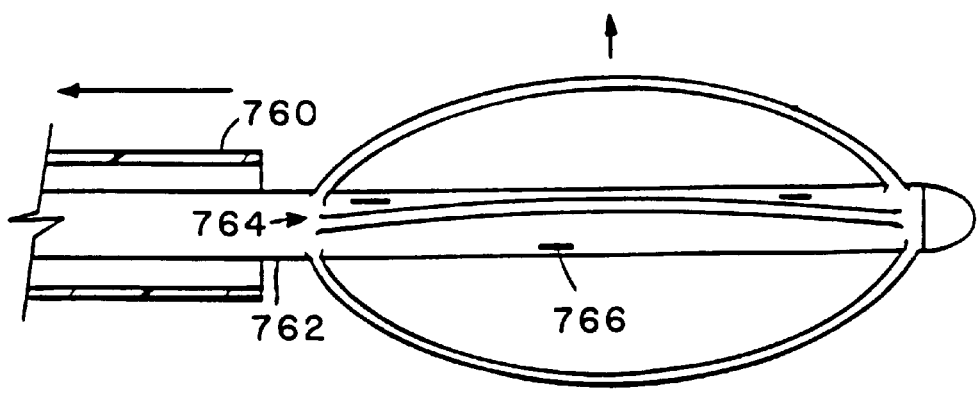
FIG. 64 is a side view of the electrophysiological heart catheter of FIG. 63, with the sheath retracted and the flexible members in an expanded condition.

The embodiments of FIGS. 63 and 64 employ a retractable sheath 760 to compress flexible members 764 to conform substantially to the diameter of catheter shaft 762 for navigation through the venous system and into the heart. Flexible members 764 are either made from conductive material or are coated with a conductive material for suitably receiving RF energy to ablate cardiac tissue. The conductive material is preferably gold.

FIG. 63 shows the sheath extended to the distal end of catheter shaft 762 thereby restraining flexible members 764. FIG. 64 shows sheath 760 retracted proximally of the catheter, allowing the flexible members to expand away from catheter shaft 762.

Sensing electrodes 766 are longitudinally disposed along the length of the catheter shaft. FIGS. 63 and 64 show sensing electrodes 766 axially rotated relative to each other. Each electrode shown has a corresponding electrode mounted on the opposite side of the catheter shaft in the plane perpendicular to the longitudinal axis of the catheter shaft. These electrodes form orthogonal electrode pairs for sensing local cardiac electrical signals. Alternatively, sensing ring electrodes could be disposed along catheter shaft 762. A sensing and/or ablation tip electrode may also be disposed at the distal tip of the catheter shaft.

In an alternative embodiment the catheter shaft could comprise two slidably moveable segments having an extended position and a retracted position. The extended position is characterized by having a tensioning wire maintaining the distal ends of the moveable segments farthest apart, while the retracted position is characterized by releasing the tension in the tensioning wire and having the distal ends of the moveable segments move closer together. Flexible members 764 are mounted such that the two ends of each member are connected to different segments of the catheter shaft. With the catheter segments in the extended position the flexible members are drawn against the catheter shaft, while in the retracted position the flexible members bow away from the catheter shaft.

The embodiments of FIGS. 65 through 69 employ catheter shafts having two slidably moveable segments, the inner segment having an extended position and a retracted position as described above.

Figure 65:
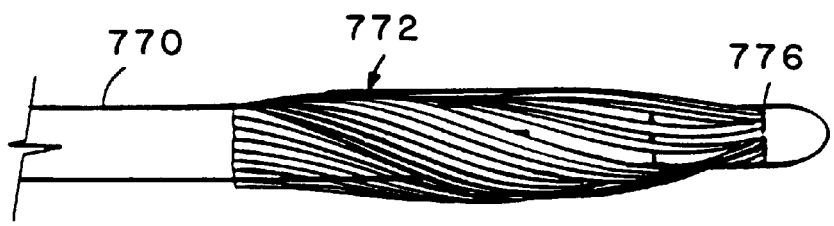
FIG. 65 is a side view of a distal portion of an electrophysiological heart catheter shaft having a set of flexible members drawn tightly around the catheter shaft.
Figure 66:
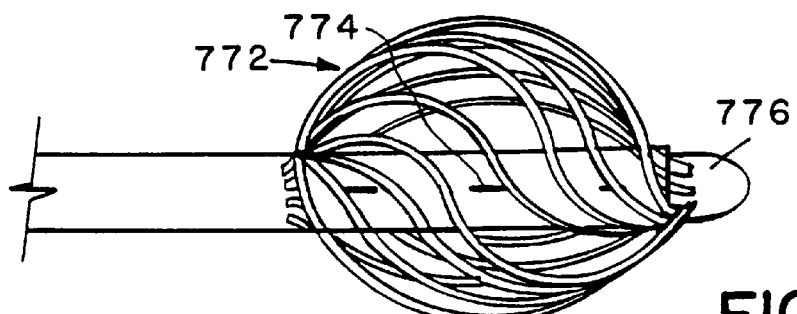
FIG. 66 is a side view of the electrophysiological heart catheter of FIG. 65, showing the flexible members expanded away from the catheter shaft.

FIG. 65 shows inner catheter segment 776 in the extended position, with flexible members 772 drawn against outer catheter segment 770. FIG. 66 shows inner catheter segment 776 in the retracted position, segment 776 resting deeper within segment 770 than in FIG. 65. As shown in FIG. 66, in the retracted position flexible members 772 bow away from the catheter shaft providing a larger ablation region. If a more spatially uniform ablation is desired, a greater number of flexible members may be employed.

Sensing electrodes 774 can be disposed along the catheter shaft for sensing. A sensing and/or ablation electrode can also be included at the distal tip of catheter segment 776.

Another embodiment is shown in FIGS. 67 and 68. FIG. 67 illustrates the distal segment 784 in an extended position (distal segment 784 being pulled out from segment 780). In the extended position alternating flexible members 782 are drawn against the catheter shaft. FIG. 68 shows distal segment 784 in the retracted position (segment 784 being retracted inside segment 780), allowing flexible members 782 to extend away from the catheter shaft.

In certain circumstances it is advantageous to employ ultrasound imaging in connection with the ablation technique. FIG. 69 shows a sectional view of the catheter shown in FIG. 56, taken along the line I—I, the catheter additionally including an ultrasound transducer 790 coupled to drive shaft 792, which extends the entire length of the catheter through a lumen disposed therein. Ultrasound imaging can be used to monitor the lesion forming during ablation. It is contemplated that ultrasound imaging could be employed with any of the embodiments described. Details of ultrasound imaging catheters are described above.

Figure 80:
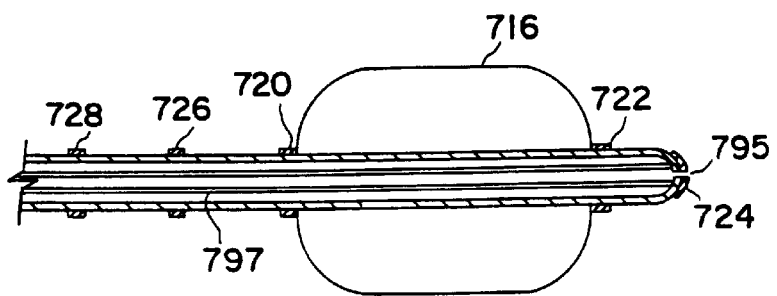
FIG. 80 is a partially sectional view of the distal portion of a catheter of the type shown in FIG. 56 that additionally includes a port for introduction of fluid to an ablation site.

In other instances, it is advantageous to provide a fluid dispensing lumen as part of the catheter for the purpose of augmenting the ablation effect at the tissue. FIG. 80 shows a sectional view of the catheter shown in FIG. 56 taken along the line I—I, the catheter additional including a dispensing lumen 797, which is coupled with a fluid dispenser at the proximal end of the catheter and feeds into dispensing port 795. The fluid introduced into the dispensing port may be selected to be highly electrically conductive relative to that of blood and thus can render the zone where the fluid is introduced to tissue at dispensing port 795 preferentially conductive and thus create a zone where most of the ablative current will flow. Other fluids, such as alcohol, may be added to augment the ablation effect. The dispensing port may be located at any desirable location on the distal portion of the catheter.

FIGS. 70 through 74, which show a catheter extending through the left atrium of a heart and into the left ventricle, illustrate a typical method of use for the balloon electrode embodiments of FIGS. 54 through 62. The left side of the heart is typically accessed by inserting the distal end of a catheter in an opening in the femoral vein of a patient and navigating the catheter through the venous system. Other chambers of the heart are also accessible to the invention and are treatable by means of catheters according to the invention.

FIG. 70 shows the deflected distal end of a catheter shaft extending through the left atrium of a heart and positioned against a wall of the ventricle. FIG. 71 shows an enlarged view of the portion of FIG. 70 contained in region 800. Positioned against the heart wall, the ring electrodes and the distal tip electrode can be employed to locate regions of cardiac tissue to be ablated.

Figure 72:
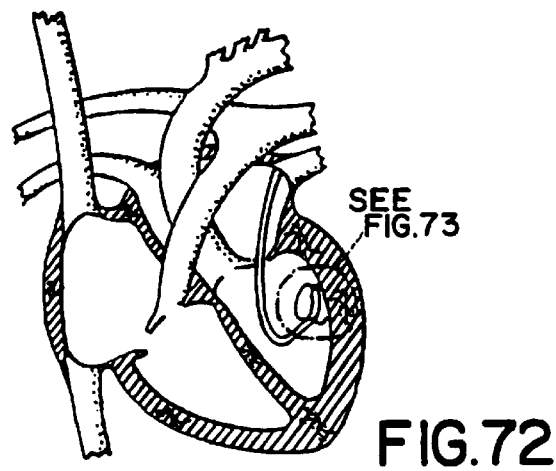
FIG. 72 is a partially cross-sectional view of a catheter in the left side of a heart, showing a balloon electrode in an inflated condition.
Figure 73:
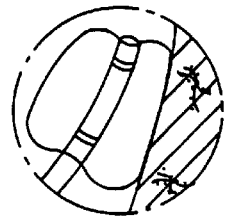
FIG. 73 is an enlarged view of a portion of FIG. 72.

Once an ablation site has been located, the balloon electrode is controllably inflated to the desired size, corresponding to the area of the ablation region, and is pressed against the tissue at the ablation site as shown in FIGS. 72 and 73. The tissue is ablated in accordance with the electrode embodiment employed. The ablation effect may be augmented by introducing conductive fluid or alcohol to the ablation site. During the ablation, ultrasound imaging can be employed to observe the resulting lesion being formed. Alternatively, the ring or distal tip electrodes may be used to sense electrical potentials during the ablation procedure.

Figure 74:
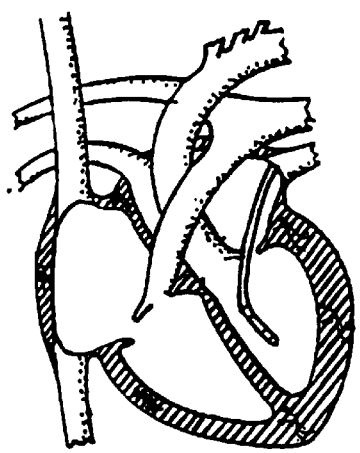
FIG. 74 is a partially cross-sectional view of a catheter in the left side of a heart, showing a balloon electrode in a deflated condition and removed from contact with heart tissue.

FIG. 74 shows the catheter with a deflated balloon electrode approaching a different wall of the ventricle, where the above procedure can be repeated if necessary.

FIGS. 75 through 79 illustrate a typical method of use for the mechanical electrode embodiments of FIGS. 63 through 68. Specifically, the embodiment of FIGS. 63 and 64 is illustrated, although the other embodiments would function similarly.

Figure 75:
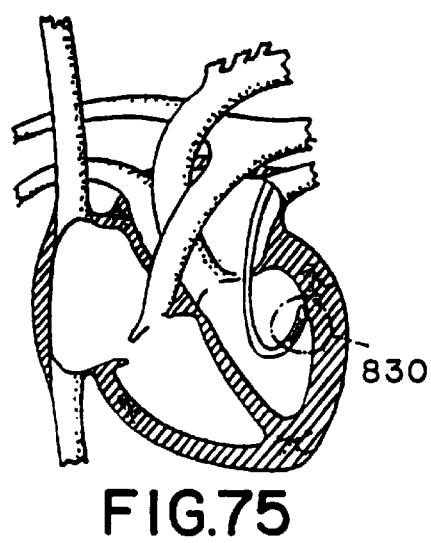
FIG. 75 is a partially cross-sectional view of a catheter in the left side of a heart, showing a mechanical electrode in a non-expanded condition and in contact with heart tissue.
Figure 76:
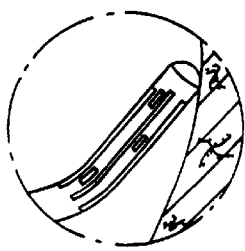
FIG. 76 is an enlarged view of a portion of FIG. 75.

FIG. 75 shows the deflected distal end of a catheter shaft extending through the left atrium of a heart and positioned against a wall of the ventricle. FIG. 76 shows an enlarged view of the portion of FIG. 75 contained in region 830. Positioned against the heart wall, the mapping electrodes can be employed to locate regions of cardiac tissue to be ablated.

Figure 77:
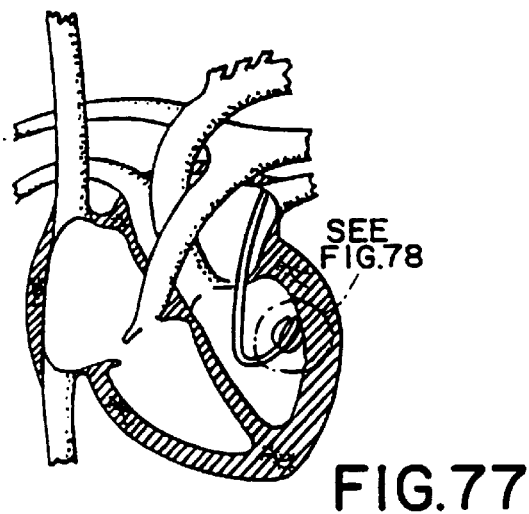
FIG. 77 is a partially cross-sectional view of a catheter in the left side of a heart, showing a mechanical electrode in an expanded condition.
Figure 78:
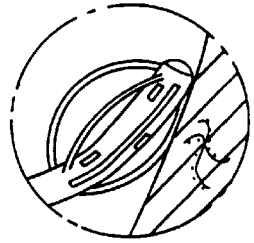
FIG. 78 is an enlarged view of a portion of FIG. 77.

Once an ablation site has been located, the mechanical electrode is controllably expanded to the desired size, corresponding to the area of the ablation region, and is pressed against the tissue at the ablation site as shown in FIGS. 77 and 78. The tissue is ablated by passing RF current between the mechanical electrode and an electrode external to the patient's body in a monopolar configuration. The ablation effect may be augmented by introducing conductive fluid or alcohol to the ablation site. During the ablation, ultrasound imaging can be employed to observe the resulting lesion being formed. Alternatively, the mapping electrodes may be used to sense electrical potentials during the ablation procedure.

Figure 79:
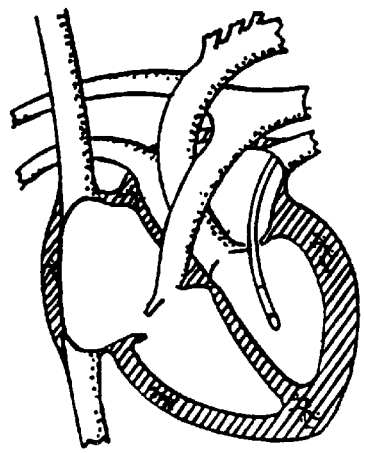
FIG. 79 is a partially cross-sectional view of a catheter in the left side of the heart, showing a mechanical electrode in a non-expanded condition and removed from contact with heart tissue.

FIG. 79 shows the catheter with a retracted mechanical electrode approaching a different wall of the ventricle, where the above procedure can be repeated if necessary.

Other embodiments are within the following claims. For example, the expandable balloons in accordance with the present invention may be heated balloons of the type described above.

What is claimed is:

1. An acoustic imaging system for use within a body of a living being, comprising:
   an elongated, flexible catheter constructed to be inserted into said body of said living being,
   an ultrasound device incorporated into said elongated, flexible catheter, said ultrasound device being arranged to direct ultrasonic signals toward an internal structure within said body of said living being for the purpose of creating an ultrasonic image of said internal structure,
   an electrode mounted on a distal portion of said elongated, flexible catheter, said electrode being arranged for electrical contact with said internal structure imaged by said ultrasound device,
   a balloon mounted on said distal portion of said elongated, flexible catheter, said balloon being constructed to cause ablation of at least a portion of said internal structure imaged by said ultrasound device, said balloon comprising a material that vibrates in response to electrical excitation, said ablation being at least assisted by vibration of said material, and
   a plurality of electrical conductors extending from a proximal portion of said elongated, flexible catheter to said distal portion, at least two of said plurality of electrical conductors being connected to said ultrasound device, at least one of said plurality of electrical conductors being connected to said electrode, and at least two of said plurality of electrical conductors being connected to said material of said balloon to cause vibration thereof.

2. An acoustic imaging system for use within a body of a living being, comprising:
   an elongated, flexible catheter constructed to be inserted into said body of said living being, said catheter comprising a tubular shaft member,
   an ultrasound device incorporated into said elongated, flexible catheter, said ultrasound device being arranged to direct ultrasonic signals toward an internal structure within said body of said living being for the purpose of creating an ultrasonic image of said internal structure,
   an electrode mounted on a distal portion of said elongated, flexible catheter on said tubular shaft member, said electrode being arranged for electrical contact with said internal structure imaged by said ultrasound device,
   a plurality of electrical conductors extending from a proximal portion of said elongated, flexible catheter to said distal portion, at least two of said plurality of electrical conductors being connected to said ultrasound device and at least one of said plurality of electrical conductors being connected to said electrode, and
   a balloon mounted on said distal portion of said elongated, flexible catheter, said balloon is constructed to assist in positioning said catheter in the vicinity of said internal structure and to press said catheter against a wall of said internal structure of said body of said living being.

3. An ablation system for use within a body of a living being, comprising:
   an elongated, flexible catheter constructed to be inserted into said body of said living being,
   an ablation device mounted on a distal portion of said elongated, flexible catheter, said ablation device comprising a balloon, said balloon comprising a wall with ports for delivery of a fluid to said internal structure of said body of said living being, and
   a plurality of electrical conductors extending from a proximal portion of said elongated, flexible catheter to said distal portion,
   said ablation device comprising a material that vibrates in response to electrical excitation, at least two of said plurality of electrical conductors being connected to said material to cause vibration thereof, said ablation device being constructed and arranged to cause ablation of at least a portion of an internal structure within said body of said living being, said ablation being at least assisted by vibration of said material.

4. An ablation system for use within a body of a living being, comprising:
- an elongated, flexible catheter constructed to be inserted into said body of said living being,
- an ablation device mounted on a distal portion of said elongated, flexible catheter, said ablation device comprising a balloon,
- a plurality of electrical conductors extending from a proximal portion of said elongated, flexible catheter to said distal portion,
- said ablation device comprising a material that vibrates in response to electrical excitation, at least two of said plurality of electrical conductors being connected to said material to cause vibration thereof, said ablation device being constructed and arranged to cause ablation of at least a portion of an internal structure within said body of said living being, said ablation being at least assisted by vibration of said material, and
- a needle constructed to inject a fluid into said internal structure of said body of said living being, said vibration of said balloon assisting in delivery of fluid into said internal structure.

5. An ablation system in accordance with claim 4, wherein said needle extends from a side wall of said catheter.

6. An ablation system for use within a body of a living being, comprising:
- an elongated, flexible catheter constructed to be inserted into said body of said living being,
- an ablation device mounted on a distal portion of said elongated, flexible catheter, and
- a plurality of electrical conductors extending from a proximal portion of said elongated, flexible catheter to said distal portion,
- said ablation device comprising a material that vibrates in response to electrical excitation, said material being sonolucent, at least two of said plurality of electrical conductors being connected to said material to cause vibration thereof, said ablation device being constructed and arranged to cause ablation of at least a portion of an internal structure within said body of said living being, said ablation being at least assisted by vibration of said material.

7. An ablation system in accordance with claim 6, wherein said material is polyvinylidene fluoride.

8. An ablation system in accordance with claim 6, wherein said ablation device comprises a needle.

9. An ablation system in accordance with claim 8, wherein said needle is constructed to inject a fluid into said internal structure of said body of said living being.

10. An ablation system in accordance with claim 6, further comprising an ultrasound device incorporated into said elongated, flexible catheter, said ultrasound device being arranged to direct ultrasonic signals toward said internal structure within said body of said living being for the purpose of creating an ultrasonic image of said internal structure, and said ablation device arranged for ablation of at least a portion of said internal structure imaged by said ultrasound device.

11. An ablation system for use within a body of a living being, comprising:
- an elongated, flexible catheter constructed to be inserted into said body of said living being,
- an ablation device mounted on a distal portion of said catheter, said ablation device comprising a balloon, and
- a plurality of electrical conductors extending from a proximal portion of said catheter to said distal portion, said ablation device comprising a material that vibrates in response to electrical excitation, at least two of said plurality of electrical conductors being connected to said material to cause vibration thereof, said ablation device being constructed and arranged to cause ablation of at least a portion of an internal structure within said body of said living being, said ablation being at least assisted by vibration of said material.

12. An acoustic imaging system for use within a body of a living being, comprising:
- an elongated, flexible catheter constructed to be inserted into said body of said living being, said catheter comprising a steering device constructed to cause bending of said distal portion of said catheter, said steering device comprising a control mechanism at a proximal portion of said catheter arranged to control said bending of said distal portion of said catheter,
- an ultrasound device incorporated into said catheter, said ultrasound device being arranged to direct ultrasonic signals toward an internal structure within said body of said living being for the purpose of creating an ultrasonic image of said internal structure,
- an electrode mounted on a distal portion of said catheter, said electrode being arranged for electrical contact with said internal structure imaged by said ultrasound device,
- a plurality of electrical conductors extending from a proximal portion of said catheter to said distal portion, at least two of said plurality of electrical conductors being connected to said ultrasound device, and at least one of said plurality of electrical conductors being connected to said electrode, and
- a balloon mounted on said distal portion of said catheter and constructed to cause ablation of at least a portion of said internal structure imaged by said ultrasound device, said balloon comprising a material that vibrates in response to electrical excitation, at least two of said plurality of electrical conductors being connected to said material to cause vibration thereof, said ablation being at least assisted by vibration of said material.

13. An acoustic imaging system for use within a body of a living being, comprising:
- an elongated, flexible catheter having a tubular shaft member and constructed to be inserted into said body of said living being, said catheter comprising a steering device constructed to cause bending of said distal portion of said catheter, said steering device comprising a control mechanism at a proximal portion of said catheter arranged to control said bending of said distal portion of said catheter,
- an ultrasound device incorporated into said catheter, said ultrasound device being arranged to direct ultrasonic signals toward an internal structure within said body of said living being for the purpose of creating an ultrasonic image of said internal structure,
- an electrode mounted on a distal portion of said catheter on said tubular shart mebmer, said electrode being arranged for electrical contact with said internal structure imaged by said ultrasound device,
- a plurality of electrical conductors extending from a proximal portion of said catheter to said distal portion, at least two of said plurality of electrical conductors being connected to said ultrasound device, and at least one of said plurality of electrical conductors being connected to said electrode, and
- a balloon mounted on said distal portion of said catheter and constructed to assist in positioning said catheter in the vicinity of said internal structure and press said catheter against a wall of said internal structure of said body of said living being.

* * * * *